(12) United States Patent
Panitch et al.

(10) Patent No.: US 9,327,008 B2
(45) Date of Patent: *May 3, 2016

(54) CELL-PERMEANT PEPTIDE-BASED INHIBITOR OF KINASES

(75) Inventors: Alyssa Panitch, West Lafayette, IN (US); Brandon Seal, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 728 days.

This patent is subject to a terminal disclaimer.

(21) Appl. No.: 12/634,476

(22) Filed: Dec. 9, 2009

(65) Prior Publication Data

US 2010/0158968 A1 Jun. 24, 2010

Related U.S. Application Data

(60) Provisional application No. 61/121,396, filed on Dec. 10, 2008.

(51) Int. Cl.
*A61K 38/16* (2006.01)
*A61K 38/04* (2006.01)

(52) U.S. Cl.
CPC .............. *A61K 38/04* (2013.01); *A61K 38/16* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,175,144 A | 12/1992 | Walser | |
| 5,415,864 A | 5/1995 | Kopecek et al. | |
| 5,565,350 A | 10/1996 | Kmiec et al. | |
| 6,855,693 B2 | 2/2005 | Mochly-Rosen et al. | |
| 6,921,527 B2 | 7/2005 | Platz et al. | |
| 7,041,814 B1 | 5/2006 | Weinstock et al. | |
| 7,135,453 B2 | 11/2006 | Brophy et al. | |
| 7,361,352 B2 | 4/2008 | Birkett et al. | |
| 8,536,303 B2 | 9/2013 | Panitch et al. | |
| 8,741,849 B2 | 6/2014 | Panitch et al. | |
| 2002/0009491 A1 | 1/2002 | Rothbard et al. | |
| 2002/0041899 A1 | 4/2002 | Chudzik et al. | |
| 2002/0128444 A1 | 9/2002 | Gingras et al. | |
| 2003/0134810 A1 | 7/2003 | Springate et al. | |
| 2003/0187232 A1 | 10/2003 | Hubbell et al. | |
| 2003/0190364 A1 | 10/2003 | Panitch et al. | |
| 2005/0153372 A1 | 7/2005 | Greengard et al. | |
| 2006/0024264 A1 | 2/2006 | Kuroda et al. | |
| 2006/0035814 A1 | 2/2006 | Brophy et al. | |
| 2006/0115453 A1 | 6/2006 | Yaffe | |
| 2006/0293234 A1* | 12/2006 | Schroeder | 514/12 |
| 2007/0026518 A1 | 2/2007 | Healy et al. | |
| 2007/0078092 A1 | 4/2007 | Livnah et al. | |
| 2007/0154448 A1 | 7/2007 | Reid et al. | |
| 2007/0202189 A1 | 8/2007 | Ahlfors | |
| 2008/0038352 A1 | 2/2008 | Simpson et al. | |
| 2008/0113971 A1 | 5/2008 | Hanau et al. | |
| 2008/0132443 A1 | 6/2008 | Brophy et al. | |
| 2008/0293640 A1 | 11/2008 | Brophy et al. | |
| 2009/0149389 A1 | 6/2009 | Panitch et al. | |
| 2009/0176694 A1 | 7/2009 | Brophy et al. | |
| 2009/0176695 A1 | 7/2009 | Brophy et al. | |
| 2009/0196927 A1 | 8/2009 | Panitch et al. | |
| 2009/0258819 A1 | 10/2009 | Brophy et al. | |
| 2009/0269406 A1 | 10/2009 | Panitch et al. | |
| 2010/0004165 A1 | 1/2010 | Brophy et al. | |
| 2010/0009903 A1 | 1/2010 | Brophy et al. | |
| 2010/0098760 A1 | 4/2010 | Panitch | |
| 2010/0158968 A1 | 6/2010 | Panitch | |
| 2011/0052658 A1* | 3/2011 | Panitch et al. | 424/423 |
| 2011/0288036 A1* | 11/2011 | Lander et al. | 514/21.4 |
| 2012/0263680 A1 | 10/2012 | Lander et al. | |
| 2013/0101671 A9* | 4/2013 | Panitch | 424/484 |
| 2014/0112947 A1 | 4/2014 | Panitch et al. | |

FOREIGN PATENT DOCUMENTS

| | | |
|---|---|---|
| CA | 2689296 | 7/2008 |
| CN | 1747949 | 3/2006 |
| JP | 2002-505077 | 2/2002 |
| JP | 2006-515159 | 2/2004 |
| WO | WO 91/16038 | 10/1991 |
| WO | WO 93/22443 | 11/1993 |

(Continued)

OTHER PUBLICATIONS

Allaire et al. (1997) Ann Thorac Surg 63(2):582-91.
Andrews et al. (1993). "Report of the AVMA panel on Euthanasia." Journal of the American Veterinary Association, 202(2): 229-249.
Auwerx, "The Human Leukemia-Cell Line, Thp-1-a Multifaceted Model for the Study of Monocyte-Macrophage Differentiation," Experientia, 1991, 47, (1), 22-31.
Brennan et al., "Expression in Chronic Inflammatory Disease," British Medical Bulletin, 1995, 51(2), 368-384.
Brophy et al. (1998) J Reprod Fertil 114(2):351-355.
Butler et al., "Use of organotypic coculture to study keloid biology," Am J Surg, 195(2): 144-148, Feb. 2008.
Calderon et al., "Increased proliferation in keloid fibroblasts wounded in vitro," J Surg Res, vol. 61, pp. 343-347, Mar. 1996.
Carpino et al., 1972, J. Org. Chem., 37: 3403-3409.

(Continued)

*Primary Examiner* — Karlheinz R Skowronek
*Assistant Examiner* — Roy Teller
(74) *Attorney, Agent, or Firm* — Chiesa Shahinian & Giantomasi PC

(57) ABSTRACT

The described invention provides kinase inhibiting compositions containing a therapeutic amount of a therapeutic inhibitor peptide that inhibits at least one kinase enzyme, methods for treating an inflammatory disorder whose pathophysiology comprises inflammatory cytokine expression, and methods for treating an inflammatory disorder whose pathophysiology comprises inflammatory cytokine expression using the kinase inhibiting compositions.

37 Claims, 11 Drawing Sheets

(56) References Cited

FOREIGN PATENT DOCUMENTS

| WO | WO 02/083933 | | 10/2002 |
|---|---|---|---|
| WO | WO 03/018758 | | 3/2003 |
| WO | WO 03-076333 | | 9/2003 |
| WO | 2004012660 A2 | | 2/2004 |
| WO | WO 2004/075914 | | 9/2004 |
| WO | WO 2004/110337 | | 12/2004 |
| WO | WO 2005/037236 | | 4/2005 |
| WO | WO 2005/114221 | | 12/2005 |
| WO | 2006053315 | | 5/2006 |
| WO | WO 2006/071456 | * | 7/2006 |
| WO | WO 2007/053512 | | 5/2007 |
| WO | WO 2008/008772 | | 1/2008 |
| WO | WO 2008/085191 | | 7/2008 |
| WO | WO 2009/021137 | | 2/2009 |
| WO | WO 2009/123759 | | 10/2009 |
| WO | WO 2010/065206 | | 6/2010 |
| WO | WO 2010/068692 | | 6/2010 |
| WO | WO 2011/017132 | | 2/2011 |

OTHER PUBLICATIONS

Carroll et al., "Triamcinolone stimulates bFGF production and inhibits TGF-beta 1 production by human dermal fibroblasts," Dermato Surg, vol. 28, pp. 704-709, Aug. 2002.
Chiu et al., "Photodynamic therapy on keloid fibroblasts in tissue-engineered keratinocyte-fibroblast co-culture," Lasers Surg Med, vol. 37, pp. 231-244, Sep. 2005.
Coumans et al. (2001). "Axonal regeneration and functional recovery after complete spinal cord transection in rats by delayed treatment with transplants and neurotrophins." The Journal of Neuroscience, 21(23): 9334-9344.
Dalkowski et al., "Cryotherapy modifies synthetic activity and differentiation of keloidal fibroblasts in vitro," Exp Dermatol, vol. 12, pp. 673-681, Oct. 2003.
Davies et al. (2000) Biochem J 351(Pt 1):95-105.
DeGrado et al. (1999) Annual Review of Biochemistry 68:779-819.
Dreiza et al., "Transducible heat shock protein 20 phosphopeptide alters cytoskeletal dynamics," FASEB J, 19: 261-263: 2004.
Duncan et al. (1999) FASEB J 13(13): 1774-86.
Fawell et al., Proc Nall Acad Sci USA, 1994, 91(2): 664-668.
Feldmann et al., "The role of cytokines in the pathogenesis of rheumatoid arthritis," Rheumatology, 1999, 38, 3-7.
Fields et al., 1990, Int. J. Pept. Protein Res., 35: 161-214.
Firestein et al., "How important are T cells in chronic rheumatoid synovitis? II. T cell-independent mechanisms from beginning to end," Arthritis and Rheumatism 2002, 46, (2), 298-308.
Frankel et al., Cell, 55(6): 1189-1193, 1988.
Fuchs et al. (2000) Am J Physiol Regul Integr Comp Physiol 279(2): R492-8.
Gaestel, Nat. Rev. Mol. Cell. Biol. 7, 120-130, 2006.
Gerthoffer et al. (2001) J Appl Physiol 91:963-972, 2001.
Green et al., Cell, 1988, 55(60: 1179-1188.
Hayess et al., "Effect of protein kinase inhibitors on activity of mammalian small heat-shock protein (HSP25) kinase", *Biochemical Pharmacology*, May 9, 1997, vol. 53, No. 9, 1239-1247.
Hedges et al., J Biol. Chem. 274, 24211-24219, 1999.
Hegen et al., "MAPKAP kinase 2-deficient mice are resistant to collagen-induced arthritis," Journal of Immunology 2006, 177(3), 1913-1917.
Hirano et al., Journal of Surgical Research 102, 77-84, 2002.
Hong et al., "Growth of keloid-producing fibroblasts in commercially available serum-free media," Otolaryngol Head Neck Surg, vol. 121, pp. 469-73, Oct. 1999.
Jenkins et al., "The pathogenesis of rheumatoid arthritis: A guide to therapy," American Journal of the Medical Sciences, 2002, 323(4), 171-180.
Kent et al. (2004) Ann Vasc Surg 18(2): 135-7.
Koch et al., "Serum-free keloid fibroblast cell culture: an in vitro model for the study of aberrant wound healing," in Plast Reconstr Surg., vol. 99, 1997, pp. 1094-1098.
Kossi et al., "Different metabolism of hexose sugars and sucrose in wound fluid and in. fibroblast cultures derived from granulation tissue, hypertrophic scar and keloid," Pathobiology; vol. 68, pp. 29-35, Jan.-Feb. 2000.
Kotlyarov et al., "MAPKAP kinase 2 is essential for LPS-induced TNF-alpha biosynthesis," Nature Cell Biology, 1999, 1(2).
Kumar et al., "p38 map kinases: Key signaling molecules as therapeutic targets for inflammatory diseases," Nature Reviews Drug Discovery, 2003, 2, (9), 717-726.
Lavoie et al., J Biol. Chem. 268, 24210-24214, 1993.
Lavoie et al., Mol Cell Biol. 15: 505-516, 1995.
Macomson et al. (2002) Neurosurgery 51(1): 204-10; discussion 210-1.
Mann et al. (1999) Lancet 354(9189): 1493-8.
Matsuoka et al., "Ultrastructural characteristics of keloid fibroblasts," Am J Dermatopathol, vol. 10, pp. 505-508, Dec. 1988.
McLemore et al. (2005) J Am Coll Surg 201(1): 30-6.
Neidigh et al. (2002) Nature Structural Biology 9(6): 425-430.
Pincus et al., "What is the Natural-History of Rheumatoid-Arthritis," Rheumatic Disease Clinics of North America, 1993, 19, (1), 123-151.
Pinol et al., "Effect of minoxidil on DNA synthesis in cultured fibroblasts from healthy skin or keloids," Med Cutan Ibero Lat Am, vol. 18, pp. 13-17, 1990.
Podolin et al., "Attenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory cytokines and antigen-induced T cell proliferation," Journal of Pharmacology and Experimental Therapeutics, 2005, 312, (1), 373-381.
Polo et al., "Effect of TGF-beta2 on proliferative scar fibroblast cell kinetics," Ann Plast Surg, vol. 43, pp. 185-190, Aug. 1999.
Powell et al. (2003) Molecular and Cellular Biology, 23(15) 5376-5387.
Ross et al., "High-content screening analysis of the p38 pathway: Profiling of structurally related p38 alpha kinase inhibitors using cell-based assays," Assay and Drug Development Technologies, 2006, 4, (4), 397-409.
Russel et al., "The effect of histamine on the growth of cultured fibroblasts isolated from normal and keloid tissue," J Cell Physiol, vol. 93, pp. 389-393, Dec. 1977.
Sahara et al., "Suppression of in vitro proliferative scar fibroblast contraction by interferon alfa-2b," Wound Repair Regen, vol. 1, pp. 22-27, Jan. 1993.
Saklatvala, "The p38 MAP kinase pathway as a therapeutic target in inflammatory disease," Current Opinion in Pharmacology, 2004, 4, (4), 372-377.
Schwarze et al., Science, 1999, 285(54339: 1569-1572.
Seal et al., Biomacromolecules, 2003, 4: 1572-1582.
Sestier et al., "In vitro toxicity of magnetic fluids evaluated for macrophage cell lines," Journal of Magnetism and Magnetic Materials, 2002, 252, (1-3), 403-405.
Silver et al., "Regeneration beyond the glial scar," Nature Reviews Neuroscience, 2004. 5(2): p. 146-156.
Takemura et al., "Evaluation of a human monocytic cell line THP-1 model for assay of the intracellular activities of antimicrobial agents against Legionella pneumophila," Journal of Antimicrobial Chemotherapy, 2000, 46, (4), 589-594.
Tessier et al. (2004) J Vasc Surg 40(1): 106-14.
Tyagi et al., J Biol Chem., 2001, 276(5): 3254-3261.
Verlardo et al., "Patterns of Gene Expression Reveal a Temporally Orchestrated Wound Healing Response in the Injured Spinal Cord," J. Neurosci.: 2004. 24(39): p. 8562-8576.
Vincent et al., "Human Skin Keloid Fibroblasts Display Bioenergetics of Cancer Cells," J Invest Dermatol, 128(3): 702-709, Mar. 2008.
Wang et al., "Construction of animal models of keloid by tissue engineering," Di Yi Jun Yi Da Xue Xue Bao, vol. 25, pp. 815-819, 832, Jul. 2005.
Woerly et al. (2001). "Spinal cord reconstruction using Neurogel™ Implants and functional recovery after chronic injury." Journal of Neuroscience Research, 66: 1187-1197.
Xia et al., "Increased CCN2 transcription in keloid fibroblasts requires cooperativity between AP-I and SMAD binding sites," Ann Surg, vol. 246, pp. 886-895, Nov. 2007.

(56) References Cited

OTHER PUBLICATIONS

Xia et al., "P38 MAP kinase mediates transforming growth factor-beta2 transcription in human keloid fibroblasts," Am J Physiol Regul Integr Comp Physiol, vol. 290, pp. R501-R508, Mar. 2006.
Xu et al., Oncogene 25, 2987-2998, 2006.
Yamanishi et al., "Regulation of joint destruction and inflammation by p53 in collagen-induced arthritis," American Journal of Pathology 2002, 160, (1), 123-130.
Yamboliev et al., Am. J Physiol. Heart Circ Physiol., 278, H1899-1907, 2000.
Yang et al., "Establishment of an animal model of human hyperplastic scar in nude mice," Zhonghua Shao Shang Za Zhi, vol. 20, pp. 82-84, Apr. 2004.
Yang et al., "Early expression and cellular localization of proinflammatory cytokines interleukin-1 beta, interleukin-6, and tumor necrosis factor-alpha in human traumatic spinal cord injury," Spine, 2004. 29(9): p. 966-71.
Zong, X., et al., "Prevention of postsurgery-induced abdominal adhesions by electrospun bioabsorable nanofibrous poly(lactide-co-clucolide)-based membranes," Am. Surg., 2004, 240(5): p. 910-5.
Colomer, Sub-Cellular Biochemistry, 2007, 45: 169-214.
Abergel et al., "Biochemical composition of the connective tissue in keloids and analysis of collagen metabolism in keloid fibroblast cultures," J Invest Dermatol, vol. 84, pp. 384-390, May 1985.
Achari et al., 1997, J Polym Sci A: Polym Chem, 35: 2513-2520.
Altschul et al., Nucleic Acids Res. 25:3389-3402 (1997).
Amano et al., "Formation of Actin Stress Fibers and Focal Adhesions Enhanced by RhoKinase", Science, Feb. 28, 1997, vol. 275, No. 5304, 1308-1311.
Andrew et al., "Spinothalamic lamina I neurons selectively sensitive to histamine: a central neural pathway for itch," Nature Neuroscience, 2001.4(1): p. 72-77.
Bareyre et al., "Inflammation, degeneration and regeneration in the injured spinal cord: insights from DNA microarrays," Trends Neurosci, 2003, 26(10): p. 555-63.
Barone et al., "Inhibition of p38Mitogen-Activated Protein Kinase Provides Neuroprotection in Cerebral Focal Ischemia", Med Res. Rev., 2001, vol. 21, No. 2, 129-145.
Beutler, 1999; J. Rheumatol., 26:16-21.
Buckenmaier, C.C., $3^{rd}$, et al., "Comparison of antiadhesive treatments using an objective rat model," Am. Surg., 1999, 65(3): 274-82.
Choi, et al., 2005, Angewandte Chemie, 44(41): 6685-6689.
Claverie et al., Comput. Chem., 17:191-201 (1993).
Clowes et al. (1991) J Vasc Surg, 13(6):885-91.
Corpet, et al., Nucleic Acids Research, 16:10881-90 (1988).
DeMarzo et al., "Prostate stem cell compartments: expression of the cell cycle inhibitor p27Kip1 in normal, hyperplastic, and neoplastic cells", Am. J. Pathol., Sep. 1998, vol. 153, No. 3, 911-919.
Dreiza et al. (2005) FASEB J 19(2):261-3.
Feldmann et al., "Role of cytokines in rheumatoid arthritis," Annual Review of Immunology, 1996, 14, 397-440.
Fisher et al., 1994, Macromol Chem Phys, 195: 679-687.
Fragonas et al., Aricular cartilage repair in rabbits by using suspensions of allogenic chondrocytes in alginate, Biomaterials, 2000, 21(8):795-801.
Fuchs et al. (1997) J Hypertens 15(3): 301-307.
Gaestel et al., "Protein kinases as small molecule inhibitor targets in inflammation," Current Medicinal Chemistry, 2007, 14 (21): 2214-2234.
Gu et al., 2002, J Appl Poly Sci, 86: 3412-3419.
Haapasalo et al., "Truncated trkB.T1 is dominant negative inhibitor of trkB.TK+-mediated cell survival", Biochem Biophys Res Commun, Feb. 9, 2001, vol. 280, No. 5, 1352-1358 (Abstract only).
Hanasono et al., "Autocrine growth factor production by fetal, keloid, and normal dermal fibroblasts," Arch Facial Plast Surg, vol. 5, pp. 26-30, Jan.-Feb. 2003.
Henikoff et al. (1989) Proc. Natl. Acad. Sci. USA 89:10915).
Higgins et al., CABIOS, 5:151-153 (1989).
Higgins et al., Gene, 73:237-244 (1988).

Ho et al., "Synthetic Protein Transduction Domains: Enhanced Transduction Potential in Vitro and in Vivo," Cancer Research, 2001, 61: 474-477.
Hruby, V. J. (2002) Nat Rev Drug Discov 1(11): 847-58.
Huang, et al., Computer Applications in the Biosciences 8:155-65 (1992).
Iwasaki et al., "Effect of transforming growth factor beta 1 on spinal motor neurons after axotomy," J Neurol Sci, 1997, 147(1): 9-12.
Jacovella, Long-lasting results with hydroxylapatite (Radiesse) facial filler, Plastic and Reconstructive Surgery, 2006, 118(3S):15S-21S.
Jobanputra et al., Colorectal Dis. Oct. 2007; 9 Suppl 2: 54-9.
Johnson et al. (2004) Nature Biotech 22(9):1093-1094.
Karlin et al., Proc. Natl. Acad. Sci. USA 90:5873-5787 (1993).
Knoepp et al. (2000) J Vasc Surg 31:343-353.
Koonin et al., "Origin and evolution of eukaryotic apoptosis: the bacterial connection", Cell Death Differ, Apr. 2002, vol. 9, No. 4, 394-404.
Kwon et al., "The cdk2 Binding Domain of p27Kip Correlates with the Inhibition of the Kinase Activity of cdk2/Cyclin Complexes", Biochem Biophys Res Comm, 1996, vol. 220, 703-709.
Langer, 1990 Science 249, 1527-1533.
Liu et al., De novo design, synthesis, and characterization of antimicrobial beta-peptides, J Am Chem Soc, 2001, 123(31): 7553-7559.
LoGerfo et al. (1984) Arch Surg 119:1212-1214.
Lopes et al., "Inhibition of HSP27 phosphorylation by a cell-permeant MAPKAP Kinase 2 inhibitor", *Biochemical and Biophysical Research Communcations*, May 8, 2009, vol. 382, No. 3, 535-539.
Marijnissen et al., Tissue-engineered cartilage using serially passaged articular chondrocytes. Chondrocytes in alginate, combined in vivo with a synthetic (E210) or biologic degradable carrier (DBM), Biomaterials, 2000, 21(6):571-580.
McCormack et al., "The effect of copper tripeptide and tretinoin on growth factor production in a serum-free fibroblast model," Arch Facial Plast Surg, vol. 3, pp. 28-32, Jan.-Mar. 2001.
Merrifield, 1963, J. Am. Chem. Soc., 85: 2149-2154.
Meyers et al., Computer Applic. Biol. Sci., 4:11-17 (1988).
Mosse et al. (1985) Lab Invest 53(5): 556-62.
Needleman et al., J. Mol. Biol., 48: 443 (1970).
Pearson et al., Methods in Molecular Biology, 24: 307-331 (1994).
Pearson et al., Proc. Natl. Acad. Sci., 85: 2444 (1988).
Pineau et al., Proinflaminatory cytokine synthesis in the injured mouse spinal cord: multiphasic expression pattern and identification of the cell types involved,: J Comp Neurol, 2007, 500(2): p. 267-285.
Ridley et al., "Actions of 11-1 are Selectively Controlled by P38 Mitogen-Activated Protein Kinase: regulation of prostaglandin H synthase-2, metalloproteinases, and IL-6 at different levels", *J. Immunol.*, 1997, vol. 158, 3165-3173.
Sawhney et al., Macromolecules (1993) 26, 581-587.
Schenk et al., Signal perception and transduction: the role of protein kinases, Biochemica et Biophyica Acta, 1999, vol. 1449, 1-24.
Shi et al. (2002) Biol Chem 383:1519-1536, 2002.
Smith and Waterman, Adv. Appl. Math., 2: 482 (1981).
Sousa et al. (2007) J Cell Biochem 100(6):1581-1592.
Stokoe, Biochem. J., 1993, 296 (Pt 3): 843-849.
Tanaka et al., 1976, Bulletin of the Chemical Society of Japan, 49(10): 2821-2823.
Tang et al., Synthesis of urea oligomers and their antibacterial activity, Chem Commun, 2005, 1537-1539.
Terashima et al. (2002) J Am Coll Cardiol 39:228A.
Tew et al., De novo design of biomimetic antimicrobial polymers, PNAS, 2002, 99(8): 5110-5114.
Tapash et al., Transdermal and Topical Drug Delivery, pp. 249-297 (1997).
Vassalli, 1992, Annu. Rev. Immunol., 10:411-452.
Violette et al., Mimicking helical antibacterial peptides with nonpeptidic folding oligomers, Chemistry and Biology, 2006, 13(5): 531-538.
Wang et al., "p27Kip1 overexpression causes apoptotic death in mammalian cells", Oncogene, Dec. 11, 1997, vol. 15, No. 24, 2991-2997.

(56) References Cited

OTHER PUBLICATIONS

Ward et al., "Design of a bioactive cell-penetrating peptide: when a transduction domain does more than transduce", *Journal of Peptide Science*, Oct. 2009, vol. 15, No. 10, 668-674.
Weibel et al., Am. J. Surg. 1973; 126: 345-53.
Wooten et al., Comput. Chem., 17: 149-163 (1993).
Worm et al., "Aberrant p27Kip1 promoter methylation in malignant melanoma", Oncogene, Oct. 19, 2000, vol. 19, No. 44, 5111-5115.
Biomol International (online), Kinase Inhibitors. 2006, retrieved from http://www.biomol.com/Online_Catalog/Online_Catalog/Products/36/?search=&mode=product&lastSort=&all=true&categoryId=714. (catalog availble upon request).
Biomol International (online), Kinases. 2006, retrieved from http://www.biomol.com/Online_Catalog/Online_Catalog/Products/36/?search=&mode=product&lastSort=&all=true&categoryId=713. (catalog available upon request).
Carroll et al., "Heparin stimulates production of bFGF and TGF-beta 1 by human normal, keloid, and fetal dermal fibroblasts," Med Sci Monit, vol. 9, pp. BR97-BR108, Mar. 2003.
Brugnano et al., Journal of Controlled Release, (2011), 155: 128-133.
Schindler et al., Examination of the kinetic mechanism of mitogen-activated protein kinase activated protein kinase-2, Biochimica et Biophysica Acta, Jul. 29, 2002, 1598(1-2): 88-97.
Burgess et al., J of Cell Bio., 1990, 111: 2129-2138.
Bowie et al., Science, 1990, 247: 1306-1310.
Pawson et al., Science, 2003, 300: 445-452.
Zhongshu Song et al., "Fusarin C biosynthesis in Fusarium moniliforme and Fusarium venenatum," *Chembiochem*, 2004, 5(9): 1196-1203.
Morrison et al., "Combinatorial alanine-scanning," Current Opinion in Chemical Biology, 2001, 5:302-307.
Del Gaizo et al. A Novel TAT-Mitochondrial Signal Sequence Fusion Protein is Processed, Stays in Mitochondria, and Crosses the Placenta, Molecular Therapy, 2003, 7(6):720-730.
Yu, Pey-Jen et al; "Vascular injury and modulation of MAPKs: A targeted approach to therapy of restenosis." Cell. Signal. (2007) 19 p. 1359-1371.
Tucker, Erik I. et al; "Prevention of vascular graft occlusion and thrombus-associated thrombin generation by inhibition of factor XI." Blood (2009) 113(4) p. 936-944.

Babapulle, Mohan N. et al; "A hierarchial bayesian meta analysis of randomized clinical trials of drug eluting stents." Lancet (2004) 364 p. 583-91.
Cyrus, Tillmann et al; "Effect of low dose aspirin on vascular inflammation, plaque stability, and atherogenesis in low density lipoprotein receptor deficient mice." Circulation (2002) 106 p. 1282-1287.
Dinarello, C. A.; "The IL-1 family and inflammatory diseases." Clin. Exp. Rheumatol. (2002) 20 (suppl. 27) p. S1-S13.
Tourneau Christophe Le et al; "Dose escalation methods in phase I cancer clinical trials." J. Natl. Cancer. Inst. (2009) 101 (10) p. 708-720, publication date May 20, 2009.
Schneider et al., 1998, In Vivo Evaluation of hsp27 as an Inhibitor of Actin Polymerization: Hsp27 Limits Actin Stress Fiber and Focal Adhesion Formation After Heat Shock, Journal of Cellular Physiology, 177: 575-584.
Beck et al., 2000, Molecular chaperones in the kidney: distribution, putative roles, and regulation, Am J Physiol Renal Physiol, 279: 203-215.
Keezer et al., Angiogenesis Inhibitors Target the Endothelial Cell Cytoskeleton through Altered Regulation of Heat Shock Protein 27 and Cofilin, Cancer Res, 63: 6405-6412.
Chinese Office Action dated May 18, 2015 in corresponding Chinese Application No. 200980156800.X.
Tietz et al., "Gene deletion of MK2 inhibits TNF-α and IL-6 and protects against cerulein-induced pancreatitis," Am J Physiol Gastrointest Liver Physiol 290, Jan. 19, 2006, G1298-G1306.
Japanese Decision of Final Rejection dated Oct. 21, 2014 in corresponding Japanese Application No. 2011-540872.
Xin Su et al.,"Post-transcriptional regulation of TNF-induced expression of ICAM-1 and IL-8 in human lung microvascular endothelial cells: An obligatory role for the p38 MAPK-MK2 pathway dissociated with HSP27", Biochimica Et Biophysica Acta, Apr. 30, 2008, vol. 1783, No. 9, p. 1623-1631.
Tobias Thomas et al, "MAPKAP kinase 2-deficiency prevents neurons from cell deaht by reducing neuroinflammation—relevance in a mouse model of Parkinson's disease", Journal of Neurochemistry, Jun. 2008, vol. 105, No. 5, p. 2039-2052.
Jianzhong Zhu et al.,"MAPK-activated Protein Kinase 2 Differentially Regulates Plasmodium falciparum Glycosylphosphatidylinositolinduced Production of Tumor Necrosis Factor- and Interleukin-12 in Macrophages", Journal of Biological Chemistry, Apr. 9, 2009, vol. 284, No. 23, p. 15750-15761.

* cited by examiner

CELL-PERMEANT PEPTIDE-BASED INHIBITOR OF KINASES

CROSS REFERENCES

This application claims the benefit of priority to U.S. provisional application 61/121,396, filed Dec. 10, 2008, incorporated herein by reference in its entirety.

STATEMENT OF GOVERNMENT FUNDING

The described invention was made with government support under Grant K25HL074968 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy is named 12634476 (CRF).txt and is 18,424 bytes in size.

FIELD OF THE INVENTION

The described invention relates to cell biology, cell-permeant peptides, cell-permeant peptide compositions, and methods of use thereof, and methods of protein engineering.

BACKGROUND

The three-dimensional conformation of a protein molecule is determined by its amino acid sequence, and the details of a protein's conformation determine its chemistry.

A protein generally consists of a polypeptide backbone with attached side chains. The sequence of the chemically different side chains of the amino acid makes each protein distinct. The folded structure of a protein is stabilized by noncovalent interactions (e.g., hydrogen bonds, ionic bonds, and van der Waals attractions) that form between different parts of the polypeptide chain. one part of the chain and another. The stability of each folded shape is determined by the combined strength of large numbers of such noncovalent bonds.

Each protein has four levels of structural organization. The amino acid sequence is the primary structure of the protein. The secondary structure is defined by patterns of hydrogen bonds between backbone amide and carboxyl groups without consideration of sidechain-mainchain and sidechain-sidechain hydrogen bond (e.g. α helix, β-sheet). The tertiary structure, the full three-dimensional organization of a polypeptide chain, is the manner in which the sheets and helices of the secondary structure of a protein fold on themselves to define the three-dimensional structure. Quaternary structure refers to the complete structure of a protein molecule formed as a complex of more than one polypeptide chain.

Protein domains are structural units that fold more or less independently of each other to form globular compact structures. A domain usually contains between about 40 and about 350 amino acids, and is the modular unit from which many larger proteins are constructed. The different domains of a protein often are associated with different functions. The final folded structure, or conformation, adopted by any polypeptide chain generally is the one in which the free energy is minimized.

1. Kinases

Kinases are a ubiquitous group of enzymes that catalyze the phosphoryl transfer reaction from a phosphate donor (usually adenosine-5'-triphosphate (ATP)) to a receptor substrate. Although all kinases catalyze essentially the same phosphoryl transfer reaction, they display remarkable diversity in their substrate specificity, structure, and the pathways in which they participate. A recent classification of all available kinase sequences (approximately 60,000 sequences) indicates kinases can be grouped into 25 families of homologous proteins. These kinase families are further assembled into 12 fold groups based on similarity of structural fold. Further, 22 of the 25 families (approximately 98.8% of all sequences) belong to 10 fold groups for which the structural fold is known. Of the other 3 families, polyphosphate kinase forms a distinct fold group, and the 2 remaining families are both integral membrane kinases and comprise the final fold group. These fold groups not only include some of the most widely spread protein folds, such as Rossmann-like fold (three or more parallel beta strands linked by two alpha helices in the topological order beta-alpha-beta-alpha-beta), ferredoxin-like fold (a common α+β protein fold with a signature βαββαβ secondary structure along its backbone), TIM-barrel fold (meaning a conserved protein fold consisting of eight α-helices and eight parallel β-strands that alternate along the peptide backbone), and antiparallel β-barrel fold (a beta barrel is a large beta-sheet that twists and coils to form a closed structure in which the first strand is hydrogen bonded to the last), but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein SIT-Y kinase, atypical protein kinase, lipid kinase, and ATP grasp enzymes and further comprise the protein SIT-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH₂)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor] kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylinositol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences) which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises the P-loop kinase family (7,732 sequences). These include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylylsulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy)nucleoside-phosphate kinase (EC 2.7.4.13); cytidylate kinase (EC 2.7.4.14); and uridylate kinase (EC 2.7.4.-). Group II further comprises the phosphoenolpyruvate carboxykinase family (815 sequences). These enzymes include protein kinase (HPr kinase/phosphatase) (EC 2.7.1.37); phosphoenolpyruvate carboxykinase (GTP) (EC 4.1.1.32); and phosphoenolpyruvate carboxykinase (ATP) (EC 4.1.1.49). Group II further comprises the phosphoglycerate kinase (1,351 sequences) family. These enzymes include phosphoglycerate kinase (EC 2.7.2.3) and phosphoglycerate kinase (GTP) (EC 2.7.2.10). Group II further comprises the aspartokinase family (2,171 sequences). These enzymes include carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4.-). Group II further comprises the phosphofructokinase-like kinase family (1,998 sequences). These enzymes include 6-phosphofructokinase (EC 2.7.1.1 1); NAD(+) kinase (EC 2.7.1.23); I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138). Group II further comprises the ribokinase-like family (2,722 sequences). These enzymes include: glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7). Group II further comprises the thiamin pyrophosphokinase family (175 sequences) which includes thiamin pyrophosphokinase (EC 2.7.6.2). Group II further comprises the glycerate kinase family (107 sequences) which includes glycerate kinase ((EC 2.7.1.31).

Group III kinases (10,973 sequences) comprise the ferredoxin-like fold kinases. Group III further comprises the nucleoside-diphosphate kinase family (923 sequences). These enzymes include nucleoside-diphosphate kinase (EC 2.7.4.6). Group III further comprises the HPPK kinase family (609 sequences). These enzymes include 2-amino-4-hydroxy-6-hydroxymethyldihydropteridine pyrophosphokinase (EC 2.7.6.3). Group III further comprises the guanido kinase family (324 sequences). These enzymes include guanidoacetate kinase (EC 2.7.3.1); creatine kinase (EC 2.7.3.2); arginine kinase (EC 2.7.3.3); and lombricine kinase (EC 2.7.3.5). Group III further comprises the histidine kinase family (9,117 sequences). These enzymes include protein kinase (histidine kinase) (EC 2.7.1.37); [pyruvate dehydrogenase (lipoamide)] kinase (EC 2.7.1.99); and [3-methyl-2-oxybutanoate dehydrogenase(lipoamide)] kinase (EC 2.7.1.115).

Group IV kinases (2,768 sequences) incorporate ribonuclease H-like kinases. These enzymes include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.-).

Group V kinases (1,119 sequences) incorporate TIM β/α-barrel kinases. These enzymes include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2)

Group VII kinases (1,843 sequences) incorporate AIR synthetase-like kinases. These enzymes include thiamine-phosphate kinase (EC 2.7.4.16) and selenide, water dikinase (EC 2.7.9.3).

Group VIII kinases (565 sequences) incorporate riboflavin kinases (565 sequences). These enzymes include riboflavin kinase (EC 2.7.1.26).

Group IX kinases (197 sequences) incorporate dihydroxyacetone kinases. These enzymes include glycerone kinase (EC 2.7.1.29).

Group X kinases (148 sequences) incorporate putative glycerate kinases. These enzymes include glycerate kinase (EC 2.7.1.31).

Group XI kinases (446 sequences) incorporate polyphosphate kinases. These enzymes include polyphosphate kinases (EC 2.7.4.1).

Group XII kinases (263 sequences) incorporate integral membrane kinases, Group XII comprises the dolichol kinase family. These enzymes include dolichol kinases (EC 2.7.1.108), Group XII further comprises the undecaprenol kinase family. These enzymes include undecaprenol kinases (EC 2.7.1.66).

Kinases play indispensable roles in numerous cellular metabolic and signaling pathways, and they are among the best-studied enzymes at the structural, biochemical, and cellular levels. Despite the fact that all kinases use the same phosphate donor (in most cases, ATP) and catalyze apparently the same phosphoryl transfer reaction, they display remarkable diversity in their structural folds and substrate recognition mechanisms. This is probably due largely to the extraordinary diverse nature of the structures and properties of their substrates.

2. Mitogen-activated Protein Kinase-activated Protein Kinases (MK2 and MK3)

Different groups of MAPK-activated protein kinases (MAP-KAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAP-KAPKs: MK2, MK3 (also known as 3 pK), and MK5 (also designated PRAK). Mitogen-activated protein kinase-activated protein kinase 2 (also referred to as "MAPKAPK2", "MAPKAP-K2", "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The mk2 gene encodes two alternatively spliced transcripts of 370 amino acids (MK2A) and 400 amino acids (MK2B). The mk3 gene encodes one transcript of 382 amino acids. The MK2-and MK3 proteins are highly homologous, yet MK2A possesses a shorter C-terminal region. The C-terminus of MK2B contains a functional bipartite nuclear localization sequence (NLS) (Lys-Lys-Xaa$_{10}$-Lys-Arg-Arg-Lys-Lys) [SEQ ID NO: 45]that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys) [SEQ ID NO: 46]that studies have shown to mediate the specific interaction of MK2B and MK3 with p38α, and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. Recent studies suggest that this domain is involved in MK2-mediated cell migration.

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active NLS and a phosphorylation-regulated NES.

MK2 and MK3 appear to be expressed ubiquitously, with predominant expression in the heart, in skeletal muscle, and in kidney tissues.

2.1. Activation

Various activators of p38α and p38β potently stimulate MK2 and MK3 activity. p38 mediates the in vitro and in vivo phosphorylation of MK2 on four praline-directed sites: Thr25, Thr222, Ser272, and Thr334. Of these sites, only Thr25 is not conserved in MK3. Without being limited by theory, while the function of phosphorylated Thr25 in unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export.

Studies have shown that, while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels.

2.2. Substrates and Functions

MK2 shares many substrates with MK3. Both enzymes have comparable substrate preferences and phosphorylate peptide substrates with similar kinetic constants. The minimum sequence required for efficient phosphorylation by MK2 was found to be Hyd-Xaa-Arg-Xaa-Xaa-pSer/Thr, where Hyd is a bulky hydrophobic residue.

Experimental evidence supports a role for p38 in the regulation of cytokine biosynthesis and cell migration. The targeted deletion of the mk2 gene in mice suggested that although p38 mediates the activation of many similar kinases, MK2 seems to be the key kinase responsible for these p38-dependent biological processes. Loss of MK2 leads (i) to a defect in lipopolysaccharide (LPS)-induced synthesis of cytokines such as tumor necrosis factor alpha (TNFα), interleukin-6 (IL-6), and gamma interferon (IFN-γ) and (ii) to changes in the migration of mouse embryonic fibroblasts, smooth muscle cells, and neutrophils. Consistent with a role for MK2 in inflammatory responses, MK2-deficient mice show increased susceptibility to *Listeria monocytogenes* infection and reduced inflammation-mediated neuronal death following focal ischemia. Since the levels of p38 protein also are reduced significantly in MK2-deficient cells, it was necessary to distinguish whether these phenotypes were due solely to the loss of MK2. To achieve this, MK2 mutants were expressed in MK2-deficient cells, and the results indicated that the catalytic activity of MK2 was not necessary to restore p38 levels but was required to regulate cytokine biosynthesis.

2.3. Regulation of mRNA Translation.

Studies have shown that MK2 increases TNFα production by increasing the rate of translation of its mRNA; no significant reductions in the transcription, processing, and shedding of TNFα could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) AO, tristetraprolin, the poly(A)-binding protein PABP1, and HuR (a ubiquitously expressed member of the elav (embryonic-lethal abnormal visual in *Drospholia melanogaster*) family of RNA-binding protein). These substrates are known to bind or copurify with mRNAs that contain AU-rich elements in the 3' untranslated region, suggesting that MK2 may regulate the stability of AU-rich mRNAs such as TNFα. It currently is unknown whether MK3 plays similar functions, but LPS treatment of MK2-deficient fibroblasts completely abolished hnRNP AO phosphorylation, suggesting that MK3 is not able to compensate for the loss of MK2.

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation.

2.4. Transcriptional Regulation by MK2 and MK3.

Nuclear MK2, similar to many MKs, contributes to the phosphorylation of cAMP response element binding (CREB), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation.

2.5. Other Targets of MK2 and MK3.

Several other MK2 and MK3 substrates also have been identified, reflective of the diverse functions of MK2 and MK3 in several biological processes. The scaffolding protein 14-3-3ζ is a physiological MK2 substrate. Studies indicate 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3ζ.

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process. Further studies have shown that the small heat shock protein HSP27, lymphocyte-specific protein LSP-1, and vimentin are phosphorylated by MK2. HSP27 is of particular interest because it forms large oligomers which may act as molecular chaperones and protect cells from heat shock and oxidative stress. Upon phosphorylation, HSP27 loses its ability to form large oligomers and is unable to block actin polymerization, suggesting that MK2-mediated phosphorylation of HSP27 serves a homeostatic function aimed at regulating actin dynamics that would otherwise be destabilized during stress. MK3 also was shown to phosphorylate HSP27 in vitro and in vivo, but its role during stressful conditions has not yet been elucidated.

MK2 and MK3 also may phosphorylate 5-lipoxygenase. 5-lipoxygenase catalyzes the initial steps in the formation of the inflammatory mediators leukotrienes. Tyrosine hydroxylase, glycogen synthase, and Akt also were shown to be phosphorylated by MK2. Finally, MK2 phosphorylates the tumor suppressor protein tuberin on Ser1210, creating a docking site for 14-3-3. Tuberin and hamartin normally form a functional complex that negatively regulates cell growth by antagonizing mTOR-dependent signaling, suggesting that p38-mediated activation of MK2 may regulate cell growth by increasing 14-3-3 binding to tuberin.

3. Kinase Inhibition

The eukaryotic protein kinases constitute one of the largest superfamilies of homologous proteins that are related by virtue of their catalytic domains. Most related protein kinases are specific for either serine/threonine or tyrosine phosphorylation. Protein kinases play an integral role in the cellular response to extracellular stimuli. Thus, stimulation of protein kinases is considered to be one of the most common activation mechanisms in signal transduction systems. Many substrates are known to undergo phosphorylation by multiple protein kinases. A considerable amount of information on primary sequence of the catalytic domains of various protein kinases has been published. These sequences share a large number of residues involved in ATP binding, catalysis, and maintenance of structural integrity. Most protein kinases possess a well conserved 30-32 kDa catalytic domain.

Studies have attempted to identify and utilize regulatory elements of protein kinases. These regulatory elements include inhibitors, antibodies, and blocking peptides.

3.1. Inhibitors

Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically (e.g., by modifying key amino acid residues needed for enzymatic activity) so that it no longer is capable of catalyzing its reaction. In contrast, reversible inhibitors bind non-covalently and different types of inhibition are produced depending on whether these inhibitors bind the enzyme, the enzyme-substrate complex, or both.

Enzyme inhibitors often are evaluated by their specificity and potency. The term "specificity" as used in this context rein refers to the selective attachment of an inhibitor or its lack of binding to other proteins. The term "potency" as used herein refers to an inhibitor's dissociation constant, which indicates the concentration of inhibitor needed to inhibit an enzyme.

Inhibitors of protein kinases have been studied for use as a tool in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chk1), glycogen synthase kinase 3 (GSK-3), c-Jun N-terminal kinase (INK), mitogen-activated protein kinase 1 (MEK), myosin light chain kinase (MLCK), protein kinase A, Akt (protein kinase B), protein kinase C, protein kinase G, protein tyrosine kinase, Raf kinase, and Rho kinase.

3.2. Antibodies

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG$_1$, IgG$_2$, IgG$_3$, IgG$_4$) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy ($V_H$) and light ($V_\kappa$ and $V_\lambda$) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes chimeric antibodies and wholly synthetic antibodies, and fragments thereof.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants. As used herein, an epitope may be an antigenic determinant/antigen binding site on a kinase inhibiting peptide. The epitope may be primary, secondary, or tertiary-sequence related.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens The specificity of the interactions between certain antibodies and protein kinases has been studied for use in protein kinase activity regulation. Antibodies have been isolated for use with, for example, MAP kinase pathways, protein kinase A, protein kinase B, protein kinase G, serine/threonine kinases, glycogen-synthase kinase-3 (GSK-3), stress-activated protein (SAP) kinase pathways, and tyrosine kinases. Additionally, antibodies have been isolated for use with protein kinase inhibitors and protein kinase substrates.

3.3. Blocking Peptides

A peptide is a chemical compound that is composed of a chain of two or more amino acids whereby the carboxyl group of one amino acid in the chain is linked to the amino group of the other via a peptide bond. Peptides have been used inter alia in the study of protein structure and function. Synthetic peptides may be used inter alia as probes to see where protein-peptide interactions occur. Inhibitory peptides may be used inter alia in clinical research to examine the effects of peptides on the inhibition of protein kinases, cancer proteins and other disorders.

The use of several blocking peptides has been studied. For example, extracellular signal-regulated kinase (ERK), a MAPK protein kinase, is essential for cellular proliferation and differentiation. The activation of MAPKs requires a cascade mechanism whereby MAPK is phosphorylated by an upstream MAPKK (MEK) which is then, in turn phosphorylated by a third kinase MAPKKK (MEKK). The ERK inhibitory peptide functions as a MEK decoy by binding to ERK. It contains the amino-terminal 13 amino acids (GMPKKKPT-PIQLN) [SEQ ID NO: 1] of MEK1 and binds to ERK. This blocks ERK activation by MEK as ERK is unable to interact with MEK. The ERK inhibitory peptide also contains a protein transduction (PTD) sequence (DRQIKIWFQNRRMK-WKK) [SEQ ID NO: 2] derived from Antennapedia which renders the peptide cell permeable.

Other blocking peptides include autocamtide-2 related inhibitory peptide (AIP). This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an $IC_{50}$ of 100 nM ($IC_{50}$ is the concentration of an inhibitor required to obtain 50% inhibition). The AIP inhibition is non-competitive with respect to syntide-2 (CaMKII peptide substrate) and ATP but competitive with respect to autocamtide-2. The inhibition is unaffected by the presence or absence of Ca2+/calmodulin. CaMKII activity is inhibited completely by AIP (1 µM) while PKA, PKC and CaMKIV are not affected. The amino acid sequence of AIP is: KKALRRQEAVDAL (Lys-Lys-Ala-Leu-Arg-Arg-Gln-Glu-Ala-Val-Asp-Ala-Leu) [SEQ ID NO: 3].

Other blocking peptides include cell division protein kinase 5 (Cdk5) inhibitory peptide (CIP). Cdk5 phosphorylates the microtubule protein tau at Alzheimer's Disease-specific phospho-epitopes when it associates with p25. p25 is a truncated activator, which is produced from the physiological Cdk5 activator p35 upon exposure to amyloid β (A↓) peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for extracellular-regulated kinase 2 (ERK2), ERK3, p38/HOG1, protein kinase C, casein kinase II, $Ca^{2+}$/calmodulin kinase IV, casein kinase II, Cdk4, Cdk5, DNA-dependent protein kinase (DNA-PK), serine/threonine-protein kinase PAK3, phosphoinositide (PI)-3 kinase, PI-5 kinase, PSTAIRE (the cdk highly conserved sequence), ribosomal S6 kinase, GSK-4, germinal center kinase (GCK), SAPK (stress-activated protein kinase), SEK1 (stress signaling kinase), and focal adhesion kinase (FAK).

3.4. Protein Transduction Domains

Protein transduction domains (PTDs) are a class of peptides capable of penetrating the plasma membrane of mammalian cells and of transporting compounds of many types and molecular weights across the membrane. These compounds include effector molecules, such as proteins, DNA, conjugated peptides, oligonucleotides, and small particles such as liposomes. When PTDs are chemically linked or fused to other proteins, the resulting fusion proteins still are able to enter cells. Although the exact mechanism of transduction is unknown, internalization of these proteins is not believed to be receptor-mediated or transporter-mediated. PTDs are generally 10-16 amino acids in length and may be grouped according to their composition, such as, for example, peptides rich in arginine and/or lysine.

The use of PTDs capable of transporting effector molecules into cells has become increasingly attractive in the design of drugs as they promote the cellular uptake of cargo molecules. These cell-penetrating peptides, generally categorized as amphipathic (meaning having both a polar and a nonpolar end) or cationic depending on their sequence, provide a non-invasive delivery technology for macromolecules. PTDs also often are referred to as "Trojan peptides", "membrane translocating sequences", or "cell permeable proteins" (CPPs). PTDs also may be used to assist novel HSP27 kinase inhibitors to penetrate cell membranes (see U.S. application Ser. No. 11/972,459, entitled "Polypeptic Inhibitors of HSP27 Kinase and Uses Thereof," filed Jan. 10, 2008, and Ser. No. 12/188,109, entitled "Kinase Inhibitors and Uses Thereof," filed Aug. 7, 2008, incorporated by reference in their entirety herein).

3.4.1. Viral PTD Containing Proteins

The first proteins to be described as having transduction properties were of viral origin. These proteins still are the most commonly accepted models for PTD action. The HIV-1 Transactivator of Transcription (TAT) and HSV-1 VP 22 protein are the best characterized viral PTD containing proteins.

TAT (HIV-1 trans-activator gene product) is an 86-amino acid polypeptide, which acts as a powerful transcription factor of the integrated HIV-1 genome. TAT acts on the viral genome stimulating viral replication in latently infected cells. The translocation properties of the TAT protein enable it to activate quiescent infected cells and it may be involved in priming of uninfected cells for subsequent infection by regulating many cellular genes, including cytokines. The minimal PTD of TAT is the 9 amino acid protein sequence RKKRRQRRR ($TAT_{49-57}$) [SEQ ID NO: 4]. Studies utilizing a longer fragment of TAT demonstrated successful transduction of fusion proteins up to 120 kDa. The addition of multiple TAT-PTDs as well as synthetic TAT derivatives have been demonstrated to mediate membrane translocation. TAT PTD containing fusion proteins have been used as therapeutic moieties in experiments involving cancer, transporting a death-protein into cells, and disease models of neurodegenerative disorders.

VP22 is the HSV-1 tegument protein, a structural part of the HSV virion. VP22 is capable of receptor independent translocation and accumulates in the nucleus. This property of VP22 classifies the protein as a PTD containing peptide. Fusion proteins comprising full length VP22 have been translocated efficiently across the plasma membrane.

3.4.2. Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins have been described to exhibit PTD-like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain (HD). The internalization of this helix occurs at 4° C., suggesting that this process is not endocytosis dependent. Peptides up to 100 amino acids produced as fusion proteins with AntpHD penetrate cell membranes. Other homeodomains capable of translocation include Fushi tarazu (Ftz) and Engrailed (En) homeodomain. Many homeodomains share a highly conserved third helix.

3.4.3. Synthetic PTDs

Several PTD peptides have been synthesized. Many of these synthetic peptides are based on existing and well documented peptides, while others are selected for their basic residues and/or positive charge, which generally are believed to be crucial for PTD function. Synthetic peptides include, but are not limited to, PTD-4 (YARAAARQARA) [SEQ ID NO: 5]; PTD-5 (RRQRRTSKLMKR) [SEQ ID NO: 6]; MST-1 (AAVLLPVLLAAR) [SEQ ID NO: 7]; L-R9 (RRRRRRRRR) [SEQ ID NO: 8]; and Peptide 2 (SGWFRRWKK) [SEQ ID NO: 9].

3.4.4. Human PTDs

Human PTDs may circumvent potential immunogenicity issues upon introduction into a human patient. Peptides with PTD sequences include: Hoxa-5, Hox-A4, Hox-B5, Hox-B6, Hox-B7, HOX-D3, GAX, MOX-2, and FtzPTD. These proteins all share the sequence found in AntpPTD (RQIKIWFQNRRMKWKK) [SEQ ID NO: 10]. Other PTDs include Islet-1, interleukin-1β, tumor necrosis factor, and the hydrophobic sequence from Kaposi-fibroblast growth factor or FGF-4) signal peptide, which is capable of energy-, receptor-, and endocytosis-independent translocation. Unconfirmed PTDs include members of the Fibroblast Growth Factor (FGF) family.

4. Disorders: Inflammatory Disorders

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. In acute inflammation, removal of the stimulus halts the recruitment of monocytes (which become macrophages under appropriate activation) into the inflamed tissue, and existing macrophages exit the tissue via lymphatics. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity. In chronic inflammation, existing macrophages are tethered in place, and proliferation of macrophages is stimulated.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4 (IL-4), interleukin-6 (IL-6), interleukin-8 (IL-8), tumor necrosis factor (TNF), interferon-gamma, and interleukin 12 (IL-12).

Several disorders associated with inflammation underlie a variety of diseases. These include, but are not limited to, asthma, autoimmune diseases, chronic prostatitis, glomerulonephritis, inflammatory bowel disease (IBD), pelvic inflammatory disease (PID), reperfusion injury, rheumatoid arthritis, vasculitis and hypersensitivities.

Asthma

Asthma is a chronic disease involving the respiratory system in which the airways may constrict sporadically, become inflamed, and are lined with excessive amounts of mucus, often in response to one or more triggers. These triggers may include, but are not limited to, exposure to an environmental stimulants such as, but not limited to, allergens, smoke, cold or warm air, perfume, pet dander, moist air, exercise or exertion or emotional distress. The airway narrowing presents symptoms such as, but not limited to, wheezing, shortness of breath, chest tightness, coughing, dyspnea, and stridor. Elevated serum levels of IL-6 in subjects with asthma compared with normal control subjects have been implicated in the pathophysiology of bronchial asthma. Yokoyama, A. et al., Am. J. Respir. Crit. Care Med. 151(5): 1354-58 (1995). Studies also suggested, based on the observation that significant levels of TNF-α and IL-6 were detected in bronchoalveolar lavage fluid (BALF) of asthma patients, while levels of IL-1β levels in patients BALF of patients with asymptomatic asthma, activation of alveolar macrophages and T cells (Broide, D. H., et al. J. Allergy Clin. Immunol. 89(5):958-67, 1992).

Autoimmune Diseases

Ankylosing spondylitis (AS, Bechterew's disease, Bechterew syndrome, Marie Strumpell disease) is a chronic, inflammatory arthritis and autoimmune disease. It mainly affects joints in the spine and the sacroilium in the pelvis, causing eventual fusion of the spine. Studies have reported that TNF-α and IL-6 are increased in AS patients (while IL-1β levels are not) and that IL-6 is closely correlated with the activity of the disease (Gratacos, J., et al. Br. J. Rheumatol. 33(10):927-931. 1994). Symptoms of AS include, but are not limited to, chronic pain and stiffness in the lower part of the spine or sometimes the entire spine, often with pain referred to one or other buttock or the back of the thigh from the sacroiliac joint, inflammation of the eye (iridocyclitis, uveitis) causing redness, eye pain, vision loss, floaters, photophobia, fatigue, nausea, aortitis, apical lung fibrosis, and ectasia of the sacral nerve root sheaths.

Type 1 diabetes is an autoimmune disease whereby the islet cells of the pancreas come under attack from T-cells, which renders the body incapable of producing insulin. It has been reported that β-cell destructive insulitis is associated with increased expression of IL-1 and TNF-α. Further, transgenic expression of cytokines in pancreatic islet β-cells of non-diabetes-prone mice and non-obese diabetic (NOD) mice has suggested pathogenic roles for IFNα, IFNγ, IL-2 and IL-10 in insulin-dependent diabetes mellitus (IDDM) development and protective roles for IL-4, IL-6 and TNF-α(Rabinovitch, A. Diabetes Metab. Rev. 14:129-151, 1998). Symptoms of type 1 diabetes include, but are not limited to, polyuria, polydispia and weight loss.

Guilliamé-Barre syndrome is an acute inflammatory demyelinating polyneuropathy (an autoimmune disorder affecting the peripheral nervous system). It frequently is severe, and usually exhibits as an ascending paralysis noted by weakness in the legs that spreads to the upper limbs and the face along with complete loss of deep tendon reflexes. Studies have reported that the differential expression of IL-1β, IL-6, and TNF-α in an animal model of the disease argues for a major role of these cytokines (Zhu, J., et al. Clin. Immunol. Immunopathol. 84(1):85-94. 1997). Symptoms of Guilliamé-Bane syndrome include, but are not limited to, symmetrical weakness which usually affects the lower limbs first, and rapidly progresses in an ascending fashion, "rubbery legs" with or without dysesthesias, bulbar weakness (oropharyngeal dysphagia), respiratory difficulties, facial weakness, sensory loss (proprioception), wide fluctuations in blood pressure, orthostatic hypotension, and cardiac arrhythmias.

Lupus is a chronic autoimmune connective tissue disease, affecting any part of the body, causing inflammation and tissue damage. Lupus most often harms the heart, joints, skin, lungs, blood vessels, liver, kidneys, and nervous system. Studies have shown that IL-6 and TNF-α actively are synthesized in the kidneys of patients with lupus nephritis (Herrera-Esparza, R., et al. Lupus. 7(3):154-158, 1998). Additional studies have reported that expression of TNF-α and IL-1β are elevated in animal models of lupus nephritis (Boswell, J., et al. J. Immunol. 141(9):3050-3054, 1988). Symptoms of lupus include, but are not limited to, fatigue, fever, weight gain or loss, joint pain, stiffness, swelling, malar rash on the face, skin lesions, mouth sores, alopecia, shortness of breath, chest pain, dry eyes and Raynaud's phenomenon.

Multiple sclerosis (MS) is an autoimmune disease that affects the myelinated neurons of the brain and spinal cord. MS is caused by damage to the myelin sheath; nerve impulses are slowed or stopped when this covering is damaged. Studies have reported increased expression of TNF-α in MS cases (Cannella, D., et al. Ann. Neurol. 37(4):424-435, 2004) and of IL-6 in lesions from MS patients (Lock, C., et al. Nature Medicine. 8:500-508, 2002). Symptoms of multiple sclerosis include, but are not limited to, loss of balance, muscle spasms, numbness or abnormal sensation in any area, problems moving arms or legs and walking, tremor in one or more arms or legs, constipation, stool leakage, incontinence, double vision, eye discomfort, facial pain, and hearing loss.

Psoriasis is a chronic, non-contagious autoimmune disease that affects the skin and joints. It commonly causes red, scaly patches to appear on the skin. These psoriatic plaques are areas of inflammation and excessive skin production. Skin rapidly accumulates at these sites and takes on a silvery-white appearance. Plaques can affect any area, including the elbow, the knee, the scalp, and the genitals. Studies have reported elevated levels of TNF-α, IL-1β and IL-6 in psoriasis patients (Mizutani, H., et al. J. Dermatol. Sci. 14(2):145-153. 1997).

Scleroderma is a widespread connective tissue disease that involves changes in the skin, blood vessels, muscles and internal organs. Studies have reported that IL-6 was detected more frequently in sera from scleroderma patients than in sera from controls, and that TNF-α was detected at the same levels in both patient groups, while IL-1β was not detected from either group (Needleman, B. W., et al. Arthritis Rheum. 35(1): 67-72, 1992). Skin symptoms include, but are not limited to, blanching, blueness, or redness of fingers and toes in response to heat and cold (Raynaud's phenomenon), hair loss, skin hardness, skin is abnormally dark or light, skin thickening and shiny hands and forearms, and ulcerations on fingertips or toes. Bone and muscle symptoms include, but are not limited to, joint pain, numbness and pain in the feet, pain, stiffness and swelling of fingers and joints, wrist pain. Additional symptoms include, but are not limited to, constipation, diarrhea, dry cough, wheezing, and difficulty swallowing.

Sjogren's disease (Mikulicz disease, Sicca syndrome) is an autoimmune disorder in which immune cells attack and destroy the exocrine glands that produce tears and saliva. Studies have shown that IL-1β, IL-6 and TNF-α levels are significantly different between patients with Sjogren's disease and normal healthy controls (Szodoray, P., et al. Scand. J. Immunol. 59(6):592-599). Symptoms of Sjogren's disease include, but are not limited to, dry mouth, dry eyes, skin dryness, nose dryness, and vaginal dryness.

Glomerulonephritis

Glomerulonephritis (glomerular nephritis, GN) is a renal disease characterized by inflammation of the small blood vessels (glomeruli) of the kidney. Studies have reported that the inflammatory cytokines IL-1 and TNF-α each play a role in the immune/inflammatory process in glomerulonephritis and that blocking their action reduces disease (Atkins, Nephrology. 7(s1):S2-S6, 2007); Johnson, R. J., Nephron. 73(4): 506-514, 1996). Additional studies have reported that IL-6 also plays a role in glomerulonephritis (Takemura, T., et al. Virchows Archiv. 424(5):459-464, 1994). Symptoms of glomerulonephritis include, but are not limited to, edema, high blood pressure, and the presence of red blood cells in the urine.

Urologic Chronic Pelvic Pain

Urologic chronic pelvic pain syndromes refers to pain syndromes associated with the bladder (i.e., interstitial cystitis (IC), painful bladder syndrome (PBS)) and the prostate gland (chronic prostatitis (CP), chronic pelvic pain syndrome (CPPS)). Chronic prostatitis/chronic pelvic pain syndrome (CP/CPPS) is characterized by pelvic or perineal pain without evidence of urinary tract infection, lasting longer than 3 months. Studies have reported that levels of IL-1β, TNF-α and IL-6 were elevated significantly in groups having inflammatory and non-inflammatory CPPS compared with a control group (Orhan, I., et al. Int. J. Urol. 8(9):495-9, 2001; Alexander, R. B., et al. Urology. 52(5):744-749, 1998; Jang, T. L., and Schaeffer, A. J., World J. Urol. 21(2):95-99, 2003). Symptoms of these syndromes may wax and wane. Pain may range from mild discomfort to debilitating, and may radiate from the back and rectum, making sitting difficult. Dysuria (difficult or painful urination), arthralgia (pain in a joint), myalgia (pain in the muscles), unexplained fatigue, abdominal pain, constant burning pain in the penis, and frequency may all be present. Frequent urination and increased urgency may suggest interstitial cystitis (inflammation centered in the bladder rather than prostate). Ejaculation may be painful, as the prostate contracts during emission of semen, although nerve- and muscle-mediated post-ejaculatory pain is more common. Some patients report low libido, sexual dysfunction and erectile difficulties. Pain after ejaculation is a very specific complaint that distinguishes CP/CPPS from men with benign prostatic hyperplasia (BPH) or normal men.

Inflammatory Bowel Disease (IBD)

The term "Inflammatory Bowel Disease (IBD)" refers to a group of inflammatory conditions of the large intestine and small intestine. IBDs include Crohn's disease (CD) and ulcerative colitis (UC). Other forms of IBD include collagenous colitis, lymphocytic colitis, ischaemic colitis, diversion colitis, Behcet's syndrome, infective colitis and indeterminate colitis. Many of these disorders may present the symptoms of abdominal pain, vomiting, diarrhea, hematochezia (bright red blood in stools), weight loss and various associated complaints or diseases like arthritis, pyoderma gangrenosum, and primary sclerosing cholangitis. Diagnosis is generally by colonoscopy with biopsy of pathological lesions. Studies have reported that cytokines such as IL-6, IL-1 and TNF-α play a central role in the modulation of the intestinal immune system and that the mucosal and systemic concentrations of many pro- and antiinflammatory cytokines are elevated in IBD (Rogler, G., and Andus, T. World J. Surg. 22(4):382-9, 1998). Studies also have shown elevated levels of TNF-α, IL-1β and IL-6 in Crohn's patients and that the concentrations of IL-1β and IL-6 in the supernatant fluid of biopsy cultures are positively correlated with the degree of tissue involvement measured by both endoscopic and histological grading (Reimund, J., et al. Gut. 39:684-689, 1996).

Pelvic Inflammatory Disease (PID)

Pelvic inflammatory disease (PID) refers to inflammation of the female uterus, fallopian tubes, and/or ovaries as it progresses to scar formation with adhesions to nearby tissues and organs. PID may lead to tissue necrosis and abscess formation. Studies have reported that IL-1β, IL-6 and TNF-α are significantly elevated in PID patients before antibiotic treatment (as compared to after treatment) and that these cytokines may play an important role in the pathogenesis of PID (Lee, S. A., et al. Clin. Chem. Lab. Med. 46(7):997-1003, 2008).

Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function. Studies have reported that IL-6 prevents the liver against warm ischemia/reperfusion injury through down regulation of TNF-α (Camargo, C., et al. Hepatology. 26(6):1513-1520, 2003). Symptoms include, but are not limited to, elevated white blood cell levels, apoptosis, and free radical accumulation.

Rheumatoid Arthritis (RA)

Rheumatoid arthritis (RA) is a chronic, systemic autoimmune disorder that most commonly causes inflammation and tissue damage in joints (arthritis) and tendon sheaths, together with anemia. RA also may produce diffuse inflammation in the lungs, pericardium, pleura, and the sclera of the eye, and also nodular lesions, most common in subcutaneous tissue under the skin. RA may be a disabling and painful condition, which may lead to substantial loss of functioning and mobility. Studies have reported that levels of IL-1β, IL-6 and TNF-α are elevated in the serum of RA and juvenile arthritis patients (Ziolkowska, M., et al. J. Immunol. 164:2832-2838, 2000). Symptoms of RA may manifest in the joints (swelling, pain, tenderness, a sensation of localized warmth, stiffness and restricted movement); skin (rheumatoid nodule); lungs (fibrosis, Caplan's syndrome, pleural effusions); kidneys (renal anlyoidosis); heart and blood vessels (atherosclerosis, myocardial infarction, stroke); and eyes (episcleritis, keratoconjunctivitis sicca).

Vasculitis

"Vasculitis" refers to a disorder characterized by inflammatory destruction of blood vessels (arteries and veins). Studies have reported that TNF-α, IL-1, and IL-6 are potential biological targets for the treatment of systemic vasculitis (Levine, S. M., and Stone, J. H. Best Prac. Res. Clin. Rheumatol. 15(2):315-333, 2001. Symptoms of vasculitis usually are systemic with single or multiorgan dysfunction. These symptoms may include fatigue, weakness, fever, arthralgias, abdominal pain, hypertension, renal insufficiency, and neurologic dysfunction. Additional symptoms may include mononeuritis multiplex, palpable purpura (purple patches on the skin) and pulmonary-renal syndrome. Hypersensitivity vasculitis (HSV) is a secondary vasculitis due to an immune response to exogenous substances. Studies have reported that serum IL-6 and TNF-α is significantly higher in active HSV patients than in a healthy control group (Nalbant, S., et al. Rheumatol. Int. 22(6):244-248, 2002).

5. Disorders: Fibrosis

Fibrosis is the formation or development of excess fibrous connective tissue in an organ or tissue as a result of injury or inflammation of a part, or of interference with its blood supply. It may be a consequence of the normal healing response leading to a scar, or it may be an abnormal, reactive process.

There are several types of fibrosis including, but not limited to, cystic fibrosis of the pancreas and lungs, injection fibrosis, endomyocardial fibrosis, idiopathic pulmonary fibrosis of the lung, mediastinal fibrosis, myelofibrosis, retroperitoneal fibrosis, and nephrogenic systemic fibrosis.

Cystic fibrosis (CF, mucovidosis, mucovisidosis) is an inherited autosomal recessive disorder. It is one of the most common fatal genetic disorders in the United States, affecting about 30,000 individuals, and is most prevalent in the Caucasian population, occurring in one of every 3,300 live births. The gene involved in cystic fibrosis, which was identified in 1989, codes for a protein called the cystic fibrosis transmembrane conductance regulator (CFTR). CFTR normally is expressed by exocrine epithelia throughout the body and regulates the movement of chloride ions, bicarbonate ions and glutathione into and out of cells. In cystic fibrosis patients, mutations in the CFTR gene lead to alterations or total loss of CFTR protein function, resulting in defects in osmolarity, pH and redox properties of exocrine secretions. In the lungs, CF manifests itself by the presence of a thick mucus secretion which clogs the airways. In other exocrine organs, such as the sweat glands, CF may not manifest itself by an obstructive phenotype, but rather by abnormal salt composition of the secretions (hence the clinical sweat osmolarity test to detect CF patients). The predominant cause of illness and death in cystic fibrosis patients is progressive lung disease. The thickness of CF mucus, which blocks the airway passages, is believed to stem from abnormalities in osmolarity of secretions, as well as from the presence of massive amounts of DNA, actin, proteases and prooxidative enzymes originating from a subset of inflammatory cells, called neutrophils. Indeed, CF lung disease is characterized by early, hyperactive neutrophil-mediated inflammatory reactions to both viral and bacterial pathogens. The hyperinflammatory syndrome of CF lungs has several underpinnings, among which an imbalance between pro-inflammatory chemokines, chiefly IL-8, and anti-inflammatory cytokines, chiefly IL-10, has been reported to play a major role. See Chmiel et al. Clin Rev Allergy Immunol. 3(1):5-27 (2002). Studies have reported that levels of TNF-α, IL-6 and IL-1β were higher in the bronchoaveolar lavage fluid of cystic fibrosis patients, than in healthy control bronchoaveolar lavage fluid (Bondfield, T. L., et al. Am. J. Resp. Crit. Care Med. 152(1):2111-2118, 1995).

Injection fibrosis (IF) is a complication of intramuscular injection often occurring in the quadriceps, triceps and gluteal muscles of infants and children in which subjects are unable to fully flex the affected muscle. It typically is painless, but progressive. Studies have reported that the glycoprotein osteopontin (OPN) plays a role in tissue remodeling (Liaw, L., et al. J. Clin. Invest, 101(7):1469-1478, 1998) and that this proinflammatory mediator induces IL-1β up-regulation in human monocytes and an accompanying enhanced production of TNF-α and IL-6 (Naldini, A., et al. J. Immunol. 177: 4267-4270, 2006; Weber, G. F., and Cantor, H. Cytokine Growth Factor Reviews. 7(3):241-248, 1996).

Endomyocardial disease (hyperosinophilic syndrome (HS)) is a disease process characterized by a persistently elevated eosinophil count (≥1500 eosinophils/mm$^3$) in the blood. HS affects simultaneously affects many organs, Studies have reported that IL-1β, IL-6 and TNF-α are expressed at high levels in viral-induced myocarditis patients (Satoh, M., et al. Virchows Archiv. 427(5):503-509, 1996). Symptoms may include cardiomyopathy, skin lesions, thromboembolic disease, pulmonary disease, neuropathy, hepatosplenomegaly (coincident enlargement of the liver and spleen), and reduced ventricular size. Treatment may include utilizing corticosteroids to reduce eosinophil levels.

Idiopathic pulmonary fibrosis (IPF, cryptogenic fibrosing alveolitis) is a chronic progressive interstitial lung disease of unknown cause. It is associated with a histological pattern of usual interstitial pneumonia and may be characterized by abnormal and excessive deposition of fibrotic tissue in the pulmonary interstitium with minimal associated inflammation. Studies have reported significant increases in TNF-α and IL-6 release in patients with idiopathic pulmonary fibrosis (IPF) (Zhang, Y., et al. J. Immunol. 150(9):4188-4196, 1993), which has been attributed to the level of expression of IL-1β (Kolb, M., et al. J. Clin. Invest, 107(12):1529-1536, 2001). Symptoms include dyspnea (difficulty breathing), but also include nonproductive cough, clubbing (a disfigurement of the fingers), and crackles (crackling sound in lungs during inhalation).

Mediastinal fibrosis (MF) is characterized by invasive, calcified fibrosis centered on lymph nodes that block major vessels and airways. MF is a late complication of histoplasmosis. Studies in murine models of fibrosis have reported that IL-10 and TNF-α are elevated significantly (Ebrahimi, B., et al. Am. J. Pathol. 158:2117-2125, 2001).

Myelofibrosis (myeloid metaplasia, chronic idiopathic myelofibrosis, primary myelofibrosis) is a disorder of the bone marrow in which the marrow undergoes fibrosis. Myelofibrosis leads to progressive bone marrow failure. The mean survival is five years and causes of death include infection, bleeding, organ failure, portal hypertension, and leukemic transformation. It has been reported that TNF-α and IL-6 levels are elevated in animal models of viral-induced myelofibrosis (Bousse-Kerdiles, M., et al. Ann. Hematol. 78:434-444, 1999).

Retroperitoneal fibrosis (Ormond's disease) is a disease featuring the proliferation of fibrous tissue in the retroperitoneum. The retroperitoneum is the body compartment containing the kidneys, aorta, renal tract, and other structures. It has been reported that IL-1, IL-6 and TNF-α have key roles in the pathogenesis of retroperitoneal fibrosis (Demko, T., et al, J. Am. Soc. Nephrol. 8:684-688, 1997). Symptoms of retroperitoneal fibrosis may include, but are not limited to, lower back pain, renal failure, hypertension, and deep vein thrombosis.

Nephrogenic systemic fibrosis (NSF, nephrogenic fibrosing dermopathy) involves fibrosis of the skin, joints, eyes and internal organs. NSF may be associated with exposure to gadolinium. Patients develop large areas of hardened skin with fibrotic nodules and plaques. Flexion contractures with an accompanying limitation of range of motion also may occur. NSF shows a proliferation of dermal fibroblasts and dendritic cells, thickened collagen bundles, increased elastic fibers, and deposits of mucin. Some reports have suggested that a proinflammatory state provides a predisposing factor for causing nephrogenic systemic fibrosis (Saxena, S., et al. Int. Urol. Nephrol. 40:715-724, 2008), and that the level of TNF-α is elevated in animal models of nephrogenic systemic fibrosis (Steger-Hartmann, T., et al. Exper. Tox. Pathol. 61(6): 537-552, 2009).

6. Disorders: Endothelial Cell Dysfunction

Endothelial cell dysfunction (endothelial dysfunction) refers to a physiological dysfunction of normal biochemical processes carried out by the endothelium, such as mediation of coagulation, of platelet adhesion, of immune function, and of control of volume and electrolyte content of the intravascular and extravascular spaces. Endothelial dysfunction may result from disease processes, such as, for example, septic shock, hypertension, hypercholesterolaemia, and diabetes as well as from environmental factors, such as from smoking tobacco products. Studies have reported that under the influence of cytokines, such as IL-6, IL-1β, and TNF-α, the endothelium-dependent dilation can be impaired and the endothelium may lose its ability to respond to circulating hormones or autacoids. This effect may favor a predisposition to vessel spasm, thrombosis or atherogenesis (Vila, E. and Salaices, M. Am. J. Physiol, Heart Circ. Physiol. 288:H1016-H1021, 2005). In addition, studies have suggested that the overexpression of IL-6, as regulated by IL-1β and TNF-α, has an important role in endothelial cell dysfunction (Korman, K. et al. J. Perio. Res. 34(7):353-357 (2006); Libby, P., et al. Circulation. 86 (6 Suppl): III47-52 (1992)).

Endothelial dysfunction may be characterized by the inability of arteries and arterioles to dilate fully in response to an appropriate stimulus. For example, dysfunctional endothelial cells (having reduced vasodilation) are unable to produce nitric oxide (NO) to the same extent as healthy endothelial cells. This difference is detectable by a variety of methods including iontophoresis of acetylcholine, intra-arterial administration of various vasoactive agents, localized heating of the skin and temporary arterial occlusion by inflating a blood pressure cuff to high pressures. Testing also may take place in the coronary arteries themselves, however this invasive procedure normally is not conducted unless there is a clinical reason for intracoronary catheterization. These techniques are thought to stimulate the endothelium to release NO which diffuses into the surrounding vascular smooth muscle causing vasodilation.

Systems that allow for delivery of biologically active recombinant proteins and peptide therapeutics have been the subject of numerous studies. Systems for localized delivery of therapeutic agents allow for the biological effects of such agents to achieve greater efficacy.

Challenges persist to deliver recombinant proteins to desired targets in vivo. Despite developments in the area of protein transduction peptides, the classical delivery methods of protein-coding genes via adeno-associated virus, adenovirus, lentivirus, herpes virus vectors, and plasmid expression vectors remain the preferred choice for expression of proteins.

Viral vector-mediated gene expression is considered the most efficient and reliable approach for expressing functional proteins de novo in mitotically active or postmitotically blocked cell types due to the natural ability of such vectors to deliver the specific genes to permissive cells. Nonetheless, viral vectors invariably are required in large doses to achieve therapeutic expression levels of intended proteins. Moreover, viral vectors may integrate with the host chromatin material. These properties exert long term effects on host genetic systems, and therefore, safety remains a serious concern for their ultimate clinical application.

An alternative, safer, approach is to produce recombinant proteins exogenously and then deliver them systemically or by localized injections into the target organs. However, the delivery and bioavailability of recombinant proteins into cells or tissues need further improvements. Although several studies have suggested the potential of PTD in drug discovery and transduction of proteins up to 120 kDa into different cells, questions about potency of PTD mediated protein transduction still remain unsolved. Indeed, some studies have demonstrated failures in PTD-mediated fusion protein transduction in vitro/in vivo as well as an inability to induce an immune response. Further, some studies have shown that intracellular expression of PTD fusion proteins or other non-secretory proteins may not achieve the same biodistribution as recombinant protein, and entry of PTD through the blood-brain barrier remains elusive.

The described invention provides therapeutic inhibitor peptides for the inhibition of kinases, uses of a class of peptides that include therapeutic domains and protein transduction domains as inhibitors of kinase activity, and uses of PTDs as therapeutic agents for a variety of disorders.

SUMMARY

The described invention provides kinase inhibiting compositions containing a therapeutic amount of a therapeutic inhibitor peptide that inhibits at least one kinase enzyme, methods for treating an inflammatory disorder whose pathophysiology comprises inflammatory cytokine expression, and methods for treating an inflammatory disorder whose pathophysiology comprises inflammatory cytokine expression using the kinase inhibiting compositions.

According to one aspect, the described invention provides a kinase inhibiting composition for treating an inflammatory disorder whose pathophysiology comprises inflammatory cytokine expression, the composition comprising (a) a therapeutically effective amount of a therapeutic inhibitor peptide, wherein the therapeutically effective amount of the therapeutic inhibitor peptide inhibits at least one kinase enzyme, wherein the therapeutic inhibitor peptide comprises a first domain and a second domain, wherein the first domain comprises a protein transduction domain and is located proximal to the second domain, wherein the second domain comprises a therapeutic domain and is located proximal to the first domain, and (b) a pharmaceutically acceptable carrier, wherein the composition directly or indirectly reduces expression of at least one inflammatory cytokine. According to one embodiment, the therapeutic inhibitor peptide is a peptide whose amino acid sequence has substantial identity to amino acid sequence YARRAAARQARAKALARQLGVAA [SEQ ID NO: 11]. According to another embodiment, the therapeutic domain of the therapeutic inhibitor peptide has substantial identity to amino acid sequence KALNRQLGVAA [SEQ ID NO: 13]. According to another embodiment, the transduction domain of the therapeutic inhibitor peptide has substantial identity to amino acid sequence WLRRIKAWLRRIKA [SEQ ID NO: 31]. According to another embodiment, the protein transduction domain of the therapeutic inhibitor peptide has substantial identity to amino acid sequence YARAAARQARA [SEQ ID NO: 5]. According to another embodiment, the protein transduction domain of the therapeutic inhibitor peptide has substantial identity to amino acid sequence FAKLAARLYRKA [SEQ ID NO: 43]. According to another embodiment, the transduction domain of the therapeutic inhibitor peptide has substantial identity to amino acid sequence FAKLAARLYRKALARQLGVAA [SEQ ID NO: 12]. According to another embodiment, the protein transduction domain of the therapeutic inhibitor peptide has substantial identity to amino acid sequence KAFAKLAARLYRKA [SEQ ID NO: 44]. According to another embodiment, the therapeutic inhibitor peptide is a peptide whose amino acid sequence has substantial identity to amino acid sequence KAFAKLAARLYRKALARQLGVAA [SEQ ID NO: 15]. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits TNF-α excretion. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits IL-1β excretion. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits IL-6 excretion. According to another embodiment, the kinase enzyme is a mitogen-activated protein kinase-activated protein kinase. According to another embodiment, the kinase enzyme is mitogen-activated protein kinase-activated protein kinase 2. According to another embodiment, the kinase enzyme is mitogen-activated protein kinase-activated protein kinase 3. According to another embodiment, the kinase enzyme is $Ca^{2+}$/calmodulin-dependent protein kinase. According to another embodiment, the inflammatory disorder whose pathophysiology comprises inflammatory cytokine expression is at least one disorder selected from the group consisting of asthma, ankylosing spondylitis, Type I diabetes, Guilliamé-Barre syndrome, lupus, psoriasis, scleroderma, Sjogren's disease, chronic prostatitis, glomerulonephritis, inflammatory bowel disease, pelvic inflammatory disease, reperfusion injury, rheumatoid arthritis, vasculitis, hypersensitivity vasculitis, endotoxic shock, pancreatitis, localized inflammatory disease, atherosclerosis, Alzheimer's disease, ischemia, intimal hyperplasia, stenosis, restenosis, leiomyoma, smooth muscle spasm, angina, Prinzmetal's angina, bradycardia, hypertension, cardiac hypertrophy, renal failure, stroke, pulmonary hypertension, toxemia of pregnancy, Raynaud's disease, hemolytic uremia, anal fissure, achalasia, impotence, migraine, vasculopathy, congestive heart failure, stunned myocardium, diastolic dysfunction, gliosis, chronic obstructive pulmonary disease, osteopenia, degenerative arthritis, sepsis, cirrhosis, interstitial fibrosis, colitis, appendicitis, gastritis, laryngitis, meningitis, otitis, traumatic brain injury, spinal cord injury, peripheral neuropathy, multiple sclerosis, cardiometabolic syndrome, non-alcoholic steatohepatitis, cystic fibrosis of the pancreas and lungs, injection fibrosis, endomyocardial fibrosis, idiopathic pulmonary fibrosis of the lung, mediastinal fibrosis, myelofibrosis, retroperitoneal fibrosis, nephrogenic systemic fibrosis, breast cancer, prostate cancer and endothelial cell dysfunction. According to another embodiment, the at least one inflammatory cytokine is at least one of IL-6, TNFα, and IL-1β. According to another embodiment, the composition is disposed on or in a biomedical device.

According to one aspect, the described invention provides a kinase inhibiting composition for treating an inflammatory disorder whose pathophysiology comprises inflammatory cytokine expression, the composition comprising (a) a therapeutically effective amount of a therapeutic inhibitor peptide, wherein the therapeutically effective amount of the therapeutic inhibitor peptide inhibits at least one kinase enzyme, wherein the therapeutic inhibitor peptide comprises a first domain and a second domain, wherein the first domain comprises a protein transduction domain and is located proximal to the second domain, wherein the second domain comprises a therapeutic domain and is located proximal to the first domain, and (b) a pharmaceutically acceptable carrier, wherein the composition directly or indirectly reduces expression of at least one inflammatory cytokine. According to one embodiment, the therapeutic inhibitor peptide is a peptide whose amino acid sequence has substantial identity to amino acid sequence YARRAAARQARAKALAR-QLGVAA [SEQ ID NO: 71]. According to another embodiment, the therapeutic domain of the therapeutic inhibitor peptide has substantial identity to amino acid sequence KALNRQLGVAA [SEQ ID NO: 13]. According to another embodiment, the transduction domain of the therapeutic inhibitor peptide has substantial identity to amino acid sequence WLRRIKAWLRRIKA [SEQ ID NO: 31]. According to another embodiment, the protein transduction domain of the therapeutic inhibitor peptide has substantial identity to amino acid sequence YARAAARQARA [SEQ ID NO: 5]. According to another embodiment, the protein transduction domain of the therapeutic inhibitor peptide has substantial identity to amino acid sequence FAKLAARLYRKA [SEQ ID NO: 43]. According to another embodiment, the transduction domain of the therapeutic inhibitor peptide has substantial identity to amino acid sequence FAKLAARLYRKALAR-QLGVAA [SEQ ID NO: 12]. According to another embodiment, the protein transduction domain of the therapeutic inhibitor peptide has substantial identity to amino acid sequence KAFAKLAARLYRKA [SEQ ID NO: 44]. According to another embodiment, the therapeutic inhibitor peptide is a peptide whose amino acid sequence has substantial identity to amino acid sequence KAFAKLAARLYRKALAR-QLGVAA [SEQ ID NO: 15]. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits TNF-.alpha. excretion. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits IL-1β excretion. According to another embodiment, the polypeptide comprises at least one variant that is at least 90% identical to at least one of SEQ ID NO: 11, SEQ ID NO: 12, SEQ ID NO: 13, and SEQ ID NO: 15 and that inhibits IL-6 excretion. According to another embodiment, the kinase enzyme is a mitogen-activated protein kinase-activated protein kinase. According to another embodiment, the kinase enzyme is mitogen-activated protein kinase-activated protein kinase 2. According to another embodiment, the kinase enzyme is mitogen-activated protein kinase-activated protein kinase 3. According to another embodiment, the kinase enzyme is $Ca^{2+}$/calmodulin-dependent protein kinase. According to another embodiment, the inflammatory disorder whose pathophysiology comprises inflammatory cytokine expression is at least one disorder selected from the group consisting of asthma, ankylosing spondylitis, Type I diabetes, Guilliame-Barre syndrome, lupus, psoriasis, scleroderma, Sjogren's disease, chronic prostatitis, glomerulonephritis, inflammatory bowel disease, pelvic inflammatory disease, reperfusion injury, rheumatoid arthritis, vasculitis, hypersensitivity vasculitis, endotoxic shock, pancreatitis, localized inflammatory disease, atherosclerosis, Alzheimer's disease, ischemia, intimal hyperplasia, stenosis, restenosis, leiomyoma, smooth muscle spasm, angina, Prinzmetal's angina, bradycardia, hypertension, cardiac hypertrophy, renal failure, stroke, pulmonary hypertension, toxemia of pregnancy, Raynaud's disease, hemolytic uremia, anal fissure, achalasia, impotence, migraine, vasculopathy, congestive heart failure, stunned myocardium, diastolic dysfunction, gliosis, chronic obstructive pulmonary disease, osteopenia, degenerative arthritis, sepsis, cirrhosis, interstitial fibrosis, colitis, appendicitis, gastritis, laryngitis, meningitis, otitis, traumatic brain injury, spinal cord injury, peripheral neuropathy, multiple sclerosis, cardiometabolic syndrome, non-alcoholic steatohepatitis, cystic fibrosis of the pancreas and lungs, injection fibrosis, endomyocardial fibrosis, idiopathic pulmonary fibrosis of the lung, mediastinal fibrosis, myelofibrosis, retroperitoneal fibrosis, nephrogenic systemic fibrosis, breast cancer, prostate cancer and endothelial cell dysfunction. According to another embodiment, the at least one inflammatory cytokine is at least one of IL-6, TNFα, and IL-1β. According to another embodiment, the composition is disposed on or in a biomedical device.

BRIEF DESCRIPTION OF THE DRAWINGS

FIG. 1 discloses SEQ ID NOS 5, 30, 67-70 and 16, respectively, in order of appearance.

FIG. 2 discloses SEQ ID NOS 14, 12, 15, 11 and 16. respectively, in order of appearance.

FIG. 3 discloses SEQ ID NOS 22-28 and 13, respectively, in order of appearance. RFU/s=relative fluorescence units per second.

FIG. 4 discloses KALNROLGVAA as SEQ ID NO: 13. RFU/s=relative fluorescence units per second.

FIG. 5 discloses SEQ ID NOS 29-30, 14 and 13, respectively, in order of appearance. RFU/s=relative fluorescence units per second.

FIG. 6 discloses SEQ ID NOS 32, 31, 33, 5 and 13, respectively, in order of appearance. RFU/s=relative fluorescence units per second.

DETAILED DESCRIPTION

Figure 1:
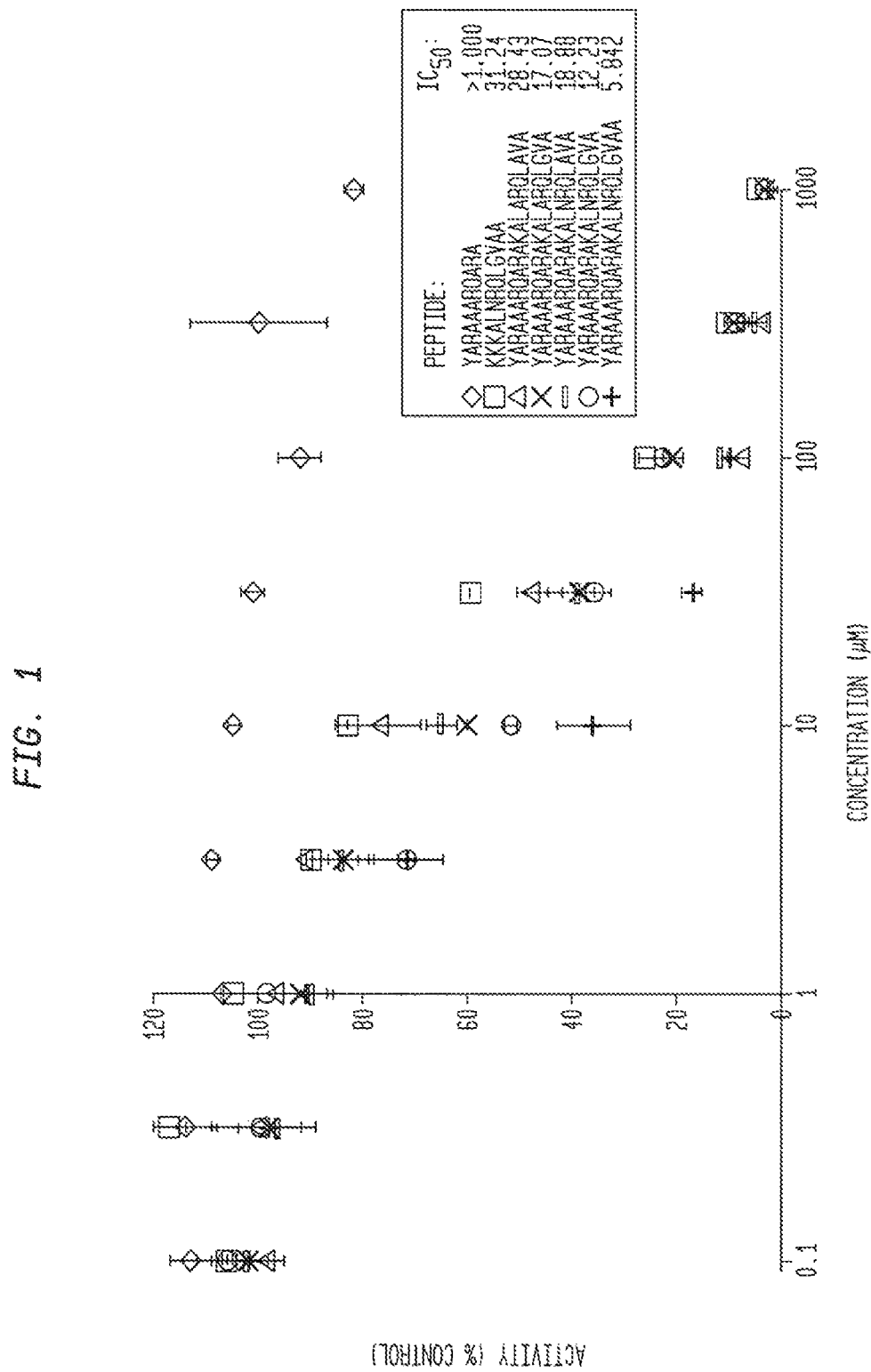
FIG. 1 shows a plot of activity (% relative to the control) versus inhibitor peptide concentration (μM).

The described invention provides therapeutic kinase inhibiting compositions and methods useful for inhibiting mitogen-activated protein kinase-activated protein kinases.

Glossary

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

Additional administration may be performed, for example, intravenously, pericardially, orally, via implant, transmucosally, transdermally, intramuscularly, subcutaneously, intraperitoneally, intrathecally, intralymphatically, intralesionally, or epidurally. Administering can be performed, for example, once, a plurality of times, and/or over one or more extended periods. The term "topical administration" and "topically applying" as used herein are used interchangeably to refer to delivering a peptide, the nucleic acid, or a vector comprising the peptide or the nucleic acid onto one or more surfaces of a tissue or cell, including epithelial surfaces.

Topical administration, in contrast to transdermal administration, generally provides a local rather than a systemic effect. The terms "topical administration" and "transdermal administration" as used herein, unless otherwise stated or implied, are used interchangeably.

The term "associate" and its various grammatical forms as used herein refers to joining, connecting, or combining to, either directly, indirectly, actively, inactively, inertly, non-inertly, completely or incompletely.

The term "biocompatible" as used herein refers to causing no clinically relevant tissue irritation, injury, toxic reaction, or immunological reaction to living tissue based on a clinical risk/benefit assessment.

The term "biodegradable" as used herein refers to material that will degrade actively or passively over time by simple chemical processes, by action of body enzymes or by other similar mechanisms in the human body.

The term "carrier" as used herein refers to an organic or inorganic ingredient, natural or synthetic, with which the active ingredient is combined to facilitate the application that does not cause significant irritation to an organism and does not abrogate the biological activity and properties of the composition of the described invention. Carriers must be of sufficiently high purity and of sufficiently low toxicity to render them suitable for administration to a subject being treated. The carrier can be inert, or it can possess pharmaceutical benefits, cosmetic benefits or both.

The term "condition" as used herein refers to a variety of health states and is meant to include disorders or diseases caused by any underlying mechanism or disorder, injury, and the promotion of healthy tissues and organs.

The term "contacting" as used herein refers to bringing or putting in contact. The term "contact" as used herein refers to a state or condition of touching or of immediate or local proximity. Contacting a composition to a target destination, such as, but not limited to, an organ, tissue, cell, or tumor, may occur by any means of administration known to the skilled artisan.

The term "controllable regulatory element" as used herein refers to nucleic acid sequences capable of effecting the expression of the nucleic acids, or the peptide or protein product thereof. Controllable regulatory elements may be operably linked to the nucleic acids, peptides, or proteins of the present invention. The controllable regulatory elements, such as, but not limited to, control sequences, need not be contiguous with the nucleic acids, peptides, or proteins whose expression they control as long as they function to direct the expression thereof. Thus, for example, intervening untranslated yet transcribed sequences may be present between a promoter sequence and a nucleic acid of the present invention and the promoter sequence may still be considered "operably linked" to the coding sequence. Other such control sequences include, but are not limited to, polyadenylation signals, termination signals, and ribosome binding sites.

The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "disease" or "disorder" as used herein generally refers to an impairment of health or a condition of abnormal functioning. Disorders relevant to the described invention may include, but are not limited to, inflammatory diseases, fibrosis, endotoxic shock, pancreatitis, asthma, localized inflammatory disease, atherosclerotic cardiovascular disease, Alzheimer's disease, oncological diseases, neural ischemia, rheumatoid arthritis, Crohn's disease, inflammatory bowel disease, intimal hyperplasia, stenosis, restenosis, atherosclerosis, smooth muscle cell tumors and metastasis, smooth muscle spasm, angina, Prinzmetal's angina, ischemia, bradycardia, hypertension, cardiac hypertrophy, renal failure, stroke, pulmonary hypertension, toxemia of pregnancy, preterm labor, pre-eclampsia, eclampsia, Raynaud's disease or phenomenon, hemolytic-uremia, anal fissure, achalasia, impotence, migraine, ischemic muscle injury associated with smooth muscle spasm, vasculopathy, bradyarrythmia, congestive heart failure, stunned myocardium, pulmonary hypertension, diastolic dysfunction, gliosis (meaning proliferation of astrocytes, which may include deposition of extracellular matrix (ECM) in damaged areas of the central nervous system), chronic obstructive pulmonary disease (meaning respiratory tract diseases characterized by airflow obstruction or limitation; includes but is not limited to chronic bronchitis and emphysema), osteopenia, endothelial dysfunction, inflammation, degenerative arthritis, ankylosing spondylitis, Sjogren's disease, Guilliamé-Barre disease, infectious disease, sepsis, endotoxemic shock, psoriasis, radiation enteritis, scleroderma, cirrhosis, interstitial fibrosis, colitis, appendicitis, gastritis, laryngitis, meningitis, pancreatitis, otitis, reperfusion injury, traumatic brain injury, spinal cord injury, peripheral neuropathy, multiple sclerosis, Lupus, allergy, cardiometabolic diseases, obesity, type II diabetes mellitus, type I diabetes mellitus, and NASH/cirrhosis.

The term "domain" as used herein refers to a structural unit of a protein that folds more or less independently to form a globular compact structure. The term "drug" as used herein refers to a therapeutic agent or any substance, other than food, used in the prevention, diagnosis, alleviation, treatment, or cure of disease.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. The effects of base incompatibility may be measured by quantifying the rate at which two strands anneal, this may provide information as to the similarity in base sequence between the two strands being annealed.

The term "hydrogel" as used herein refers to a substance resulting in a solid, semisolid, pseudoplastic, or plastic structure containing a necessary aqueous component to produce a gelatinous or jelly-like mass. The hydrogel incorporates and retains significant amounts of $H_2O$, which eventually will reach an equilibrium content in the presence of an aqueous environment.

The term "hydrophilic" as used herein refers to a material or substance having an affinity for polar substances, such as water.

The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The terms "inhibiting", "inhibit" or "inhibition" as used herein are used to refer to reducing the amount or rate of a process, to stopping the process entirely, or to decreasing, limiting, or blocking the action or function thereof. Inhibition may include a reduction or decrease of the amount, rate, action function, or process by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99% when compared to a reference substance, wherein the reference substance is a substance that is not inhibited.

The term "injury" as used herein refers to damage or harm to a structure or function of the body caused by an outside agent or force, which may be physical or chemical.

The term "isolated" refers to material, such as a nucleic acid, a peptide, or a protein, which is: (1) substantially or essentially free from components that normally accompany or interact with it as found in its naturally occurring environment. The terms "substantially or essentially free" are used to refer to a material, which is at least 80% free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "kinase" as used herein refers to a type of enzyme that transfers phosphate groups from high-energy donor molecules to specific target molecules or substrates. High-energy donor groups may include, but are not limited, to ATP.

The term "kinase activity" as used herein refers to kinase mediated phosphorylation of a kinase substrate.

The term "kinase substrate" as used herein refers to a substrate that can be phosphorylated by a kinase.

The term "labile" in its various grammatical forms as used herein refers to being apt or likely to change. A labile compound is one capable of changing state or becoming inactive.

The term "lipophilic" as used herein refers to preferring or possessing an affinity for a non-polar environment compared to a polar or aqueous environment.

The term "long-term release", as used herein, means that an implant is constructed and arranged to deliver therapeutic levels of an active ingredient for at least 7 days, or about 30 to about 60 days.

The term "mammalian cell" as used herein refers to a cell derived from an animal of the class Mammalia. As used herein, mammalian cells may include normal, abnormal and transformed cells. Examples of mammalian cells utilized within the described invention, include, but are not limited to, neurons, epithelial cells, muscle cells, blood cells, immune cells, stem cells, osteocytes, endothelial cells and blast cells.

The term "modulate" as used herein means to regulate, alter, adapt, or adjust to a certain measure or proportion.

The term "normal" refers to a standard, model, median or average of a large group.

The term "normal healthy subject" refers to a subject having no symptoms or other evidence of an inflammatory disorder.

The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The phrase "operably linked" refers to a first sequence(s) or domain being positioned sufficiently proximal to a second sequence(s) or domain so that the first sequence(s) or domain can exert influence over the second sequence(s) or domain or a region under control of that second sequence or domain.

The term "particles" as used herein refers to refers to an extremely small constituent (e.g., nanoparticles, microparticles, or in some instances larger) that may contain in whole or in part the kinase inhibiting composition as described herein.

The term "peptide" as used herein refers to two or more amino acids joined by a peptide bond.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "peptidomimetic" as used herein refers to a small protein-like chain designed to mimic a peptide. A peptidomimetic typically arises from modification of an existing peptide in order to alter the molecule's properties.

The term "pharmaceutically-acceptable carrier" as used herein refers to one or more compatible solid or liquid filler, diluents or encapsulating substances which are suitable for administration to a human or other vertebrate animal.

The term "polymer" as used herein refers to any of various chemical compounds made of smaller, identical molecules (called monomers) linked together. Polymers generally have high molecular weights. The process by which molecules are linked together to form polymers is called "polymerization."

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "primary sequence" as used herein refers to an amino acid sequence.

The term "prodrug" as used herein means a peptide or derivative, which is in an inactive form, and, which is converted to an active form by biological conversion following administration to a subject.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "protein transduction domain" (also referred to as "PTD", "Trojan peptide", "membrane translocating sequence", "cell permeable protein", "CPP") as used herein refers to a class of peptides generally capable of penetrating the plasma membrane of mammalian cells. PTDs generally are 10-16 amino acids in length, and are capable of transporting compounds of many types and molecular weights across mammalian cells. These compounds include, but are not limited to, effector molecules, such as proteins, DNA, conjugated peptides, oligonucleotides, and small particles such as liposomes. When PTDs are chemically linked or fused to other proteins to form fusion proteins, these fusion proteins still are able to penetrate the plasma membrane and enter cells.

The term "reduce" or "reducing" as used herein refers to a lowering or lessening in degree, intensity, state, condition, or extent.

The term "regulatory sequence" (also referred to as a "regulatory region" or "regulatory element") refers to a promoter, enhancer or other segment of DNA where regulatory proteins, such as transcription factors, bind preferentially to control gene expression and thus protein expression.

The term "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period.

The term "symptom" as used herein refers to a sign or an indication of disorder or disease, especially when experienced by an individual as a change from normal function, sensation, or appearance.

The term "syndrome" as used herein refers to a pattern of symptoms indicative of some disease or condition.

The term "therapeutic agent" as used herein refers to a drug, molecule, nucleic acid, protein, metabolite, peptide, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic domain" as used herein refers to a peptide, peptide segment, or variant or derivative thereof, with substantial identity to peptide KALNRQLGVAA [SEQ ID NO: 13], or segment thereof. Therapeutic domains generally are not capable of penetrating the plasma membrane of mammalian cells and when contacted with a kinase enzyme, inhibit the kinase enzyme such that the kinase activity of the kinase enzyme is reduced. A therapeutic domain may inhibit a kinase enzyme such that the activity of the kinase enzyme is about 99% of that of an uninhibited kinase enzyme. A therapeutic domain may inhibit a kinase enzyme such that the activity of the kinase enzyme is about 95% of that of an uninhibited kinase enzyme. A therapeutic domain may inhibit a kinase enzyme such that the activity of the kinase enzyme is about 90% of that of an uninhibited kinase enzyme. A therapeutic domain may inhibit a kinase enzyme such that the activity of the kinase enzyme is about 85% of that of an uninhibited kinase enzyme. A therapeutic domain may inhibit a kinase enzyme such that the activity of the kinase enzyme is about 80% of that of an uninhibited kinase enzyme. A therapeutic domain may inhibit a kinase enzyme such that the activity of the kinase enzyme is about 75% of that of an uninhibited kinase enzyme. A therapeutic domain may inhibit a kinase enzyme such that the activity of the kinase enzyme is about 70% of that of an uninhibited kinase enzyme. A therapeutic domain may inhibit a kinase enzyme such that the activity of the kinase enzyme is about 80% of that of an uninhibited kinase enzyme. A therapeutic domain may inhibit a kinase enzyme such that the activity of the kinase enzyme is about 75% of that of an uninhibited kinase enzyme. A therapeutic domain may inhibit a kinase enzyme such that the activity of the kinase enzyme is about 70% of that of an uninhibited kinase enzyme. A therapeutic domain may inhibit a kinase enzyme such that the activity of the kinase enzyme is about 65% of that of an uninhibited kinase enzyme. A therapeutic domain may inhibit a kinase enzyme such that the activity of the kinase enzyme is about 60% of that of an uninhibited kinase enzyme. A therapeutic domain may inhibit a kinase enzyme such that the activity of the kinase enzyme is about 55% of that of an uninhibited kinase enzyme. A therapeutic domain may inhibit a kinase enzyme such that the activity of the kinase enzyme is about 50% of that of an uninhibited kinase enzyme. A therapeutic domain may inhibit a kinase enzyme such that the activity of the kinase enzyme is about 45% of that of an uninhibited kinase enzyme. A therapeutic domain may inhibit a kinase enzyme such that the activity of the kinase enzyme is about 40% of that of an uninhibited kinase enzyme. A therapeutic domain may inhibit a kinase enzyme such that the activity of the kinase enzyme is about 35% of that of an uninhibited kinase enzyme. A therapeutic domain may inhibit a kinase enzyme such that the activity of the kinase enzyme is about 30% of that of an uninhibited kinase enzyme. A therapeutic domain may inhibit a kinase enzyme such that the activity of the kinase enzyme is about 25% of that of an uninhibited kinase enzyme. A therapeutic domain may inhibit a kinase enzyme such that the activity of the kinase enzyme is about 20% of that of an uninhibited kinase enzyme. A therapeutic domain may inhibit a kinase enzyme such that the activity of the kinase enzyme is about 15% of that of an uninhibited kinase enzyme. A therapeutic domain may inhibit a kinase enzyme such that the activity of the kinase enzyme is about 10% of that of an uninhibited kinase enzyme. A therapeutic domain may inhibit a kinase enzyme such that the activity of the kinase enzyme is about 9% of that of an uninhibited kinase enzyme. A therapeutic domain may inhibit a kinase enzyme such that the activity of the kinase enzyme is about 8% of that of an uninhibited kinase enzyme. A therapeutic domain may inhibit a kinase enzyme such that the activity of the kinase enzyme is about 7% of that of an uninhibited kinase enzyme. A therapeutic domain may inhibit a kinase enzyme such that the activity of the kinase enzyme is about 6% of that of an uninhibited kinase enzyme. A therapeutic domain may inhibit a kinase enzyme such that the activity of the kinase enzyme is about 5% of that of an uninhibited kinase enzyme. A therapeutic domain may inhibit a kinase enzyme such that the activity of the kinase enzyme is about 4% of that of an uninhibited kinase enzyme. A therapeutic domain may inhibit a kinase enzyme such that the activity of the kinase enzyme is about 3% of that of an uninhibited kinase enzyme. A therapeutic domain may inhibit a kinase enzyme such that the activity of the kinase enzyme is about 2% of that of an uninhibited kinase enzyme. A therapeutic domain may inhibit a kinase enzyme such that the activity of the kinase enzyme is about 1% of that of an uninhibited kinase enzyme. A therapeutic domain may inhibit a kinase enzyme such that the activity of the kinase enzyme is about 0.1% of that of an uninhibited kinase enzyme. A therapeutic domain may inhibit a kinase enzyme such that the activity of the kinase enzyme is about 0.01% of that of an uninhibited kinase enzyme.

The term "therapeutic inhibitor peptide" as used herein refers to a peptide comprised of a first domain and a second domain. The first domain comprises a protein transduction domain (PTD) and is located proximal to the second domain. The second domain, located proximal to the first domain, comprises a therapeutic domain. The term "proximal" as used herein refers to very near or next, as in space, time or order.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation. The term "therapeutically effective amount" or an "amount effective" of one or more of the active agents of the present invention is an amount that is sufficient to provide a therapeutic effect. Generally, an effective amount of the active agents that can be employed according to the described invention ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

Methods exist for the transduction and the transfection of nucleic acids into cells. The terms "transduction," or "transduce" as used herein are used interchangeably to refer to the process of crossing biological membranes. The crossing of biological membranes may be from one cell to another, from the extracellular environment to the intracellular environment, or across a cell membrane or nuclear membrane. Materials that may undergo transduction include, but are not limited to, proteins, fusion proteins, peptides, polypeptides, amino acids, viral DNA, and bacterial DNA.

The term "treat" or "treating" as used herein refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously symptomatic for the disorder.

The term "variant" and its various grammatical forms as used herein refers to a nucleotide sequence or an amino acid sequence with substantial identity to a reference nucleotide sequence or reference amino acid sequence, respectively. The differences in the sequences may be the result of changes, either naturally or by design, in sequence or structure. Natural changes may arise during the course of normal replication or duplication in nature of a particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants: or "derivatives" of the original sequence.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least on amino acid includes a substituent group; (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "substitution" is used herein to refer to that in which a base or bases are exchanged for another base or bases in the DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The term "deletion" and "deletion mutation" are used interchangeably herein to refer to that in which a base or bases are lost from the DNA.

The term "addition" as used herein refers to the insertion of one or more bases, or of one or more amino acids, into a sequence.

The following represent groups of amino acids that are conservative substitutions for one another: 1) Alanine (A), Serine (S), Threonine (T); 2) Aspartic Acid (D), Glutamic Acid (E); 3) Asparagine (N), Glutamic Acid (Q); 4) Arginine (R), Lysine (K); 5) Isoleucine (I), Leucine (L), Methionine (M), Valine (V); and 6) Phenylalanine (F), Tyrosine (Y), Tryptophan (W).

Compositions: Therapeutic Kinase Inhibitor Peptides

According to one aspect, the described invention provides a kinase inhibiting composition for treating a an inflammatory disorder whose pathophysiology comprises inflammatory cytokine expression, the composition comprising (a) a therapeutically effective amount of a therapeutic inhibitor peptide, wherein the therapeutically effective amount of the therapeutic inhibitor peptide inhibits at least one kinase enzyme, wherein the therapeutic inhibitor peptide comprises a first domain and a second domain, wherein the first domain comprises a protein transduction domain (PTD) and is located proximal to the second domain, wherein the second domain, located proximal to the first domain, comprises a therapeutic domain, wherein the composition directly or indirectly reduces expression of at least one inflammatory cytokine. According to one embodiment, the first domain is located 5' to the second domain. According to another embodiment, the second domain is located 3' to the first domain.

According to one embodiment, the therapeutically effective amount of the therapeutic inhibitor peptide is of an amount from about 0.000001 mg/kg body weight to about 100 mg/kg body weight. According to another embodiment, the therapeutically effective amount of the therapeutic inhibitory peptide is of an amount from about 0.00001 mg/kg body weight to about 100 mg/kg body weight. According to another embodiment, the therapeutically effective amount of the therapeutic inhibitory peptide is of an amount from about 0.0001 mg/kg body weight to about 100 mg/kg body weight. According to another embodiment, the therapeutically effective amount of the therapeutic inhibitory peptide is of an amount from about 0.001 mg/kg body weight to about 100 mg/kg body weight. According to another embodiment, the therapeutically effective amount of the therapeutic inhibitory peptide is of an amount from about 0.01 mg/kg body weight to about 100 mg/kg body weight. According to another embodiment, the therapeutically effective amount of the therapeutic inhibitory peptide is of an amount from about 0.1 mg/kg body weight to about 100 mg/kg body weight. According to another embodiment, the therapeutically effective amount of the therapeutic inhibitory peptide is of an amount from about 1 mg/kg body weight to about 100 mg/kg body weight. According to another embodiment, the therapeutically effective amount of the therapeutic inhibitory peptide is of an amount from about 10 mg/kg body weight to about 100 mg/kg body weight. According to another embodiment, the therapeutically effective amount of the therapeutic inhibitory peptide is of an amount from about 20 mg/kg body weight to about 100 mg/kg body weight. According to another embodiment, the therapeutically effective amount of the therapeutic inhibitory peptide is of an amount from about 30 mg/kg body weight to about 100 mg/kg body weight. According to another embodiment, the therapeutically effective amount of the therapeutic inhibitory peptide is of an amount from about 40 mg/kg body weight to about 100 mg/kg body weight.

According to another embodiment, the therapeutically effective amount of the therapeutic inhibitory peptide is of an amount from about 50 mg/kg body weight to about 100 mg/kg body weight. According to another embodiment, the therapeutically effective amount of the therapeutic inhibitory peptide is of an amount from about 60 mg/kg body weight to about 100 mg/kg body weight. According to another embodiment, the therapeutically effective amount of the therapeutic inhibitory peptide is of an amount from about 70 mg/kg body weight to about 100 mg/kg body weight. According to another embodiment, the therapeutically effective amount of the therapeutic inhibitory peptide is of an amount from about 80 mg/kg body weight to about 100 mg/kg body weight. According to another embodiment, the therapeutically effective amount of the therapeutic inhibitory peptide is of an amount from about 90 mg/kg body weight to about 100 mg/kg body weight. According to another embodiment, the therapeutically effective amount of the therapeutic inhibitor peptide is of an amount from about 0.000001 mg/kg body weight to about 90 mg/kg body weight. According to another embodiment, the therapeutically effective amount of the therapeutic inhibitor peptide is of an amount from about 0.000001 mg/kg body weight to about 80 mg/kg body weight. According to another embodiment, the therapeutically effective amount of the therapeutic inhibitor peptide is of an amount from about 0.000001 mg/kg body weight to about 70 mg/kg body weight. According to another embodiment, the therapeutically effective amount of the therapeutic inhibitor peptide is of an amount from about 0.000001 mg/kg body weight to about 60 mg/kg body weight. According to another embodiment, the therapeutically effective amount of the therapeutic inhibitor peptide is of an amount from about 0.000001 mg/kg body weight to about 50 mg/kg body weight. According to another embodiment, the therapeutically effective amount of the therapeutic inhibitor peptide is of an amount from about 0.000001 mg/kg body weight to about 40 mg/kg body weight. According to another embodiment, the therapeutically effective amount of the therapeutic inhibitor peptide is of an amount from about 0.000001 mg/kg body weight to about 30 mg/kg body weight. According to another embodiment, the therapeutically effective amount of the therapeutic inhibitor peptide is of an amount from about 0.000001 mg/kg body weight to about 20 mg/kg body weight. According to another embodiment, the therapeutically effective amount of the therapeutic inhibitor peptide is of an amount from about 0.000001 mg/kg body weight to about 10 mg/kg body weight. According to another embodiment, the therapeutically effective amount of the therapeutic inhibitor peptide is of an amount from about 0.000001 mg/kg body weight to about 1 mg/kg body weight. According to another embodiment, the therapeutically effective amount of the therapeutic inhibitor peptide is of an amount from about 0.000001 mg/kg body weight to about 0.1 mg/kg body weight. According to another embodiment, the therapeutically effective amount of the therapeutic inhibitor peptide is of an amount from about 0.000001 mg/kg body weight to about 0.1 mg/kg body weight. According to another embodiment, the therapeutically effective amount of the therapeutic inhibitor peptide is of an amount from about 0.000001 mg/kg body weight to about 0.01 mg/kg body weight. According to another embodiment, the therapeutically effective amount of the therapeutic inhibitor peptide is of an amount from about 0.000001 mg/kg body weight to about 0.001 mg/kg body weight. According to another embodiment, the therapeutically effective amount of the therapeutic inhibitor peptide is of an amount from about 0.000001 mg/kg body weight to about 0.0001 mg/kg body weight. According to another embodiment, the therapeutically effective amount of the therapeutic inhibitor peptide is of an amount from about 0.000001 mg/kg body weight to about 0.00001 mg/kg body weight.

According to another embodiment, the therapeutic inhibitor peptide of the invention is a peptide having the amino acid sequence WLRRIKAWLRRIKALNRQLGVAA [SEQ ID NO: 14]. According to another embodiment, the therapeutic inhibitor peptide of the invention is a peptide having the amino acid sequence FAKLAARLYRKALARQLGVAA [SEQ ID NO: 12]. According to another embodiment, the therapeutic inhibitor peptide of the invention is a peptide having the amino acid sequence KAFAKLAARLYRKALARQLGVAA [SEQ ID NO: 15]. According to another embodiment, the therapeutic inhibitor peptide of the invention is a peptide having the amino acid sequence YARAAARQARAKALARQLGVAA [SEQ ID NO: 11]. According to another embodiment, the therapeutic inhibitor peptide of the invention is a peptide having the amino acid sequence YARAAARQARAKALNRQLGVAA [SEQ ID NO: 16]. According to another embodiment, the therapeutic inhibitor peptide of the invention is a peptide having the amino acid sequence YARAAARGQRAKALARQLAVA [SEQ ID NO: 17]. According to another embodiment, the therapeutic inhibitor peptide of the invention is a peptide having the amino acid sequence YARAAARGQRAKALARQLGVA [SEQ ID NO: 18]. According to another embodiment, the therapeutic inhibitor peptide of the invention is a peptide having the amino acid sequence. YARAAARGQRAKALNRQLAVA [SEQ ID NO: 19]. According to another embodiment, the therapeutic inhibitor peptide of the invention is a peptide having the amino acid sequence YARAAARGQRAKALNRQLGVA [SEQ ID NO: 20]. According to another embodiment, the therapeutic inhibitor peptide of the invention is a peptide having the amino acid sequence YARAAARGQRAKALNRQLGVAA [SEQ ID NO: 21].

According to another embodiment, the therapeutic domain of the invention is a domain having the amino acid sequence KALNRQLGVAA [SEQ ID NO: 13]. According to another embodiment, the therapeutic domain of the invention is a domain having the amino acid sequence KAANRQLGVAA [SEQ ID NO: 22]. According to another embodiment, the therapeutic domain of the invention is a domain having the amino acid sequence KALARQLGVAA [SEQ ID NO: 23]. According to another embodiment, the therapeutic domain of the invention is a domain having the amino acid sequence KALNAQLGVAA [SEQ ID NO: 24]. According to another embodiment, the therapeutic domain of the invention is a domain having the amino acid sequence KALNRALGVAA [SEQ ID NO: 25]. According to another embodiment, the therapeutic domain of the invention is a domain having the amino acid sequence KALNRQAGVAA [SEQ ID NO: 26]. According to another embodiment, the therapeutic domain of the invention is a domain having the amino acid sequence KALNRQLAVAA [SEQ ID NO: 27]. According to another embodiment, the therapeutic domain of the invention is a domain having the amino acid sequence KALNRQLGAAA [SEQ ID NO: 28]. According to another embodiment, the therapeutic domain of the invention is a domain having the amino acid sequence KALNRQLGVA [SEQ ID NO: 29]. According to another embodiment, the therapeutic domain of the invention is a domain having the amino acid sequence KKKALNRQLGVAA [SEQ ID NO: 30]. According to another embodiment, the therapeutic domain of the invention is a domain having the amino acid sequence KAAN- RQLGVAA [SEQ ID NO: 22]. According to another embodiment, the therapeutic domain of the invention is a domain having the amino acid sequence KALNAQLGVAA [SEQ ID NO: 24]. According to another embodiment, the therapeutic domain of the invention is a domain having the amino acid sequence KALNRQAGVAA [SEQ ID NO: 26]. According to another embodiment, the therapeutic domain of the invention is a domain having the amino acid sequence KALNRQLGAAA [SEQ ID NO: 28]. According to another embodiment, the therapeutic domain of the invention is a domain having the amino acid sequence KALNRQLGVAA [SEQ ID NO: 13]. According to another embodiment, the therapeutic domain of the invention is a domain having the amino acid sequence KALARQLGVAA [SEQ ID NO: 23]. According to another embodiment the therapeutic domain of the invention is a domain having the amino acid sequence KALNRALGVAA [SEQ ID NO: 25]. According to another embodiment, the therapeutic domain of the invention is a domain having the amino acid sequence KALNRQLAVAA [SEQ ID NO: 27].

According to another embodiment, the PTD of the therapeutic kinase inhibitor peptide is a domain having the amino acid sequence WLRRIKAWLRRIKA [SEQ ID NO: 31]. According to another embodiment, PTD of the therapeutic kinase inhibitor peptide is a domain having the amino acid sequence WLRRIKA [SEQ ID NO: 32]. According to another embodiment, the PTD of the therapeutic kinase inhibitor peptide is a domain having the amino acid sequence YARAAARQARA [SEQ ID NO: 5]. According to another embodiment, the PTD of the therapeutic kinase inhibitor peptide is a domain having the amino acid sequence YGRKKRRQRRR [SEQ ID NO: 33]. According to another embodiment, the PTD of the therapeutic kinase inhibitor peptide is a domain having the amino acid sequence WLRRIKAWLRRI [SEQ ID NO: 34]. According to another embodiment, the PTD of the therapeutic kinase inhibitor peptide is a domain having the amino acid sequence FAKLAARLYR [SEQ ID NO: 35]. According to another embodiment, the PTD of the therapeutic kinase inhibitor peptide is a domain having the amino acid sequence KAFAKLAARLYR [SEQ ID NO: 36]. According to another embodiment, the PTD of the therapeutic kinase inhibitor peptide is a domain having the amino acid sequence YARAAARQARA [SEQ ID NO: 5]. According to another embodiment, the PTD of the therapeutic kinase inhibitor peptide is a domain having the amino acid sequence FAKLAARLYRKA [SEQ ID NO: 43]. According to another embodiment, the PTD of the therapeutic kinase inhibitor peptide is a domain having the amino acid sequence KAFAKLAARLYRKA [SEQ ID NO: 44].

According to another embodiment, the first domain is located 5' to the second domain. According to another embodiment, the second domain is located 3' to the first domain. According to another embodiment, the first domain is operably linked to the second domain. According to another embodiment, the second domain is operably linked to the first domain.

According to another embodiment, the kinase enzyme is mitogen-activated protein kinase-activated protein kinase. According to some such embodiments, the kinase enzyme is MK2. According to some such embodiments, the kinase enzyme is MK3. According to another embodiment, the kinase enzyme is CaMK.

According to some such embodiments, the inflammatory disorder is fibrosis.

According to some such embodiments, the inflammatory disorder is endothelial cell dysfunction.

According to some such embodiments, the inflammatory disorder is endotoxic shock. Endotoxic shock (septic shock) is a condition in which the circulatory system is unable to provide adequate circulation to the body tissues due to the presence of an inflammatory substance. Studies have reported that serum levels of TNF-α determine the fatal or non-fatal course of endotoxic shock (Mozes, T., et al. Immunol. Lett. 27(2):157-62, 1991), while IL-6 levels in patients with septic shock are elevated significantly (Waage, A., et al. J. Exp. Med. 169:333-338, 1989). Symptoms of endotoxic shock include, but are not limited to, mild fever, lack of hunger, mild mental and physical depression, increased heart rate, low pulse pressure, dehydration, and diarrhea.

According to some such embodiments, the inflammatory disorder is pancreatitis. Pancreatitis is inflammation of the pancreas. Acute pancreatitis is sudden while chronic pancreatitis is characterized by recurring or persistent abdominal pain with or without steatorrhea or diabetes mellitus. There is considerable evidence that pro-inflammatory cytokines (e.g., TNF-α, IL-1β) play a central role in the pathophysiology of acute pancreatitis and may mediate the systemic complication of acute pancreatitis by acting as proximal mediators, which induce production of other mediators including IL-6 and IL-8, IL-1β and TNF-α have been implicated as agents leading to progression of disease and IL-6 and IL-8 as indicators of severity (Pooran, N., et al. J. Clin. Gastroenterol. 37(3):263-266, 2003). Symptoms of pancreatitis include, but are not limited to, severe upper abdominal pain, with radiation through to the back, nausea, vomiting, fluctuations in blood pressure (high or low), elevated heart rate, elevated respiratory rate, abdominal tenderness, and the bowel sound may be reduced.

According to some such embodiments, the inflammatory disorder is asthma.

According to some such embodiments, the inflammatory disorder is localized inflammatory disease. Studies have reported that circulating IL-6 and TNF-α play an important role in the induction of a local inflammatory response (Xing, Z. J. Clin. Invest. 101(2):311-320, 1998).

According to some such embodiments, the inflammatory disorder is atherosclerotic cardiovascular disease (atherosclerosis, ASVD). ASVD is a condition in which an artery wall thickens as the result of a build-up of fatty materials, such as cholesterol. It is a syndrome affecting arterial blood vessels (a chronic inflammatory response in the walls of arteries) partially due to the accumulation of macrophage white blood cells and promoted by low-density lipoproteins without adequate removal of fats and cholesterol from the macrophages by functional high density lipoproteins. Studies have implicated IL-1β as a regulatory protein in the development and clinical sequelae of atherosclerosis (Moyer, C. F., et al. Am. J. Pathol. 138(4):951-960. 1991). Additional studies have reported that IL-6 and TNF-α also are associated with atherosclerosis risk factors (Haddy, N., et al. Atherosclerosis. 70(2):277-283. 2003). Symptoms of atherosclerotic cardiovascular disease include, but are not limited to, heart attack, sudden cardiac death (death within one hour of onset of the symptom), peripheral artery occlusive disease, atherogenesis (the developmental process of atheromatous plaques) and stenosis.

According to some such embodiments, the inflammatory disorder is Alzheimer's disease. Alzheimer's disease (AD) is a form of dementia. AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. The cause and progression of AD are not well understood but generally believed to involve neurofibrillary tangles and amyloid-β. Some studies have suggested that the amyloidogenesis in AD results from an IL-1β/IL-6 mediated acute phase reaction in the brain (Vandenabeele, P. and Fiers, W. Immunol. Today. 12(7):217-9. 1991). Additional studies have suggested a correlation between the level of expression of TNF-α and IL-1β and cognitive impairment (Alvarez, X., et al. Mol. Chem. Neuropathol. 29(2-3); 237-252. 1996). Symptoms of AD include, but are not limited to, memory loss, confusion, irritability, aggression, mood swings, and death.

According to some such embodiments, the inflammatory disorder is an oncological disease. Oncological diseases include, but are not limited to, epithelial-derived cancers such as, but not limited to, breast cancer and prostate cancer. According to some embodiments, the disorder is breast cancer. According to some embodiments, the disorder is prostate cancer.

Breast cancer is a cancer that forms in tissues of the breast, usually the ducts (tubes that carry milk to the nipple) and lobules (glands that make milk). There are four stages of breast cancer. Stage 0 (carcinoma in situ) includes lobular carcinoma in situ ("LCIS") and ductal carcinoma in situ ("DCIS"), where the cancerous cells are present in the lining of a lobule or duct, respectively. Stage 1 is an early stage of invasive breast cancer where the tumor is no more than 2 cm across and the cancer cells have not spread beyond the breast. In Stage II, the tumor is either (i) no more than 2 cm in diameter and the cancer has spread to the lymph nodes under the arm; (ii) between 2-4 cm in diameter and the cancer may have spread to the lymph nodes under the arm; or (iii) the cancer is larger than 5 cm in diameter and the cancer has not spread to the lymph nodes under the arm. Stage III may be a large tumor, but the cancer has not spread beyond the breast and nearby lymph nodes. It is locally advanced cancer. In Stage IIIA, the tumor may or may not be smaller than 5 cm in diameter and has spread to the lymph nodes under the arm. In Stage IIIB, the tumor has grown into the chest wall or the skin of the breast and the cancer has spread to the lymph nodes behind the breastbone. In Stage IIIC, the tumor is of any size and has spread to the lymph nodes under the arm, behind the breastbone, and under or above the collarbone. Stage IV is distant metastatic cancer where the cancer has spread to other parts of the body. Studies have reported that IL-6 levels are elevated in patients with metastatic breast cancer (Zhang, G I, and Adachi, I. Anticancer Res. 19(2B):1427-1432, 1999) and that TNF-α can potentiate the ability of IL-6 to stimulate estrogen synthesis in breast tumors (Reed, M. J., and Purohit, A. Endocrine Rev. 18(5):701-715, 1997). Additional studies have reported that tumor-associated IL-1β is present in the tumor microenvironment and may play a pivotal role in regulating breast tumor growth and metastasis (Kurtzman, S. H., et al, Oncology Reports. 6(1):65-70, 1998).

Prostate cancer is a cancer that forms in tissues of the prostate (a gland in the male reproductive system found below the bladder and in front of the rectum). There are four stages of prostate cancer. In Stage 1, the cancer cannot be felt during a digital rectal exam, and it cannot be seen on a sonogram. It is found by chance when surgery is performed for another reason. The stage 1 cancer is only in the prostate and the grade is G1 (or the Gleason score is no higher than 4). In Stage II, the tumor is more advanced or a higher grade than Stage 1, but the tumor does not extend beyond the prostate. It may be felt during a digital rectal exam, or it may be seen on a sonogram. In Stage III, the tumor extends beyond the prostate and may have invaded the seminal vesicles, but has not yet spread to the lymph nodes. In Stage IV, the tumor may have invaded the bladder, rectum, or nearby structures (beyond the seminal vesicles). It may have spread to the lymph nodes, bones or to other parts of the body. Studies have reported that serum levels of IL-6 and TNF-α, were significantly higher in patients with metastatic disease than those in patients with localized disease, and that levels of both cytokines were directly correlated to the extent of the disease (Michalaki, V., et al. Br. J. Cancer. 90(12):2312-6, 2004). Additional studies have reported that IL-1β is required for in vivo angiogenesis and invasiveness of different tumor cells (Voronov, E., et al., Proc. Natl. Acad. Sci. USA. 100(5):2645-2650, 2003). A man with prostate cancer may not have any symptoms. For men who do have symptoms, the common symptoms include, but are not limited to, urinary problems, impotence, blood in the urine or semen, and frequent pain in the lower back, hips or upper thighs.

According to some such embodiments, the inflammatory disorder is ischemia. Ischemia is a restriction in blood supply, generally due to factors in blood vessels, with resultant tissue dysfunction. Studies have reported that levels of IL-6, IL-1β and TNF-α are increased during the early recirculation period after ischemia (Saito, K., et al. Neurosci. Lett. 206(2-3):149-152, 1996). Symptoms of ischemia include, but are not limited to, a shortage of oxygen and glucose in the blood supply. According to some such embodiments, the disorder is neural ischemia.

According to some such embodiments, the inflammatory disorder is rheumatoid arthritis (RA). According to some such embodiments, the inflammatory disorder is Crohn's disease. According to some such embodiments, the inflammatory disorder is inflammatory bowel disease.

According to some such embodiments, the inflammatory disorder is intimal hyperplasia. Intimal hyperplasia is a thickening of the Tunica intima (the innermost layer of an artery or vein) of a blood vessel as a complication of a reconstruction procedure or endarterectomy (the surgical stripping of a fat-encrusted, thickened arterial lining so as to open or widen the artery for improved blood circulation). It involves the coordinated stimulation of smooth muscle cells by mechanical, cellular and humoral factors to induce a program of cellular activation that leads to proliferation, migration and extracellular matrix deposition. Intimal hyperplasia is the universal response of a vessel to injury. Studies have reported that the overexpression of IL-6, as regulated by IL-1β and TNF-α, plays an important role in atheroma-associated cells (Kornman, K. et al. J. Perio. Res. 34(7):353-357. 2006; Libby, P., et al. Circulation. 86(6 Suppl):III47-52. 1992)).

According to some such embodiments, the inflammatory disorder is stenosis. Stenosis is the abnormal narrowing in a blood vessel or other tubular organ or structure. The resulting syndrome depends on the structure affected. Studies have reported that the overexpression of IL-6, as regulated by IL-1β and TNF-α, plays an important role in atheroma-associated cells (Id). Symptoms of stenosis may include, but are not limited to, cyanosis (blue coloration of the skin and mucous membranes, atrophic changes such as loss of hair and shiny skin, decreased body temperature, decreased pulse, paraesthesia, and paralysis. According to some such embodiments, the disorder is restenosis (reoccurrence of stenosis).

According to some such embodiments, the inflammatory disorder is smooth muscle cell tumors and metastasis. Several smooth muscle cell tumors, and the metastasis thereof, have been studied. These include leiomyoma. These neoplasms generally are benign smooth muscle neoplasms that are not premalignant and that can occur in any organ, such as the uterus, small bowel and the esophagus. Uterine fibroids are leiomyomata of the uterine smooth muscle. Although benign, uterine fibroids may lead to excessive menstrual bleeding, anemia and infertility. Leiomyomas of the skin include solitary cutaneous leiomyoma, multiple cutaneous (or pilar) leiomyomas arising from the arrectores pilorum muscles, angioleiomyomas (vascular leiomyomas), dartoic (or genital) leiomyomas originating in the dartos muscles of the genitalia, areola and nipple, and angiolipoleiomyoma. Studies have reported that the uterine cavity in leiomyoma, adenomyosis and endometrial polyp group contains elevated levels of cytokines, such as IL-1β and TNF-α (Inagaki, N., et al. Eur. J. Obst. Gyn. 111(2):197-203, 2003). Additional studies have reported that IL-6 also is expressed in leiomyoma (Luo, X et al., Endocrinology. 146(3):1097-1118, 2005).

According to some such embodiments, the inflammatory disorder is smooth muscle spasm. A smooth muscle spasm is the sudden, involuntary contraction of a smooth muscle (or group of muscles). Studies have reported that the vascular reactivity in resistance arteries is related to the balance between IL-1β, IL-6 and TNF-α (Vila, E. and Salaices, M. Am. J. Physiol. Heart Circ. Physiol. 288:H1016-H1021, 2005).

According to some such embodiments, the inflammatory disorder is angina (angina pectoris). Angina is severe chest pain due to myocardial ischemia. Studies have reported that elevated levels of IL-6 are common in unstable angina and are associated with poor prognosis (Biasucci, L., et al. Circulation. 94: 874-877. 1996). Additionally, studies have reported an association between the level of expression of IL-6 and TNF-α with coronary mortality (Koukkunen, H., et al. Annals Med. 33(1):37-47. 2001). Symptoms of angina include, but are not limited to, chest discomfort, chest pain, a pressure, heaviness, tightness, squeezing, burning or choking sensation in the chest, epigastrium, pain in the back, pain in the neck area, pain in the jaw, pain in the shoulders, nausea, vomiting, and pallor.

According to some such embodiments, the inflammatory disorder is Prinzmetal's angina (variant angina). Prinzmetal's angina occurs in patients with normal coronary arteries or insignificant atherosclerosis. Symptoms include, but are not limited to, those of angina, and typically occur at rest (rather than during exertion) in cycles.

According to some such embodiments, the inflammatory disorder is bradycardia (bradyarrhythmia). Bradycardia refers to a resting heart rate of under 60 beats per minute. Studies have reported that increased levels of IL-1β, IL-6 and TNF-α are associated with bradycardia (Fukuhara, Y., et al. Toxicol. 41(1):49-55. 2003). According to some such embodiments, the inflammatory disorder is bradyarrhythmia.

According to some such embodiments, the inflammatory disorder is hypertension. Hypertension refers to elevated blood pressure (high blood pressure). Studies have reported that increased levels of IL-1β, IL-6 and TNF-α are associated with bradycardia (Fukuhara, Y., et al. Toxicol. 41(1):49-55. 2003). Symptoms of hypertension include, but are not limited to, headache, somnolence, confusion, visual disturbances, nausea, vomiting, seizure, irritability, and respiratory distress.

According to some such embodiments, the inflammatory disorder is cardiac hypertrophy (heart enlargement). Ventricular hypertrophy is the enlargement of ventricles in the heart. Ventricular hypertrophy generally is associated with pathological changes due to hypertension (or other disease states). Studies have reported that IL-1β and TNF-α are sufficient to stimulate hypertrophic growth responses and have suggested that overexpression of IL-6 may lead to cardiac hypertrophy (Yokoyama, T., et al. Circulation. 95:1247-1252. 1997). Symptoms of cardiac hypertrophy may include, but are not limited to, headache, somnolence, confusion, visual disturbances, nausea, vomiting, seizure, irritability, and respiratory distress.

According to some such embodiments, the inflammatory disorder is renal failure. Renal failure (kidney failure) results when the kidneys fail to function adequately. Studies have reported the association of IL-1β and TNF-α (Descamps-Latscha, B., et al. J. Immunol. 154(2):882-892. 1995) and of increased IL-6 (Herbelin, A., et al. Kidney Internat'l. 39:954-960. 1991) with renal failure. Symptoms of renal failure include, but are not limited to, high levels of urea in the blood, accumulation of phosphates in the blood, nausea, vomiting, weight loss, nocturnal urination, itching, abnormal heart rhythms, swelling of the legs, ankles or feet, and pain the back or side.

According to some such embodiments, the inflammatory disorder is stroke. A stroke is the loss of brain function due to disturbance in the blood supply to the brain. Studies have reported that serum levels of IL-6 and TNF-α increase after stroke (Ferrarese, C., et al. J. Cerebral Blood Flow Metabol. 19:1004-1009, 1999) and that the level of expression of IL-1β is upregulated after focal brain ischemia (Wang, X., et al. Stroke. 28:155-162, 1997). Symptoms of stroke include, but are not limited to, hemiplagia, numbness, reduction in sensory or vibratory sensation, altered smell, drooping of eyelids, balance problems, aphasia, apraxia, memory deficits and vertigo.

According to some such embodiments, the inflammatory disorder is pulmonary hypertension. Pulmonary hypertension refers to an increase in blood pressure in the pulmonary artery, pulmonary vein, or pulmonary capillaries. Studies have reported that TNF-α levels are elevated, with no differences in the serum levels of IL-6, in patients with pulmonary hypertension (Joppa, P., et al. Chest. 130(2):326-333. 2006). Symptoms of pulmonary hypertension include, but are not limited to, shortness of breath, dizziness, fainting, peripheral edema, and heart failure.

According to some such embodiments, the inflammatory disorder is toxemia of pregnancy. Toxemia of pregnancy (hypertensive disorder of pregnancy) collectively refers to pre-eclampsia and eclampsia. According to some such embodiments, the inflammatory disorder is pre-eclampsia. Pre-eclampsia is a condition where hypertension arises in pregnancy in association with significant amounts of protein in the urine. Studies have reported that the plasma levels of IL-6 and TNF-α was increased in women with preeclampsia compared with those in normal third-trimester pregnancies (Conrad, K. et al. Am. J. Repro. Immunol. 40(2):102-111, 1998). Further, the levels of IL-1β appeared unchanged between the subject groups (Id.). Symptoms include, but are not limited to, elevated blood pressure, generalized damage to the maternal endothelium, kidneys, and liver. According to some such embodiments, the inflammatory disorder is eclampsia. Eclampsia is characterized by the appearance of tonic-clonic (grand mal) seizures. According to some such embodiments, the inflammatory disorder is pre-term labor.

According to some such embodiments, the inflammatory disorder is Raynaud's disease/phenomenon. Raynaud's disease is a vascular disorder that affects blood flow to the extremities (the fingers, toes, nose and ears) when exposed to cold temperatures or in response to psychological stress. Studies have reported that IL-6 and TNF-α (Rychlik, W., et al., Int. Angiol. 25(4):436. 2006) play a role in the pathogenesis of Raynaud's phenomenon. Symptoms of Raynauds's disease include, but are not limited to, cyanosis, and pallor.

Raynoud's disease is diagnosed if the symptoms are idiopathic, while Raynoud's phenomenon occurs secondary to a wide variety of other conditions, such as, but not limited to, connective tissue disorders, systemic lupos erythematosus, arthritis, and other rheumatic diseases.

According to some such embodiments, the inflammatory disorder is hemolytic-uremia. Studies have reported that TNF-α and IL-1 play important roles in the induction of the inflammatory mediator verocytotoxin-1 during hemolytic uremic syndrome (van de Kar, N. C., et al. Blood. 80(11): 2755-2764, 1992). Additional studies have reported that levels of IL-6 also become elevated (Karpman, D., et al. Ped. Nephrol. 9(6):694-699, 1995). Hemolytic uremia is a disease characterized by hemolytic anemia (abnormal breakdown of red blood cells), acute renal failure (uremia) and low platelet count (thrombocytopenia).

According to some such embodiments, the inflammatory disorder is anal fissure. An anal fissure is a natural crack or tear in the skin of the anal canal. Most anal fissures are caused by stretching of the anal mucosa beyond its capability. Superficial or shallow anal fissures generally will self-heal. Some anal fissures become chronic and deep and will not heal. The most common cause of non-healing is spasming of the internal anal sphincter muscle which results in impaired blood supply to the anal mucosa. Studies have reported that rectal mucosal IL-10, IL-6 and serum IL-6 and TNF-α were higher in patients with perianal Crohn's disease, than in patients with small bowel Crohn's disease and healthy controls (Ruffolo, C., et al. Infl. Bowel Dis. 14(10):1406-1412, 2008).

According to some such embodiments, the inflammatory disorder is achalasia. Achalasia (esophageal achalasia, achalasia cardiae, cardiospasm, esophageal aperistalsis) is an esophageal motility disorder. The smooth muscle layer of the esophagus loses normal peristalsis and the lower esophageal sphincter fails to relax properly in response to swallowing. Studies have reported that IL-6 and IL-1β are produced in significantly greater amounts in the mucose of esphagitis patients compared to those of control patients (Rieder, F., et al. Gastroenterol. 132(1):154-165, 2007). Symptoms include, but are not limited to, dysphagia, regurgitation, weight loss, coughing and chest pain.

According to some such embodiments, the inflammatory disorder is impotence. Erectile dysfunction (ED) is a sexual dysfunction characterized by the inability to develop or maintain an erection of the penis. An erection occurs as a hydraulic effect due to blood entering and being retained in sponge-like bodies within the penis. Studies have reported that increased blood levels of IL-6, IL-1β and TNF-α in ED patients correlated negatively with sexual performance (Vlachopoulos, C., et al. Eur. Heart. J. 27(22):2640-2648. 2006). ED may be a symptom of cardiovascular disease.

According to some such embodiments, the inflammatory disorder is migraine. A migraine is a neurological syndrome characterized by severe headaches, nausea and altered bodily perceptions. Studies have reported increased serum levels of IL-6 and TNF-α during migraine attacks (Peterlin, B., et al, Cephalagia. 27(5):435-446. 2007). A migraine headache is unilateral and pulsating, lasting from 4 hours to 72 hours; symptoms include, but are not limited to, nausea, vomiting, photophobia, and phonophobia.

According to some such embodiments, the inflammatory disorder is ischemic muscle injury associated with smooth muscle spasm. Studies have reported that IL-1, IL-6 and TNF-α cause a negative inotropic effect and induce apoptosis in myocardium subjected to ischemia-reperfusion (Saini, H. K., et al. Exp. Clin. Cardiol. 10(4):213-222, 2005).

According to some such embodiments, the inflammatory disorder is vasculopathy. Vasculopathy refers to a heterogeneous group of disorders characterized by inflammatory destruction of blood vessels. Both arteries and veins may be affected. Studies have reported that IL-6 is an important risk factor for cardiac transplant related coronary vasculopathy (Densem, C., et al, J. Heart Lung Transpl. 24(5):559-565. 2005). Symptoms of vasculopathy include, but are not limited to, fever, weight loss, purpura, livedo reticularis, myalgia or myositis, arthralgia or arthritis, mononeuritis multiplex, headache, stroke, tinnitus, reduced visual acuity, acute visual loss, myocardial infarction, hypertension, gangrene, nose bleeds, bloody cough, lung infiltrates, abdominal pain, bloody stool, and glomerulonephritis.

According to some such embodiments, the inflammatory disorder is congestive heart failure (CHF). Congestive heart failure is a condition in which the heart is unable to maintain an adequate circulation of blood in the body. Studies have reported that patients with CHF have increased levels of IL-6 and TNF-α when compared to normal healthy subjects (Aukrust, P. et al. Am. J. Cardiol. 83(3):376-382. 1999). Typical symptoms of CHF include, but are not limited to, shortness of breath, cough, swelling of feet and ankles, swelling of the abdomen, weight gain, irregular or rapid pulse, fatigue, weakness, arrhythmias, anemia, and hyperthyroidism.

According to some such embodiments, the inflammatory disorder is stunned or hibernating myocardium. The term "chronic myocardial ischemia (CMI)" as used herein refers to a prolonged subacute or chronic state of myocardial ischemia due to narrowing of a coronary blood vessel in which the myocardium "hibernates", meaning that the myocardium downregulates or reduces its contractility, and hence its myocardial oxygen demand, to match reduced perfusion, thereby preserving cellular viability and preventing myocardial necrosis. This hibernating myocardium is capable of returning to normal or near-normal function on restoration of an adequate blood, supply. Once coronary blood flow has been restored to normal or near normal and ischemia is resolved, however, the hibernating myocardium still does not contract, This flow-function mismatch resulting in a slow return of cardiac function after resolution of ischemia has been called stunning. The length of time for function to return is quite variable, ranging from days to months, and is dependent on a number of parameters, including the duration of the original ischemic insult, the severity of ischemia during the original insult, and the adequacy of the return of the arterial flow. A number of studies have provided evidence for inflammation in hibernating myocardium. Heusch, G. et al., Am. J. Physiol, Heart Circ. Physiol. 288: 984-99 (2005). Studies also have reported that proinflammatory cytokines such as IL-6 and TNF-α are elevated after uncomplicated coronary revascularization and may contribute to postoperative myocardial ischemia and segmental wall abnormalities (Rankin, J. J. Thorac. Cardiovas. Surg. 108:626-35. 1994).

According to some such embodiments, the inflammatory disorder is diastolic dysfunction. Diastolic dysfunction refers to an abnormality in the heart's (i.e., left ventricle) filling during diastole. Diastole is that phase of the cardiac cycle when the heart (i.e., ventricle) is not contracting but is actually relaxed and filling with blood that is being returned to it, either from the body (into right ventricle) or from the lungs (into left ventricle). Studies have implicated IL-6, IL-1β and TNF-α in mediating myocardial depression in systemic sepsis and other forms of cardiac dysfunction (Kelly, R., and Smith, T. W. Circulation. 95:778-781, 1997). Symptoms include, but are not limited to, pulmonary edema, hypertension, aortic stenosis, scarred heart tissue, and diabetes.

According to some such embodiments, the inflammatory disorder is gliosis (meaning a proliferation of astrocytes, which may include deposition of extracellular matrix (ECM) in damaged areas of the central nervous system). Studies have reported that IL-1 and IL-6 boost glial scar formation, while TNF-α, which does not induce IL-6 release, does not induce gliosis (Woiciechowsky, C., et al. Med. Sci. Monit. 10(9): BR325-330. 2004).

According to some such embodiments, the inflammatory disorder is chronic obstructive pulmonary disease (COPD) (meaning respiratory tract diseases characterized by airflow obstruction or limitation; which includes, but is not limited to, chronic bronchitis and emphysema). Increased levels of IL-6, IL-1β and TNF-α have been measured in sputum of patients with COPD (Chung, K. Eur. Respir. J. 18:50s-59S, 2001).

According to some such embodiments, the inflammatory disorder is osteopenia. Osteopenia is a condition where bone mineral density (which indicates how dense and strong the bone is) is lower than that of a normal healthy subject but not low enough to be classified as osteoporosis. Osteopenia may be defined as a bone mineral density T score between −1.0 and −2.5 as measured by dual-energy X-ray absorptiometry (DEXA). Studies have reported that IL-1β, IL-6 and TNF-α play a role in the induction of bone resorption (Rifas, L. Calcif. Tissue Int. 64:1-7. 1999).

According to some such embodiments, the inflammatory disorder is degenerative arthritis (osteoarthritis, OA). Osteoarthritis is a type of arthritis that is caused by the breakdown and eventual loss of cartilage of one or more joints. Osteoarthritis commonly affects the hands, feet, spine and large weight-bearing joints such as the hips and knees. Studies have reported that chronic inflammatory changes with production of proinflammatory cytokines (IL-1α, IL-1β, TNF-α) are a feature of synovial membranes from patients with early OA (Smith, M. D., et al., J. Rhematol. 24(2):365-371, 1997). Symptoms of osteoarthritis include, but are not limited to, pain in the affected joint(s) after repetitive use, swelling, warmth, and creaking of the affected joint(s).

According to some such embodiments, the inflammatory disorder is ankylosing spondylitis. According to some such embodiments, the inflammatory disorder is Sjogren's disease. According to some such embodiments, the inflammatory disorder is Guilliamé-Barre syndrome. According to some such embodiments, the inflammatory disorder is scleroderma.

According to some such embodiments, the inflammatory disorder is sepsis. Sepsis is a condition characterized by a whole-body inflammatory state (systemic inflammatory response syndrome (SIRS)), and the presence of a known or suspected infection. The body may develop this inflammatory response to microbes in the blood, urine, lungs, skin or other tissues. Studies have implicated IL-6 and TNF-α as key mediators in inflammation, morbidity, and mortality associated with sepsis (Leon, L, et al. Am. J. Physiol. Regul. Integr. Comp. Physiol. 275:R269—R277. 1998). Symptoms of sepsis include, but are not limited to, acute inflammation present throughout the entire body, fever, elevated white blood cell count, nausea and vomiting, elevated heart rate, and increased respiratory rate. According to some such embodiments, the disorder is endotoxemic shock. Septicemia is a systemic illness with toxicity due to invasion of the bloodstream by virulent bacteria coming from a local seat of infection. Symptoms include, but are not limited to, chills, fever, and fatigue.

According to some such embodiments, the inflammatory disorder is psoriasis.

According to some such embodiments, the inflammatory disorder is radiation enteritis. Radiation enteropathy (radiation enteritis) is an inflammation (swelling) of the lining of the small intestine due to radiation therapy. Studies have reported that levels of IL-1β and TNF-α mRNA increase after irradiation, and that expression of IL-6 becomes elevated (Linard, C., et al. Int. J. Rad. Oncol. Biol. Phy. 58(2):427-434. 2004). Symptoms of radiation enteritis include, but are not limited to, anorexia, diarrhea, nausea, vomiting and weight loss.

According to some such embodiments, the inflammatory disorder is cirrhosis. Cirrhosis is scarring of the liver and poor liver function as a result of chronic liver disease (CLD). Studies have reported that serum levels of IL-1β, TNF-α and IL-6 were elevated in patients with chronic liver disease, and that a cirrhotic group of CLD patients showed higher serum levels of IL-1β, IL-6 and TNF-α than did the noncirrhotic cases (Tilg, H., et al. Gastroenterology. 103(1):264-74. 1992). Symptoms of cirrhosis include, but are not limited to, bleeding hemorrhoids, confusion, impotence, jaundice, nausea and vomiting, weight loss, bloating, abdominal indigestion, fevers, abdominal pain, and decreased urine output.

According to some such embodiments, the inflammatory disorder is interstitial fibrosis, Interstitial lung disease, or ILD, includes more than 180 chronic lung disorders, which may be chronic, nonmalignant (non-cancerous), and noninfectious. Interstitial lung diseases are named for the tissue between the air sacs of the lungs called the interstitium, which is the tissue affected by fibrosis (scarring). Interstitial lung diseases also may be called interstitial pulmonary fibrosis or pulmonary fibrosis. Studies have reported that high levels of expression of IL-1β is accompanied by a local increase of IL-6 and INF-α and a vigorous acute inflammatory tissue response with evidence of tissue injury (Kolb, M., et al. J. Clin. Invest. 107(12):1529-1536, 2001). The symptoms and course of each of these diseases may vary from person to person, but the common link between the many forms of ILD is that they all begin with an inflammation, e.g., bronchiolitis (inflammation that involves the bronchioles (small airways)); alveolitis (inflammation that involves the alveoli (air sacs)); or vasculitis (inflammation that involves the small blood vessels (capillaries)). More than 80 percent of interstitial lung diseases are diagnosed as pneumoconiosis, a drug-induced disease, or hypersensitivity pneumonitis. The other types are sarcoidosis; idiopathic pulmonary fibrosis; bronchiolitis obliterans; histiocytosis X; chronic eosinophilic pneumonia; collagen vascular disease; granulomatous vasculitis; Goodpasture's syndrome, and pulmonary alveolar proteinosis.

According to some such embodiments, the inflammatory disorder is colitis. Colitis is inflammation (swelling) of the large intestine (colon). Colitis can have many different causes such as, for example, acute and chronic infections, inflammatory disorders (ulcerative colitis, Crohn's disease, lymphocytic and collagenous colitis), lack of blood flow (ischemic colitis) and past radiation of the large bowel. Studies have reported that inhibition of TNF-α in animal models of colitis leads to reduced levels of IL-1 and IL-6 and reduced severity of colitis (Neurath, M., et al. Eur. J. Immunol. 27(7): 1743-1750, 2005). Symptoms of colitis include, but are not limited to, abdominal bleeding, abdominal pain, bloody stools, dehydration, diarrhea and increased intestinal gas.

According to some such embodiments, the inflammatory disorder is appendicitis. Appendicitis is inflammation of the appendix. The appendix is a small pouch attached to the large intestine. Studies have reported that elevated levels of IL-6 show the best trend in the diagnosis of acute appendicitis (Paajanen, H., et al. Scan. J. Clin. Lab. Invest. 62(8):579-584, 2002). Additional studies have reported that TNF-α is present along with low levels of IL-6 in the peritoneal fluid of patients with appendicitis (Fernando, A., et al. Ann. Surg. 237(3):408-416, 2003). Symptoms of appendicitis include, but are not limited to, abdominal pain, fever, reduced appetite, nausea, vomiting, chills, and constipation.

According to some such embodiments, the inflammatory disorder is gastritis. Gastritis is an inflammation of the lining of the stomach. Common causes of gastritis include, for example, alcohol, smoking, and bacterial infection. Studies have reported that the production of TNF-α and IL-6 by human gastral mucosa was significantly greater in patients infected with *Helicobacter pylori*, all of whom had chronic gastritis, than in patients who were *H. pylori* negative with histologically normal gastric mucosa (Crabtree, J., et al. Gut. 32:1473-1477, 1991). Symptoms of gastritis include, but are not limited to, abdominal pain, abdominal indigestion, dark stools, loss of appetite, nausea, vomiting, and vomiting blood or coffee-ground like material.

According to some such embodiments, the inflammatory disorder is laryngitis. Laryngitis is inflammation of the larynx (voice box). Laryngitis usually is associated with hoarseness of loss of voice. The larynx is located at the top of the trachea and contains the vocal cords. When the vocal cords become inflamed or infected, they swell. This can cause hoarseness, and may sometimes block the airway. Studies have reported that IL-6 and TNF-α are increased in cases where laryngitis is induced by nasogastric intubation (Lima-Rodrigues, M., et al. Larynscope. 118(1):78-86. 2008). Symptoms of laryngitis include fever, hoarseness, and swollen lymph nodes or glands in the neck.

According to some such embodiments, the inflammatory disorder is meningitis. Meningitis is inflammation of the membranes covering the brain and spinal cord that affects the cerebrospinal fluid. Studies have reported that recombinant forms of IL-6 and TNF-α can induce meningitis or blood brain barrier injury, and suggest that in situ generation of IL-1 within cerebral spinal fluid (with or without TNF) is capable of mediating both meningeal inflammation and the blood brain barrier injury seen in various central nervous system infections (Quagliarello, V., et al. J. Clin. Invest. 87(4):1360-1366, 1991). Symptoms of meningitis include, but are not limited to, fever and chills, mental status changes, nausea and vomiting, photophobia, severe headache, meningismus, agitation, and rapid breathing.

According to some such embodiments, the inflammatory disorder is otitis. Otitis refers to infection or inflammation of the ear. Otitis can affect the inner or outer parts of the ear. The condition is classified according to whether it occurs suddenly and for a short time (acute) or repeatedly over a long period of time (chronic). Studies have reported that levels of IL-1β and TNF-α become elevated in animal models of otitis media (Sato, K., et al. Ann. Otol. Rhinol. Laryngol. 108(6):559-63, 1999). Additional studies have reported elevated levels of IL-6 in patients with otitis media with effusion (Jang, C. and Kim, Y. Int. J. Ped. Otorhinol. 66(1):37, 2002). Symptoms include, but are not limited to, chills, diarrhea, drainage from the ear, earache, ear noise or buzzing, fever, hearing loss, irritability, nausea and vomiting.

According to some such embodiments, the inflammatory disorder is reperfusion injury.

According to some such embodiments, the inflammatory disorder is traumatic brain injury. A traumatic brain injury is caused by a blow or jolt to the head or by a penetrating head injury that disrupts the normal function of the brain. Not all blows or jolts to the head result in a traumatic brain injury. The severity of the traumatic brain injury may range from "mild" (a brief change in mental status or consciousness) to severe (an extended period of unconsciousness or amnesia after the injury). Studies have reported that levels of both IL-6 and TNF-α become elevated in patients with severe traumatic brain injury (Csuka, E., et al. J. Neuroimmunol. 101(2):211-21, 1999), Symptoms of traumatic brain injury include, but are not limited to, headaches or neck pain, difficulty remembering, concentrating or making decisions, fatigue, mood changes, nausea, photophobia, blurred vision, ringing in the ears, and loss of sense of taste or smell.

According to some such embodiments, the inflammatory disorder is spinal cord injury. Spinal cord trauma or injury is damage to the spinal cord that may result from direct injury to the cord itself or indirectly from damage to surrounding bones, tissues, or blood vessels. Studies have reported that the levels of expression of TNF-α, IL-6 and IL-1β become elevated in injured spinal cord (Hayashi, M., et al, J. Neurotrauma. 17(3):203-18, 2000). Symptoms of spinal cord injury include, but are not limited to, weakness and sensory loss at and below the point of injury, breathing difficulties, loss of normal bowel and bladder control, numbness, spasticity, and pain.

According to some such embodiments, the inflammatory disorder is peripheral neuropathy. The term "peripheral neuropathy" refers to damage to the peripheral nervous system. It has been reported that IL-6 is overexpressed after experimental axotomy and that IL-1 and TNF-α levels progressively increase after injury (nerve crush) (Creange, A., et al. Eur. Cytokine Network. 8(2):145-51, 1997). Symptoms are related to the type of affected nerve and may be seen over a period of days, weeks or years. Muscle weakness is the most common symptom of motor nerve damage. Other symptoms may include painful cramps and fasciculations (uncontrolled muscle twitching visible under the skin), muscle loss, bone degeneration and changes in skin, hair and nails. Sensory nerve damage causes a more complex range of symptoms because sensory nerves have a wider, more highly specialized range of functions. Larger sensory fibers enclosed in myelin register vibration, light touch, and position sense. Damage to large sensory fibers lessens the ability to feel vibrations and touch, resulting in a general sense of numbness, especially in the hands and feet. Smaller sensory fibers without myelin sheaths transmit pain and temperature sensations. Symptoms of autonomic nerve damage are diverse and depend upon which organs or glands are affected. Common symptoms of autonomic nerve damage include an inability to sweat normally, which may lead to heat intolerance; a loss of bladder control, which may cause infection or incontinence; and an inability to control muscles that expand or contract blood vessels to maintain safe blood pressure levels. A loss of control over blood pressure can cause dizziness, lightheadedness, or even fainting when a person moves suddenly from a seated to a standing position (a condition known as postural or orthostatic hypotension). Gastrointestinal symptoms frequently accompany autonomic neuropathy. Nerves controlling intestinal muscle contractions often malfunction, leading to diarrhea, constipation, or incontinence.

According to some such embodiments, the inflammatory disorder is multiple sclerosis. According to some such embodiments, the inflammatory disorder is Lupus (systemic lupus erythematosus).

According to some such embodiments, the inflammatory disorder is cardiometabolic syndrome. Cardiometabolic syndrome (Syndrome X, CMS) is defined as the presence of any three of the following conditions: (i) excess weight around the waist; (ii) high levels of triglycerides; (iii) low levels of HDL (good cholesterol); (iv) high blood pressure; and (v) high fasting blood glucose levels. The growing prevalence of CMS has been related to obesity, which has increased among many age groups. It currently is accepted that CMS predicts cardiovascular mortality and/or the development of type 2 diabetes mellitus. CMS is further complicated by modifications in body composition and fat redistribution and often is associated with altered insulin sensitivity. Many people with diabetes have several of these conditions at the same time. According to some such embodiments, the inflammatory disorder is obesity. Obesity has been defined by the National Institutes of Health (NIH) as a body mass index (BMI) of 30 and above. Body Mass Index is a standardized ratio of weight to height, and often is used as a general indicator of health. BMI can be calculated by dividing weight (in kilograms) by the square of height (in meters). A BMI between 18.5 and 24.9 is considered normal for most adults. According to some such embodiments, the inflammatory disorder is type II diabetes mellitus. Type 2 diabetes (non-insulin-dependent diabetes mellitus (NIDDM), adult onset diabetes) is a metabolic disorder that is primarily characterized by insulin resistance (cells do not respond appropriately when insulin is present), relative insulin deficiency and hyperglycemia. IL-6 not only impairs insulin sensitivity, but also is a major determinant of hepatic production of C-reactive protein (the most important source of this inflammatory marker). A study in type 2 diabetes patients showed that circulating levels of IL-6 correlate strongly with visceral fat area (VFA), and that the stiffness of the carotid artery (an index of atherosclerosis) correlated with both VFA and with levels of IL-6 and C-reactive protein, suggesting that intra-abdominal adipocyte-derived IL-6 could be involved in the accelerated atherosclerosis of type 2 diabetes patients (Despres, J. Eur. Heart J. Suppl. 8(B):B4-B12, 2006). Symptoms of type 2 diabetes include, but are not limited to, polyuria and polydispia.

According to some such embodiments, the inflammatory disorder is type I diabetes mellitis.

According to some such embodiments, the inflammatory disorder is non-alcoholic steatohepatitis (NASH). NASH is fatty inflammation of the liver when not due to excessive alcohol use. In NASH, fat builds up in the liver and eventually causes scar tissue. NASH can lead to cirrhosis. Studies report that TNF-α levels are increased in patients with NASH (Bahceicoglu, H., et al. Hepatoenterology. 52(65):1549-53, 2005). Additional studies have reported elevated IL-6 levels (Kugelmas, M., et al. Hepatology. 38(2):413-9, 2003) and IL-1β levels (Brun, P., et al. Am. J. Physiol. Gastrointest. Liver Physiol. 292:G518-G525, 2007) in NASH patients. Symptoms of NASH include, but are not limited to, fatigue, malaise, and dull right-upper quadrant abdominal discomfort.

According to another embodiment, the therapeutic domain of the therapeutic inhibitor peptide is a domain having substantial identity to the amino acid sequence KALNRQLGVAA [SEQ ID NO: 13].

According to another embodiment, the therapeutic domain of the therapeutic inhibitor peptide is a domain having substantial identity to the amino acid sequence KALARQLGVAA [SEQ ID NO: 23].

According to another embodiment, the protein transduction domain of the therapeutic inhibitor peptide is a domain having substantial identity to the amino acid sequence WLRRIKAWLRRIKA [SEQ ID NO: 31].

According to another embodiment, the protein transduction domain of the therapeutic inhibitor peptide is a domain having substantial identity to the amino acid sequence WLRRIKAWLRRI [SEQ ID NO: 34].

According to another aspect, the described invention provides an isolated nucleic acid that encodes a polypeptide having at least 85% amino acid sequence identity to a therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 86% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 87% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 88% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 89% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 90% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 91% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 92% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 93% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 94% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 95% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 96% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 97% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 98% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the isolated nucleic acid encodes a polypeptide having at least 99% amino acid sequence identity to the therapeutic inhibitor peptide, wherein the therapeutic inhibitor peptide is a peptide having the amino acid sequence WLRRIKAWLRRIKALNRQLGVAA [SEQ ID NO: 14], wherein the polypeptide inhibits kinase activity of a kinase enzyme. In some such embodiments, the therapeutic inhibitor peptide having the amino acid sequence WLRRIKAWLRRIKALNRQLGVAA [SEQ ID NO: 14] sequence is operably linked to a controllable regulatory element. According to another embodiment, the therapeutic inhibitor peptide is a peptide having the amino acid sequence WLRRIKAWLRRIKALNRQLGVAA [SEQ ID NO: 14]. According to another embodiment, the therapeutic inhibitor peptide is a peptide having the amino acid sequence FAKLAARLYRKALARQLGVAA [SEQ ID NO: 12]. According to another embodiment, the therapeutic inhibitor peptide is a peptide having the amino acid sequence KAFAKLAARLYRKALARQLGVAA [SEQ ID NO: 15]. According to another embodiment, the therapeutic inhibitor peptide is a peptide having the amino acid sequence YARAAARQARAKALARQLGVAA [SEQ ID NO: 11]. According to another embodiment, the therapeutic inhibitor peptide is a peptide having the amino acid sequence YARAAARQARAKALNRQLGVAA [SEQ ID NO: 16]. According to another embodiment, the therapeutic inhibitor peptide is a peptide having the amino acid sequence YARAAARGQRAKALARQLAVA [SEQ ID NO: 17]. According to another embodiment, the therapeutic inhibitor peptide is a peptide having the amino acid sequence YARAAARGQRAKALARQLGVA [SEQ ID NO: 18]. According to another embodiment, the therapeutic inhibitor peptide is a peptide having the amino acid sequence YARAAARGQRAKALNRQLAVA [SEQ ID NO: 19]. According to another embodiment, the therapeutic inhibitor peptide is a peptide having the amino acid sequence YARAAARGQRAKALNRQLGVA [SEQ ID NO: 20]. According to another embodiment, the therapeutic inhibitor peptide is a peptide having the amino acid sequence YARAAARGQRAKALNRQLGVAA [SEQ ID NO: 21].

According to another embodiment, the kinase inhibiting composition, wherein it is desirable to deliver the composition locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions (i.e., kinase inhibiting compositions) also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The kinase inhibiting composition, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a kinase inhibiting peptide, or a pharmaceutically acceptable ester, salt, hydrate, solvate or prodrug thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, hydrate, solvate, or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. A "solution" generally is considered as a homogeneous mixture of two or more substances. It is frequently, though not necessarily, a liquid. In a solution, the molecules of the solute (or dissolved substance) are uniformly distributed among those of the solvent. As used herein, "dispersed system" or "dispersion" refers to a two-phase system in which one phase is distributed as particles or droplets in the second, or continuous, phase. The term "suspension" as used herein refers to preparations of finely divided, undissolved substances dispersed in liquid vehicles. The particulate matter of a suspension may settle slowly from the liquid vehicle in which it is dispersed; therefore, suspensions should be shaken well before use to ensure uniform distribution of solid in the vehicle and thereby uniform and proper dosage. As used herein "emulsion" refers to a colloid system in which both the dispersed phase and the dispersion medium are immiscible liquids where the dispersed liquid is distributed in small globules throughout the body of the dispersion medium liquid. A stable basic emulsion contains at least the two liquids and an emulsifying agent. Common types of emulsions are oil-in-water, where oil is the dispersed liquid and an aqueous solution, such as water, is the dispersion medium, and water-in-oil, where, conversely, an aqueous solution is the dispersed phase. It also is possible to prepare emulsions that are nonaqueous.

Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents, Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(l-glutamic acid), poly-(1-glutamic acid), poly-(d-aspartic acid), poly-(l-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive therapeutic inhibitor peptide using a protocol as essentially described by U.S. Pat. No. 5,977,163, which is incorporated herein by reference.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

In some embodiments, the kinase inhibiting composition is a pharmaceutical composition. The pharmaceutical compositions described within the present invention contain a therapeutically effective amount of a kinase inhibiting composition and optionally other therapeutic agents included in a pharmaceutically-acceptable carrier. The active ingredient may be a kinase inhibiting composition, a therapeutic inhibitor peptide, a PTD, or a therapeutic domain, or combinations thereof. The components of the pharmaceutical compositions also are capable of being comingled in a manner such that there is no interaction which would substantially impair the desired pharmaceutical efficiency.

The therapeutic agent(s), including the kinase inhibiting composition, may be provided in particles. The particles may contain the therapeutic agent(s) in a core surrounded by a coating. The therapeutic agent(s) also may be dispersed throughout the particles. The therapeutic agent(s) also may be adsorbed on at least one surface of the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the kinase inhibiting composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Use of a long-term sustained release implant may be particularly suitable for treatment of chronic conditions. Long-term sustained release implants are well-known to those of ordinary skill in the art and include some of the release systems described herein.

In another embodiment, the kinase inhibiting composition further comprises a gel, slow-release solid or semisolid compound, wherein the gel, slow-release solid or semisolid compound comprises a therapeutically effective amount of a therapeutic inhibitor peptide and a coating. The coating can be of any desired material, preferably a polymer or mixture of different polymers. Optionally, the polymer may be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound may be implanted in close proximity to a desired location, whereby the release of the active agent produces a localized pharmacologic effect.

In another embodiment, the kinase inhibiting composition further comprises a semisolid delivery system that utilizes a semisolid, biodegradable, biocompatible delivery system or a biodegradable, biocompatible multiparticulate dispersed and suspended in a semisolid, biodegradable, biocompatible biodegradable delivery system for injection, deposition or implantation within or upon the body so as to facilitate local therapeutic effects. In some such embodiments, the therapeutic agent is a kinase inhibiting composition, a therapeutic inhibitor peptide, a PTD, a therapeutic domain, or pharmaceutically acceptable salts thereof.

In another embodiment, the semisolid delivery system comprises partially or in whole a biocompatible, biodegradable, viscous semisolid wherein the semisolid comprises a hydrogel. In one embodiment, glyceryl monooleate, hereinafter referred to as GMO, is the intended semisolid delivery system or hydrogel. However, many hydrogels, polymers, hydrocarbon compositions and fatty acid derivatives having similar physical/chemical properties with respect to viscosity/rigidity may function as a semisolid delivery system. For example, sulfated polysaccharides, such as, but not limited to, heparin, may be utilized.

In one embodiment, the gel system is produced by heating GMO above its melting point (40-50° C.) and by adding a warm aqueous-based buffer or electrolyte solution, such as, for example, phosphate buffer or normal saline, which thus produces a three-dimensional structure. The aqueous-based buffer may be comprised of other aqueous solutions or combinations containing semi-polar solvents.

GMO provides a predominantly lipid-based hydrogel, which has the ability to incorporate lipophilic materials. GMO further provides internal aqueous channels that incorporate and deliver hydrophilic compounds. It is recognized that at room temperature (approximately 25° C.), the gel system may exhibit differing phases which comprise a broad range of viscosity measures.

In one embodiment, two gel system phases are utilized due to their properties at room temperature and physiologic temperature (about 37° C.) and pH (about 7.4). Within the two gel system phases, the first phase is a lamellar phase of approximately 5% to approximately 15% $H_2O$ content and approximately 95% to approximately 85% GMO content. The lamellar phase is a moderately viscous fluid, that may be easily manipulated, poured and injected. The second phase is a cubic phase consisting of approximately 15% to approximately 40% $H_2O$ content and approximately 85%-60% GMO content. It has an equilibrium water content at approximately 35% by weight to approximately 40% by weight. The term "equilibrium water content" as used herein refers to maximum water content in the presence of excess water. Thus the cubic phase incorporates water at approximately 35% by weight to approximately 40% by weight. The cubic phase is highly viscous. Viscosity may be measured, for example, via a Brookfield viscometer. The viscosity exceeds 1.2 million centipoise (cp); wherein 1.2 million cp being the maximum measure of viscosity obtainable via the cup and bob configuration of the Brookfield viscometer. In some such embodiments, a therapeutic agent may be incorporated into the semisolid so as to provide a system for sustained, continuous delivery thereof. In some such embodiments, the therapeutic agent is a therapeutic inhibitor peptide. In some such embodiments, the therapeutic agent is a PTD. In some such embodiments, the therapeutic agent is a therapeutic domain. In some such embodiments, other therapeutic agents, biologically-active agents, drugs, medicaments and inactives may be incorporated into the semisolid for providing a local biological, physiological, or therapeutic effect in the body at various release rates.

In some embodiments, alternative semisolids, modified formulations and methods of production are utilized such that the lipophilic nature of the semisolid is altered, or in the alternative, the aqueous channels contained within the semisolid are altered. Thus, various therapeutic agents in varying concentrations may diffuse from the semisolid at differing rates, or be released therefrom over time via the aqueous channels of the semisolid. Hydrophilic substances may be utilized to alter semisolid consistency or therapeutic agent release by alteration of viscosity, fluidity, surface tension or the polarity of the aqueous component. For example, glyceryl monostearate (GMS), which is structurally identical to GMO with the exception of a double bond at Carbon 9 and Carbon 10 of the fatty acid moiety rather than a single bond, does not gel upon heating and the addition of an aqueous component, as does GMO. However, because GMS is a surfactant, GMS is miscible in $H_2O$ up to approximately 20% weight/weight. The term "surfactant" as used herein refers to a surface active agent, thus being miscible in $H_2O$ in limited concentrations as well as polar substances. Upon heating and stirring, the 80% $H_2O$/20% GMS combination produces a spreadable paste having a consistency resembling hand lotion. The paste then is combined with melted GMO so as to form the cubic phase gel possessing a high viscosity as stated heretofore. In some such embodiments, the therapeutic agent is a therapeutic inhibitor peptide. In some such embodiments, the therapeutic agent is a PTD. In some such embodiments, the therapeutic agent is a therapeutic domain.

In another embodiment, hydrolyzed gelatin, such as commercially available Gelfoam™, is utilized for altering the aqueous component. Approximately 6.25% to 12.50% concentration of Gelfoam™ by weight may be placed in approximately 93.75% to 87.50% concentration of $H_2O$ respectively by weight or other aqueous based buffer. Upon heating and stirring, the $H_2O$ (or other aqeuous buffer)/Gelfoam™ combination produces a thick gelatinous substance. The resulting substance is combined with GMO, whereby a product so formed swells and forms a highly viscous, translucent gel being less malleable in comparison to neat GMO gel alone.

In another embodiment, polyethylene glycols (PEG's) may be utilized for altering the aqueous component to aid in drug solubilization. Approximately 0.5% to 40% concentration of PEG's (depending on PEG molecular weight) by weight placed in approximately 99.5% to 60% concentration of $H_2O$ respectively by weight or other aqueous based buffer. Upon heating and stirring, the $H_2O$ (or other aqeuous buffer)/PEG combination produces a viscous liquid to a semisolid substance. The resulting substance is combined with GMO, whereby a product so formed swells and forms a highly viscous gel.

Without being limited by theory, it is postulated the therapeutic agent releases from the semisolid through diffusion, conceivably in a biphasic manner. A first phase involves, for example, a lipophilic drug contained within the lipophilic membrane diffuses therefrom into the aqueous channel. The second phase involves diffusion of the drug from the aqueous channel into the external environment. Being lipophilic, the drug may orient itself inside the GMO gel within its proposed lipid bi-layer structure. Thus, incorporating greater than approximately 7.5% of the drug, for example a kinase inhibiting composition, by weight into GMO causes a loss of the integrity of the three-dimensional structure whereby the gel system no longer maintains the semisolid cubic phase, and reverts to the viscous lamellar phase liquid. In some such embodiments, the therapeutic agent is a therapeutic inhibitor peptide. In some such embodiments, the therapeutic agent is a PTD. In some such embodiments, the therapeutic agent is a therapeutic domain. In another embodiment, about 1 to about 45% of therapeutic agent is incorporated by weight into a GMO gel at physiologic temperature without disruption of the normal three-dimensional structure. As a result, this system allows the ability of significantly increased flexibility with drug dosages. Because the delivery system is malleable, it may be delivered and manipulated in an implant site, as to adhere and conform to contours of walls, spaces, or other voids in the body as well as completely fill all voids existing. The delivery system ensures drug distribution and uniform drug delivery throughout the implant site. Ease of delivery and manipulation of the delivery system within a space is facilitated via a semisolid delivery apparatus. A semisolid delivery apparatus facilitates targeted and controlled delivery of the delivery system.

In one embodiment, the multiparticulate component is comprised of biocompatible, biodegradable, polymeric or non-polymeric systems utilized to produce solid structures including but not limited to nonpareils, pellets, crystals, agglomerates, microspheres, or nanoparticles.

In another embodiment, the multiparticulate component comprises of poly(lactic-co-glycolide) (PLGA's). PLGA's are biodegradable polymer materials used for controlled and extended therapeutic agent delivery within the body. Such delivery systems offer enhanced therapeutic efficacy and reduced overall toxicity as compared to frequent periodic, systemic dosing. Without being limited by theory, it is postulated that PLGA's systems consisting of differing molar ratios of the monomeric subunits will facilitate greater flexibility in engineering precise release profiles for accommodating targeted therapeutic agent delivery through alterations in the rate of polymer degradation. In one embodiment, the PLGA composition is sufficiently pure so as to be biocompatible and remains biocompatible upon biodegradation. In one embodiment, the PLGA polymer is designed and configured into microspheres having a therapeutic agent or drug entrapped therein, whereby the therapeutic agent is subsequently released therefrom. In some such embodiments, the therapeutic agent is a kinase inhibiting agent. In some such embodiments, the therapeutic agent is a therapeutic inhibitor peptide. In some such embodiments, the therapeutic agent is a PTD. In some such embodiments, the therapeutic agent is a therapeutic domain.

In another embodiment, the multiparticulate component is comprised of poly d,l(lactic-co-caprolactone). This provides a biodegradable polymer material used for controlled and extended therapeutic agent delivery within the body with a similar drug release mechanism to that of the PLGA polymers. In one embodiment, the multiparticulate microspheres also are produced using biodegradable and/or biocompatible non-polymeric materials such as GMS.

In another embodiment, the multiparticulate component is further modified by methods used to encapsulate or coat the multiparticulate components using polymers of the same composition with the same or different drug substances, different polymers with the same or different drug substances, or with multiple layering processes containing no drug, the same drug, a different drug, or multiple drug substances. This allows the production of a multi-layered (encapsulated) multiparticulate system with a wide range of drug release profiles for single or multiple drug agents simultaneously. In another embodiment, coating materials which control the rate of physical drug diffusion from the multiparticulate may be utilized alone or in concert with the aforementioned embodiments and envisioned embodiments.

In another embodiment, the kinase inhibiting composition further comprises a delivery system that utilizes PLGA. The PLGA polymer contains ester bonds, which are labile to hydrolysis. When $H_2O$ penetrates the PLGA polymer, the ester bonds thereof are hydrolyzed, and monomers, being water soluble, are removed from the PLGA polymer, thus facilitating the physical release of the entrapped drug, for example, but not limited to, a kinase inhibiting composition, over time. In some such embodiments, other classes of synthetic biodegradable, biocompatible polymers may be used for controlled and extended therapeutic agent delivery within the body, including polyanhydrides, poly(phosphates), polydioxanone, cellulosics and acrylics which are extended as non-limiting examples. In some such embodiments, nonpolymeric materials may be utilized for controlled and extended therapeutic agent delivery within the body, including but not limited to sterols, sucrose fatty acid esters, fatty acids, and cholesteryl esters, which are extended as non-limiting examples.

In another aspect, the kinase inhibiting composition further comprises a semisolid delivery system, which acts as a vehicle for local delivery of therapeutic agents, comprising a lipophilic, hydrophilic or amphiphilic, solid or semisolid substance, heated above its melting point and thereafter followed by inclusion of a warm aqueous component so as to produce a gelatinous composition of variable viscosity based on water content. The therapeutic agent(s) is incorporated and dispersed into the melted lipophilic component or the aqueous buffer component prior to mixing and formation of the semisolid system. The gelatinous composition is placed within the semisolid delivery apparatus for subsequent placement, or deposition. Being malleable, the gel system is easily delivered and manipulated via the semisolid delivery apparatus in an implant site, where it adheres and conforms to contours of the implantation site, spaces, or other voids in the body as well as completely filling all voids existing. Alternatively, a multiparticulate component, comprised of a biocompatible polymeric or non-polymeric system, is utilized for producing microspheres having a therapeutic agent entrapped therein. Following final processing methods, the microspheres are incorporated into the semisolid system and subsequently placed within the semisolid delivery apparatus so as to be easily delivered therefrom into an implant site or comparable space, whereby the therapeutic agent is subsequently released therefrom by (a) drug release mechanism(s).

In another aspect, the present invention further provides a biomedical device comprising at least one isolated therapeutic inhibitor peptide, wherein the one or more isolated therapeutic inhibitor peptides is/are disposed on or in the device. In some such embodiments, the at least one therapeutic inhibitor peptide is at least one peptide having an amino acid sequence selected from the group consisting of peptides having an amino acid sequence of WLRRIKAWLRRIKALNRQLGVAA [SEQ ID NO: 14], FAKLAARLYRKALARQLGVAA [SEQ ID NO: 12], KAFAKLAARLYRKALARQLGVAA [SEQ ID NO: 15], YARAAARQARAKALARQLGVAA [SEQ ID NO: 11], YARAAARQARAKALNRQLGVAA [SEQ ID NO: 16], YARAAARGQRAKALARQLAVA [SEQ ID NO: 17], YARAAARGQRAKALARQLGVA [SEQ ID NO: 18], YARAAARGQRAKALNRQLAVA [SEQ ID NO: 19], YARAAARGQRAKALNRQLGVA [SEQ ID NO: 20] and YARAAARGQRAKALNRQLGVAA [SEQ ID NO: 21].

According to another aspect, the described invention provides an isolated nucleic acid that specifically hybridizes to mRNA encoding a peptide comprising a PTD amino acid sequence. The term "specifically hybridizes" as used herein refers to the process whereby a nucleic acid distinctively or definitively forms base pairs with complementary regions of at least one strand of DNA that was not originally paired to the nucleic acid. For example, a nucleic acid that may bind or hybridize to at least a portion of an mRNA of a cell encoding a peptide comprising a CPP sequence may be considered a nucleic acid that specifically hybridizes. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 90% sequence identity, or at least 100% sequence identity (i.e., complementary) with each other. According to another embodiment, the present invention provides an isolated nucleic acid that specifically hybridizes to mRNA encoding a peptide comprising a therapeutic inhibitor peptide amino acid sequence.

Methods of extraction of RNA are well-known in the art and are described, for example, in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," incorporated herein by this reference. Other isolation and extraction methods are also well-known, for example in F. Ausubel et al., "Current Protocols in Molecular Biology", John Wiley & Sons, 2007). Typically, isolation is performed in the presence of chaotropic agents, such as guanidinium chloride or guanidinium thiocyanate, although other detergents and extraction agents alternatively may be used. Typically, the mRNA is isolated from the total extracted RNA by chromatography over oligo(dT)-cellulose or other chromatographic media that have the capacity to bind the polyadenylated 3'-portion of mRNA molecules. Alternatively, but less preferably, total RNA can be used. However, it is generally preferred to isolate poly(A)+ RNA from mammalian sources.

Methods: Methods of Inhibiting Kinases that Activate Cytokines

According to another aspect, the present invention provides a method for treating an inflammatory disorder whose pathophysiology comprises inflammatory cytokine expression, the method comprising the steps: (a) providing a kinase inhibiting composition, wherein the therapeutically effective amount of the therapeutic inhibitor peptide inhibits at least one kinase enzyme, wherein the kinase inhibiting composition comprises a therapeutically effective amount of a therapeutic inhibitor peptide, wherein the therapeutic inhibitor peptide comprises a first domain and a second domain, wherein the first domain comprises a protein transduction domain (PTD) located proximal to the second domain, wherein the second domain comprises a therapeutic domain located proximal to the first domain; (b) administering the kinase inhibiting composition to a subject in need thereof, thereby inhibiting at least one kinase enzyme; and (c) reducing expression of at least one inflammatory cytokine, thereby treating the inflammatory disorder.

According to one embodiment, the inflammatory disorder whose pathophysiology comprises inflammatory cytokine expression is at least one disorder selected from the group consisting of asthma, ankylosing spondylitis, Type I diabetes, Guilliamé-Barre syndrome, lupus, psoriasis, scleroderma, Sjogren's disease, chronic prostatitis, glomerulonephritis, inflammatory bowel disease, pelvic inflammatory disease, reperfusion injury, rheumatoid arthritis, vasculitis, hypersensitivity vasculitis, endotoxic shock, pancreatitis, localized inflammatory disease, atherosclerosis, Alzheimer's disease, ischemia, intimal hyperplasia, stenosis, restenosis, leiomyoma, smooth muscle spasm, angina, Prinzmetal's angina, bradycardia, hypertension, cardiac hypertrophy, renal failure, stroke, pulmonary hypertension, toxemia of pregnancy, Raynaud's disease, hemolytic uremia, anal fissure, achalasia, impotence, migraine, vasculopathy, congestive heart failure, stunned myocardium, diastolic dysfunction, gliosis, chronic obstructive pulmonary disease, osteopenia, degenerative arthritis, sepsis, cirrhosis, interstitial fibrosis, colitis, appendicitis, gastritis, laryngitis, meningitis, otitis, traumatic brain injury, spinal cord injury, peripheral neuropathy, multiple sclerosis, cardiometabolic syndrome, non-alcoholic steatohepatitis, cystic fibrosis of the pancreas and lungs, injection fibrosis, endomyocardial fibrosis, idiopathic pulmonary fibrosis of the lung, mediastinal fibrosis, myelofibrosis, retroperitoneal fibrosis, nephrogenic systemic fibrosis, breast cancer, prostate cancer, and endothelial cell dysfunction.

According to another embodiment, the first domain is located 5' to the second domain. According to another embodiment, the second domain is located 3' to the first domain. According to another embodiment, the first domain is operably linked to the second domain. According to another embodiment, the second domain is operably linked to the first domain.

According to another embodiment, the kinase enzyme is mitogen-activated protein kinase-activated protein kinase. According to some such embodiments, the kinase enzyme is MK2. According to some such embodiments, the kinase enzyme is MK3. According to another embodiment, the kinase enzyme is CaMK.

According to another embodiment, the therapeutic domain of the therapeutic inhibitor peptide is a domain having substantial identity to amino acid sequence KALNRQLGVAA [SEQ ID NO: 13].

According to another embodiment, the therapeutic domain of the therapeutic inhibitor peptide is a domain having substantial identity to the amino acid sequence KALARQLGVAA [SEQ ID NO: 23].

According to another embodiment, the amino acid sequence of the therapeutic domain of the therapeutic inhibitor peptide is KAANRQLGVAA [SEQ ID NO: 22]. According to another embodiment, the therapeutic domain of the therapeutic inhibitor peptide is a domain having the amino acid sequence KALARQLGVAA [SEQ ID NO: 23]. According to another embodiment, the therapeutic domain of the therapeutic inhibitor peptide is a domain having the amino acid sequence KALNAQLGVAA [SEQ ID NO: 24]. According to another embodiment, the therapeutic domain of the therapeutic inhibitor peptide is a domain having the amino acid sequence KALNRALGVAA [SEQ ID NO: 25]. According to another embodiment, the therapeutic domain of the therapeutic inhibitor peptide is a domain having the amino acid sequence KALNRQAGVAA [SEQ ID NO: 26]. According to another embodiment, the therapeutic domain of the therapeutic inhibitor peptide is a domain having the amino acid sequence KALNRQLAVAA [SEQ ID NO: 27]. According to another embodiment, the therapeutic domain of the therapeutic inhibitor peptide is a domain having the amino acid sequence KALNRQLGAAA [SEQ ID NO: 28]. According to another embodiment, the therapeutic domain of the therapeutic inhibitor peptide is a domain having the amino acid sequence KALNRQLGVA [SEQ ID NO: 29]. According to another embodiment, the therapeutic domain of the therapeutic inhibitor peptide is a domain having the amino acid sequence KKKALNRQLGVAA [SEQ ID NO: 30]. According to another embodiment, the therapeutic domain of the therapeutic inhibitor peptide is a domain having the amino acid sequence KAANRQLGVAA [SEQ ID NO: 22]. According to another embodiment, the therapeutic domain of the therapeutic inhibitor peptide is a domain having the amino acid sequence KALNAQLGVAA [SEQ ID NO: 24]. According to another embodiment, the therapeutic domain of the therapeutic inhibitor peptide is a domain having the amino acid sequence KALNRQAGVAA [SEQ ID NO: 26]. According to another embodiment, the therapeutic domain of the therapeutic inhibitor peptide is a domain having the amino acid sequence KALNRQLGAAA [SEQ ID NO: 28]. According to another embodiment, the therapeutic domain of the therapeutic inhibitor peptide is a domain having the amino acid sequence KALNRQLGVAA [SEQ ID NO: 13]. According to another embodiment, the therapeutic domain of the therapeutic inhibitor peptide is a domain having the amino acid sequence KALARQLGVAA [SEQ ID NO: 23]. According to another embodiment the therapeutic domain of the therapeutic inhibitor peptide is a domain having the amino acid sequence KALNRALGVAA [SEQ ID NO: 25]. According to another embodiment, the therapeutic domain of the therapeutic inhibitor peptide is a domain having the amino acid sequence KALNRQLAVAA [SEQ ID NO: 27].

According to another embodiment, the protein transduction domain of the therapeutic kinase inhibitor peptide is a domain having substantial identity to the amino acid sequence WLRRIKAWLRRIKA [SEQ ID NO: 31].

According to another embodiment, the protein transduction domain of the therapeutic kinase inhibitor peptide is a domain having substantial identity to the amino acid sequence WLRRIKAWLRRI [SEQ ID NO: 34].

According to another embodiment, the PTD of the therapeutic kinase inhibitor peptide is a domain having the amino acid sequence WLRRIKAWLRRIKA [SEQ ID NO: 31]. According to another embodiment, PTD of the therapeutic kinase inhibitor peptide is a domain having the amino acid sequence WLRRIKA [SEQ ID NO: 32]. According to another embodiment, the PTD of the therapeutic kinase inhibitor peptide is a domain having the amino acid sequence YARAAARQARA [SEQ ID NO: 5]. According to another embodiment, the PTD of the therapeutic kinase inhibitor peptide is a domain having the amino acid sequence YGRKKRRQRRR [SEQ ID NO: 33]. According to another embodiment, the PTD of the therapeutic kinase inhibitor peptide is a domain having the amino acid sequence WLRRIKAWLRRI [SEQ ID NO: 34]. According to another embodiment, the PTD of the therapeutic kinase inhibitor peptide is a domain having the amino acid sequence FAKLAARLYR [SEQ ID NO: 35]. According to another embodiment, the PTD of the therapeutic kinase inhibitor peptide is a domain having the amino acid sequence KAFAKLAARLYR [SEQ ID NO: 36]. According to another embodiment, the PTD of the therapeutic kinase inhibitor peptide is a domain having the amino acid sequence YARAAARQARA [SEQ ID NO: 5]. According to another embodiment, the PTD of the therapeutic kinase inhibitor peptide is a domain having the amino acid sequence FAKLAARLYRKA [SEQ ID NO: 43]. According to another embodiment, the PTD of the therapeutic kinase inhibitor peptide is a domain having the amino acid sequence KAFAKLAARLYRKA [SEQ ID NO: 44].

According to another embodiment, the therapeutic inhibitor peptide is a peptide having the amino acid sequence WLRRIKAWLRRIKALNRQLGVAA [SEQ ID NO: 14]. According to another embodiment, the therapeutic inhibitor peptide is a peptide having the amino acid sequence FAKLAARLYRKALARQLGVAA [SEQ ID NO: 12]. According to another embodiment, the therapeutic inhibitor peptide is a peptide having the amino acid sequence KAFAKLAARLYRKALARQLGVAA [SEQ ID NO: 15]. According to another embodiment, the therapeutic inhibitor peptide is a peptide having the amino acid sequence YARAAARQARAKALARQLGVAA [SEQ ID NO: 11]. According to another embodiment, the therapeutic inhibitor peptide is a peptide having the amino acid sequence YARAAARQARAKALNRQLGVAA [SEQ ID NO: 16]. According to another embodiment, the therapeutic inhibitor peptide is a peptide having the amino acid sequence YARAAARGQRAKALARQLAVA [SEQ ID NO: 17]. According to another embodiment, the therapeutic inhibitor peptide is a peptide having the amino acid sequence YARAAARGQRAKALARQLGVA [SEQ ID NO: 18]. According to another embodiment, the therapeutic inhibitor peptide is a peptide having the amino acid sequence YARAAARGQRAKALNRQLAVA [SEQ ID NO: 19]. According to another embodiment, the therapeutic inhibitor peptide is a peptide having the amino acid sequence YARAAARGQRAKALNRQLGVA [SEQ ID NO: 20]. According to another embodiment, the therapeutic inhibitor peptide is a peptide having the amino acid sequence of YARAAARGQRAKALNRQLGVAA [SEQ ID NO: 21].

According to another embodiment, the kinase inhibiting composition further comprises a pharmaceutically acceptable carrier.

According to another embodiment, the kinase inhibiting composition is administered parenterally. According to another embodiment, the kinase inhibiting composition is administered via a biomedical device comprising at least one isolated therapeutic inhibitor peptide, wherein the one or more isolated therapeutic inhibitor peptides are disposed on or in the device. In some such embodiments, the at least one therapeutic inhibitor peptide is at least one peptide having an amino acid sequence selected from the group consisting of WLRRIKAWLRRIKALNRQLGVAA [SEQ ID NO: 14], FAKLAARLYRKALARQLGVAA [SEQ ID NO: 12], KAFAKLAARLYRKALARQLGVAA [SEQ ID NO: 15], YARAAARQARAKALARQLGVAA [SEQ ID NO: 11], YARAAARQARAKALNRQLGVAA [SEQ ID NO: 16], YARAAARGQRAKALARQLAVA [SEQ ID NO: 17], YARAAARGQRAKALARQLGVA [SEQ ID NO: 18], YARAAARGQRAKALNRQLAVA [SEQ ID NO: 19], YARAAARGQRAKALNRQLGVA [SEQ ID NO: 20] and YARAAARGQRAKALNRQLGVAA [SEQ ID NO: 21].

General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range, Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include plural references unless the context clearly dictates otherwise. All technical and scientific terms used herein have the same meaning.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods
Peptide Synthesis and Purification

Peptides were synthesized on Rink-amide or Knorr-amide resin (Synbiosci Corp.) using standard FMOC chemistry on a Symphony® Peptide Synthesizer (Protein Technologies, Inc.). The coupling reagent for the amino acids (Synbiosci Corp.) was 2-1H-benzotriazole-1-yl)-1,1,3,3-tetramethyluronium hexafluorphosphate/N-methyl maleimide (HBTU/NMM). Following synthesis, the peptide was cleaved from the resin with a trifluoroacetic acid-based cocktail, precipitated in ether, and recovered by centrifugation. The recovered peptide was dried in vacuo, resuspended in MilliQ purified water, and purified using an fast protein liquid chromatography (FPLC)(ÄKTA Explorer, GE Healthcare) equipped with a 22/250 C18 prep-scale column (Grace Davidson). An acetonitrile gradient with a constant concentration of either 0.1% trifluoroacetic acid or 0.1% acetic acid was used to achieve purification. Desired molecular weight was confirmed by time-of-flight matrix-assisted laser desorption ionization (MALDI) mass spectrometry using a 4800 Plus MALDI TOF/TOFTM Analyzer (Applied Biosystems).

Example 1

Determination of Essential Amino Acids of Therapeutic Inhibitor Peptides of MK2

Essential amino acids of therapeutic inhibitor peptides of MK2 were identified utilizing Ala and D-amino acid substitutions, 100 µM of KALNRQLGVAA [SEQ ID NO: 13] inhibited 73% of MK2 activity. First, each amino acid in the therapeutic domain (KALNRQLGVAA) [SEQ ID NO: 13] independently was replaced with Ala. Then, each amino acid in the peptide's therapeutic domain independently was replaced with its D-amino acid.

Fluorescence-based Kinase Activity Assay

The Omnia® Kinase Assay for MAPKAP-K2 kit (Invitrogen, Carlsbad, Calif.), was used to determine the reaction velocity for MK2 in the presence and absence of each of the peptides listed in Table 1. The kit contains a proprietary reaction buffer to which the following were added (final concentrations are given): 1 mM ATP, 0.2 mM DTT, 10 µM MAPKAP-K2 Sox-modified peptide substrate, 5 ng MK2, and the inhibitor peptide of interest (final volume of 50 µL). Human MK2 was purchased from Invitrogen. The reactions were performed at 30° C. in the wells of a low-protein-binding 96-well plate provided with the kit, and fluorescence readings (excitation=360 nm, emission=485 nm) were taken every 30 seconds for 20 minutes using a SpectraMax M5 Spectrophotometer (Molecular Devices). Reaction velocity was determined for each reaction well from the slope of a plot of relative fluorescence units versus time. Each inhibitor peptide was tested at least at four concentrations, 12.5, 25, 50 and 100 mmol, in triplicate.

In Table 1, "a" represents that the results shown are for 100 µM for all peptides; "b" represents the percentage change in MK2 reaction velocity versus the unsubstituted peptide (KALNRQLGVAA) [SEQ ID NO: 13] at a concentration of 100 µM; "c" represents the error reported as the standard deviation between three samples.

TABLE 1

Peptides tested in fluorescence-based kinase activity assay

| Inhibitor Peptide Tested[a] | % of KALNRQLGVAA[b] [SEQ ID NO: 13] Reaction Velocity (+VoSD)[c] | SEQ ID NO: |
|---|---|---|
| Alanine Substitutions | | |
| KAANRQLGVAA | +52 (6) | 22 |
| KALARQLGVAA | −61 (2) | 23 |

TABLE 1-continued

Peptides tested in fluorescence-based kinase activity assay

| Inhibitor Peptide Tested[a] | % of KALNRQLGVAA[b] [SEQ ID NO: 13] Reaction Velocity (+VoSD)[c] | SEQ ID NO: |
|---|---|---|
| KALNAQLGVAA | +258(14) | 24 |
| KALNRQLGVAA | +258(26) | 13 |
| KALNRQAGVAA | +18(7) | 26 |
| KALNRQLAVAA | −28(5) | 27 |
| KALNRQLGAAA | +273(22) | 28 |
| p-amino acid substitutions | | |
| KAdLNRQLGVAA | 46(7) | *** |
| KALdNRQLGVAA | −5(10) | *** |
| KALNdRQLGVAA | +206(7) | *** |
| KALNRdQLGVAA | +176(5) | *** |
| KALNRQdLGVAA | +257(17) | *** |
| KALNRQLGdVAA | +160(23) | *** |
| Other modifications | | |
| KALNRQLGVA | 0(5) | 29 |
| KKKALNRQLGVAA | −9(8) | 30 |
| WLRRIKAWLRRIKALNRQLGV | −132(10) | 47 |
| Cell penetrating peptide domain | | |
| WLRRIKA (non-functional) | 4306(21) | 32 |
| WLRRIKAWLRRIKA | −83(4) | 31 |
| YGRKKRRQRRR | +44(17) | 33 |
| YARAAARQARA | +149(13) | 5 |

Figure 3:
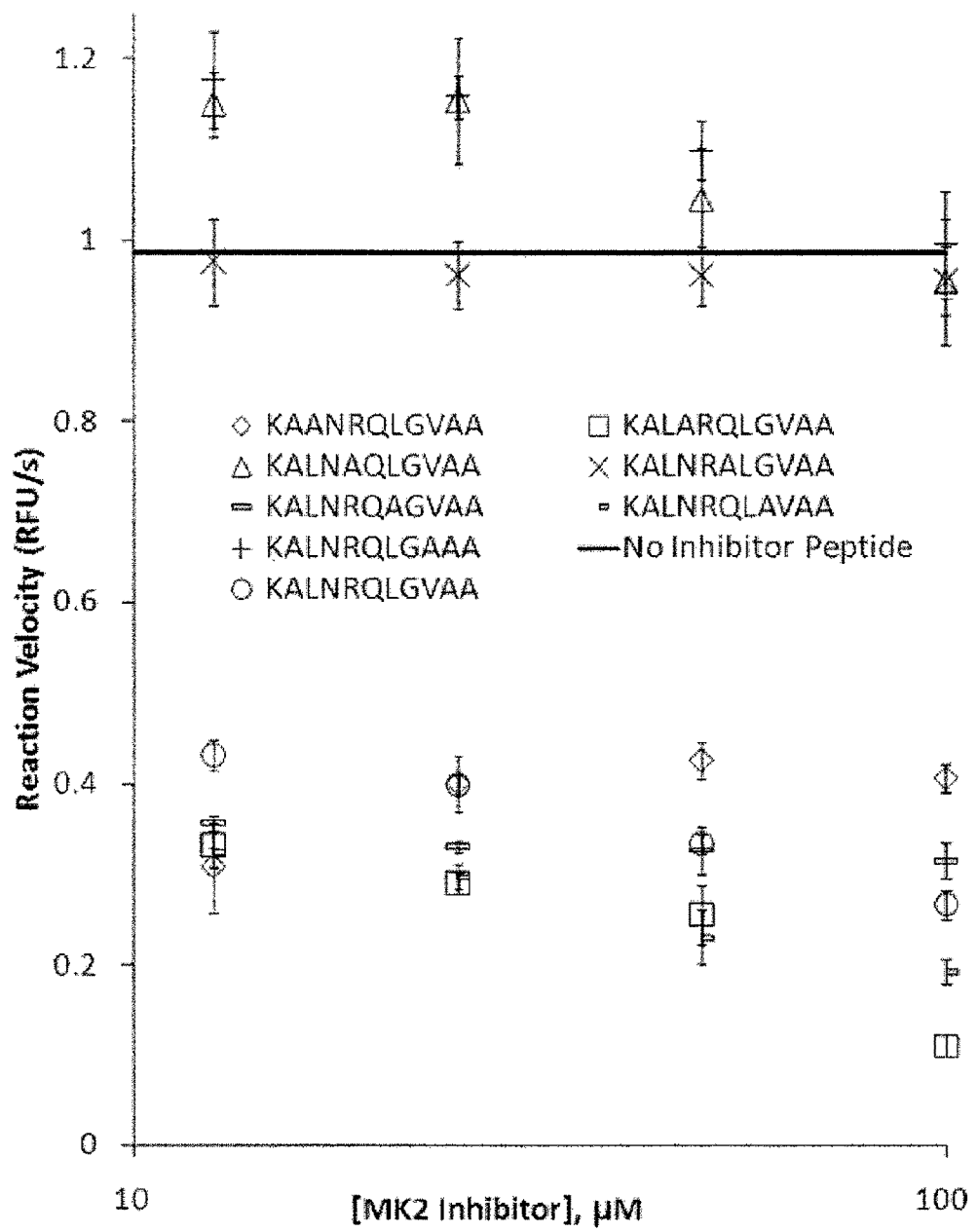
FIG. 3 shows a plot of reaction velocity (RFU/s) versus concentration of MK2 inhibitor peptide (μM).
Figure 4:
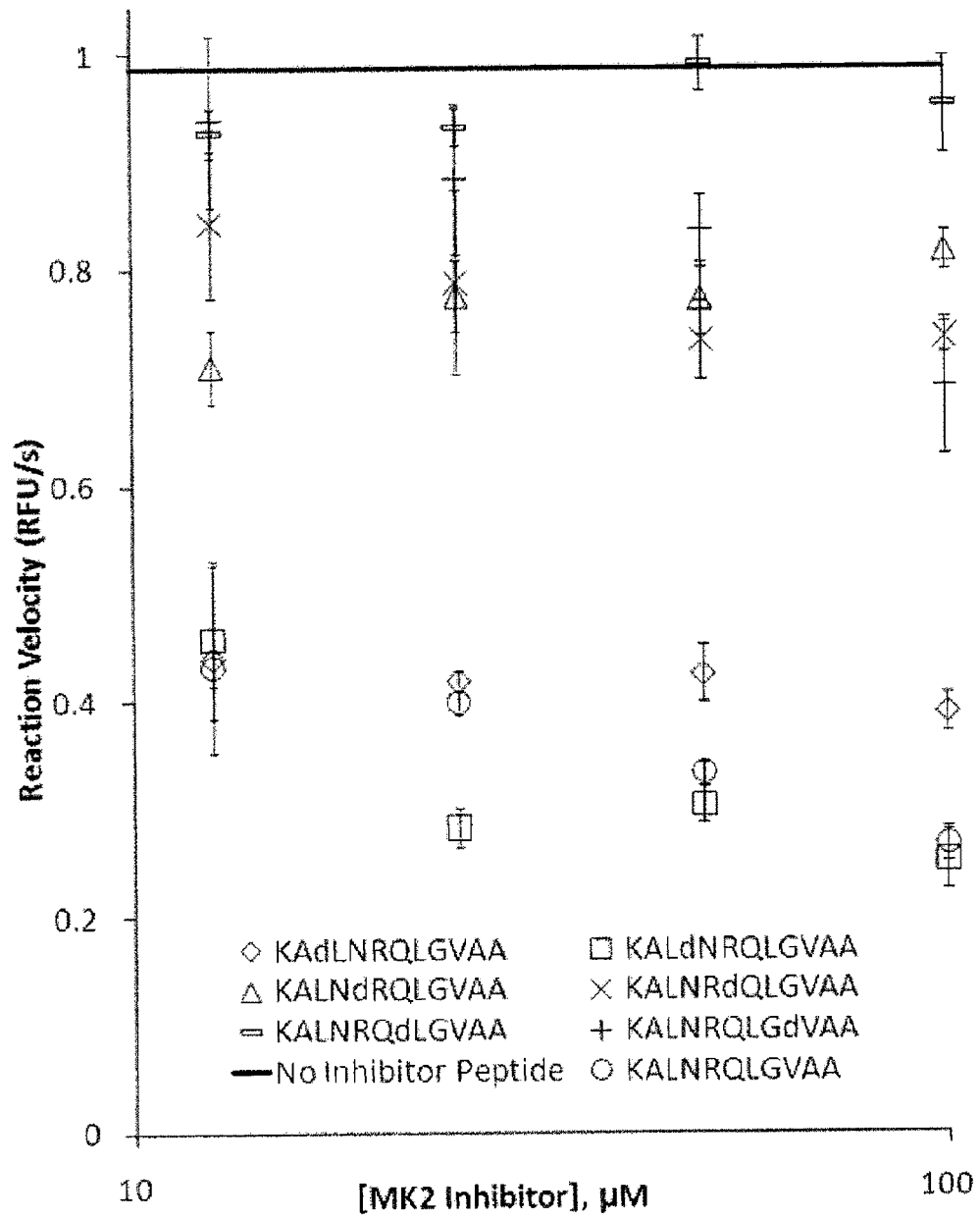
FIG. 4 shows a plot of reaction velocity (RFU/s) versus concentration of MK2 inhibitor peptide (μ).

D-amino acid and Ala scans showed that the Asn was not essential for MK2 inhibition (see Table 1, FIG. 3 and FIG. 4).

FIG. 3 shows a plot of reaction velocity (fluorescence unit/second) (RFU/s)) versus concentration MK2 inhibitor peptide (μM) where the inhibitor peptides incorporate the alanine substitutions. Replacing the Asp and Ala enhanced MK2 inhibition. The substitution of Ala for Gly slightly increased inhibition. The Ala scan also showed that Arg, Gln and Val were essential for MK2 inhibition. Although the two Leu were less essential amino acids, their removal diminished the efficacy of the therapeutic inhibitor peptide.

FIG. 4 shows a plot of reaction velocity (RFU/s) versus concentration MK2 inhibitor peptide (μM) where the inhibitor peptides incorporate the D amino acid substitutions. No D-amino acid substitution substantially enhanced MK2 inhibition; most D-amino acid substitutions substantially decreased the efficacy of the MK2 inhibitor peptide.

Figure 5:
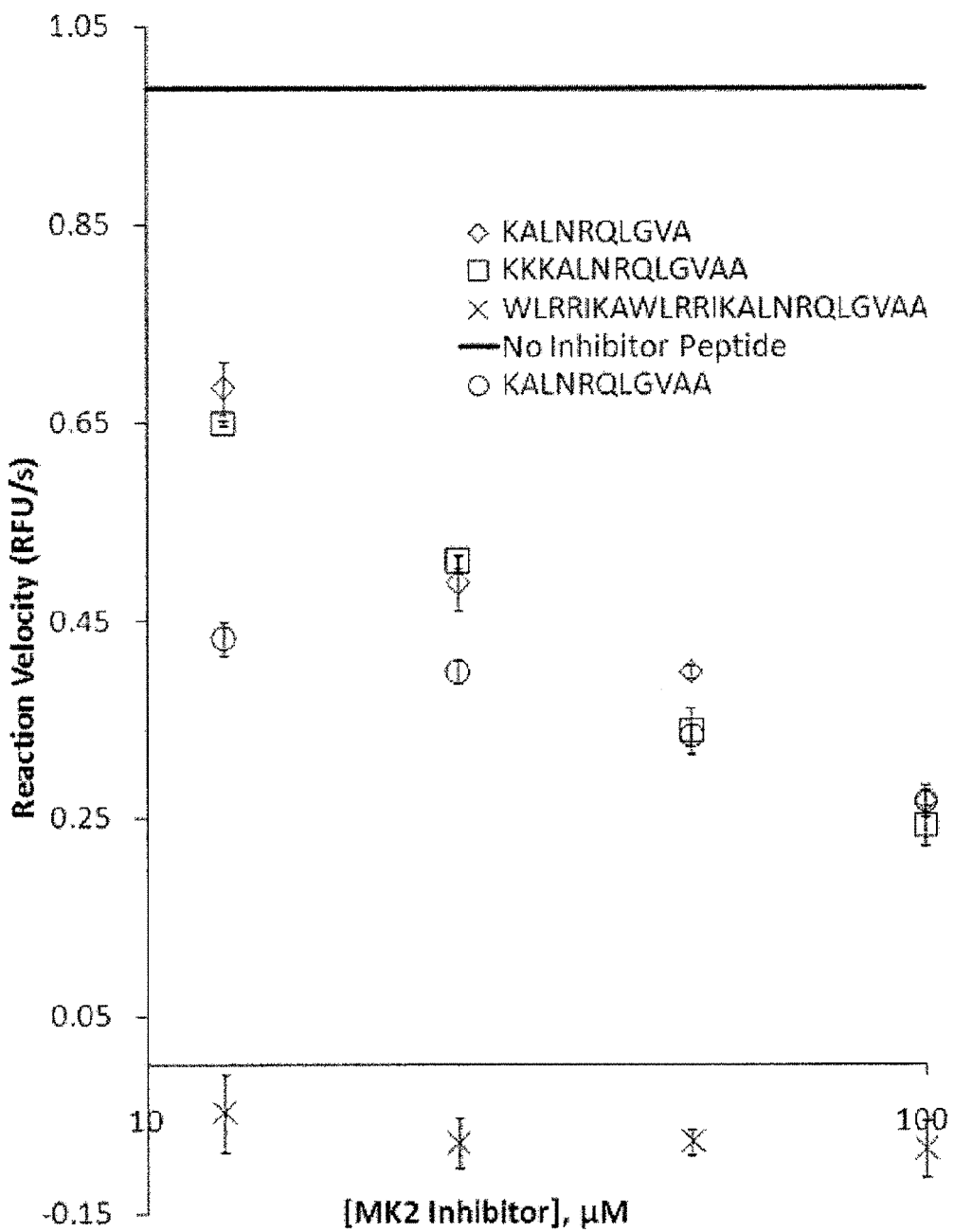
FIG. 5 shows a plot of reaction velocity (RFU/s) versus concentration of MK2 inhibitor peptide (μM).

FIG. 5 shows a plot of reaction velocity (RFU/s) versus concentration of MK2 inhibitor peptide (μM) where the inhibitor peptide has been modified. Table 1 and FIG. 5 show that MK2 inhibition was not enhanced by the C-terminal Ala (100 μM) and inhibition was slightly increased by two additional Lys in the inhibitor peptide. However, MK2 inhibition is decreased, at lower concentrations of inhibitor peptide, upon removal of the C-terminal Ala or addition of two N-terminal Lys.

Example 2

PTD Inhibition of MK2

MK2 inhibition by PTDs was demonstrated utilizing three PTDs: 1) WLRRIKAWLRRIKA [SEQ ID NO: 31]; 2) YGRKKRRQRRR [SEQ ID NO: 33]; and 3) YARAAARQARA [SEQ ID NO: 5].

Figure 6:
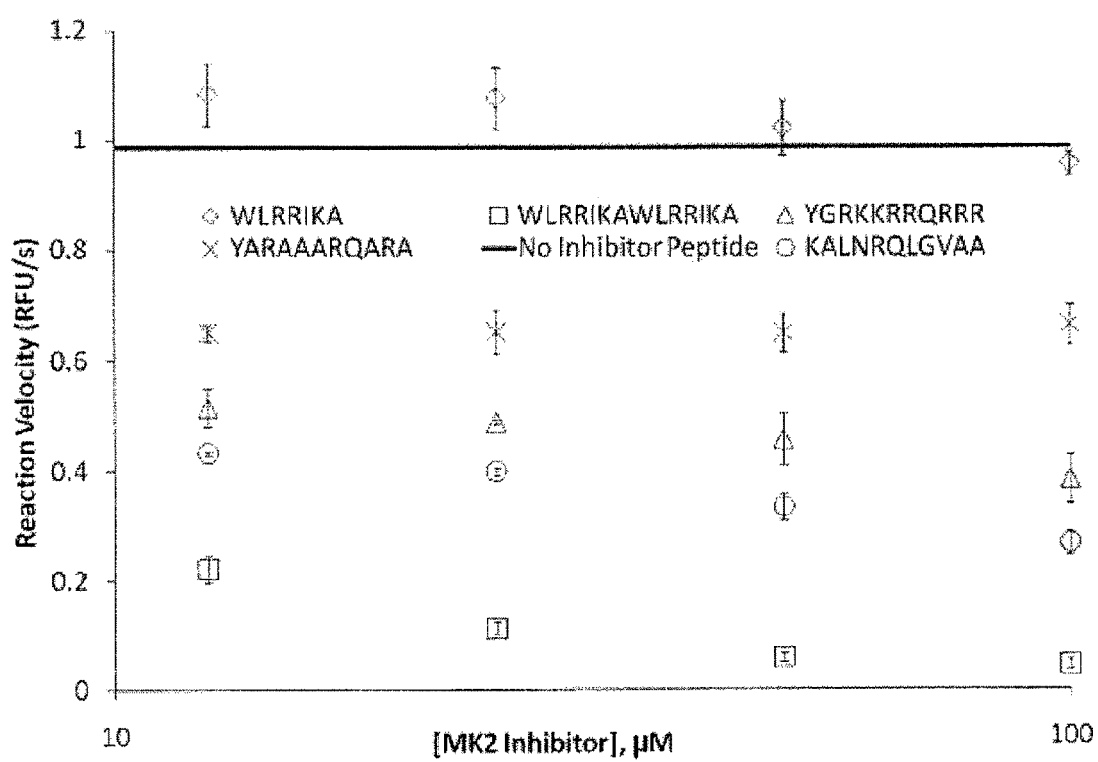
FIG. 6 shows a plot of reaction velocity versus (RFU/s) concentration of MK2 inhibitor peptide (μM).

FIG. 6 shows a plot of reaction velocity (RFU/s) versus concentration of MK2 inhibitor (μM) where the inhibitor peptide is a protein transduction domain. Table 1 and FIG. 4 show MK2 inhibition was least affected by PTD peptide YARAAARQARA [SEQ ID NO: 5] regardless of the PTD peptide concentration. MK2 activity was inhibited by PTD peptide YGRKKRRQRRR [SEQ ID NO: 33] across a broad range of PTD peptide concentration (from 61% inhibition at 100 PTD to 48% inhibition at 25 μM PTD). MK2 was potently inhibited by PTD peptide WLRRIKAWLRRIKA [SEQ ID NO: 31]; this PTD peptide provided higher inhibition of MK2 than the therapeutic domain peptides. Table 1 further shows the combination of the PTD peptide WLRRIKAWLRRIKA [SEQ ID NO: 31] and the therapeutic domain KALNRQLGVAA [SEQ ID NO: 13] provides a synergistic inhibitory effect.

Example 3

Modifications to the Therapeutic Domain Affect $IC_{50}$

The therapeutic domain of the therapeutic inhibitor peptides was modified to affect the $IC_{50}$ value. The modified therapeutic inhibitor peptides then were analyzed with radiometric assays.

Radiometric $IC_{50}$ and Kinase Activity Determination

A commercial radiometric assay service (Millipore, Billerica, Mass.) was used to test the specificity and potency of peptides containing a coupled transduction domain and therapeutic domain, hereinafter "complete peptides"). In these assays, if the kinase is not inhibited by an inhibitor peptide, a positively charged substrate is phosphorylated with a radio-labeled phosphate group from an ATP. The positively charged substrate is attracted to a negatively charged filter membrane, quantified with a scintillation counter, and compared to a 100% activity control, ATP concentrations within 15 μM of the apparent $K_m$ for ATP were chosen since an ATP concentration near the $K_m$ may allow for the kinases to have the same relative amount of phosphorylation activity.

Table 2 shows the buffer compositions for the kinases included in the screen; (h)=human, (m)=mouse, (r)=rat, and (y)=yeast.

| Buffer Compostion | Kinase(s) |
|---|---|
| 180 mM HEPES, 3.6 mM DTT, 0.07% Brij-35 | AMPK (r) |
| 20 mM HEPES, 0.03% Triton X-100 | PKCβI (h), PKCδ (h) |
| 20 mM MOPS, 1 mM EDTA, 0.01% Brij-35, 5% Glycerol, 0.1% β-mercaptoethanol, 1 mg/mL BSA | Abl (h), Aurora-A (h), BTK (h), CaMKI (h), CDK1/cyclinB (h), CHK1 (h), CHK2 (h), CK1δ (h), c-Kit (h), DYRK2 (h), EGFR (h), EphA2 (h), FGFR1 (h), GSK3β (h), IRAK4 (h), JAK3 (h), KDR (h), Lck (h), LIMK1 (h), Met (h), MLCK (h), PDGFRβ (h), PhKγ2 (h), Pim-1 (h), PKA (h), PKBβ (h), PKG1α(h), PKG1β (h), Ret (h), ROCK-I (h), Rsk2 (h), Src (1-530) (h), Tie2 (h), TrkA (h), MEK1 (h) |
| 25 mM TRIS, 0.1 mM EGTA, 0.1% β-mercaptoethanol, 1 mg/mL BSA | |
| 50 mM Na-β-glycerophosphate, 0.1 mM EGTA, 0.1% β-mercaptoethanol, 1 mg/mL BSA | PRAK (h) |
| 50 mM TRIS, 0.1 mM EGTa, 0.1 mM Na$_3$VO$_4$, 0.1% β-mercaptoethanol, 1 mg/mL BSA | IGF-1R (h), MAPK1 (h), SAPK2a (h), Syk (h) |

The protocols for each kinase assay are as follows:

(1) Abl (h)

In a final reaction volume of 25 μL, Abl (h) (5-10 mU) is incubated with 8 mM MOPS pH 7.0, 0.2 mM EDTA, 50 μM EAIYAAPFAKKK [SEQ ID NO: 48], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(2) AMPK (r)

In a final reaction volume of 25 AMPK (r) (5-10 mU) is incubated with 32 mM HEPES pH 7.4, 0.65 mM DTT, 0.012% Brij-35, 200 μM AMP, 200 μM AMARAASAAALARRR [SEQ ID NO: 49], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(3) Aurora-A (h)

In a final reaction volume of 25 μL, Aurora-A (h) (5-10 mU) is incubated with 8 mM MOPS pH 7.0, 0.2 mM EDTA, 200 μM LRRASLG [SEQ ID NO: 50] (Kemptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 50 mM phosphoric acid and once in methanol prior to drying and scintillation counting.

(4) BTK (h)

In a final reaction volume of 25μL, BTK (h) (5-10 mU) is incubated with 8 mM MOPS pH 7.0, 0.2 mM EDTA, 250 μM KVEKIGEGTYGVVYK [SEQ ID NO: 51] (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(5) CaMKI (h)

In a final reaction volume of 25 μL, CaMKI (h) (5-10 mU) is incubated with 8 mM MOPS pH 7.0, 0.2 mM EDTA, 0.5 mM CaCl.sub.2, 16 μg/mL calmodulin, 250 μM KKLNRTLSFAEPG [SEQ ID NO: 52], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(6) CDK1/cyclinB (h)

In a final reaction volume of 25 μL, CDK1/cyclinB (h) (5-10 mU) is incubated with 8 mM MOPS pH 7.0, 0.2 mM EDTA, 0.1 mg/mL histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(7) CHK1 (h)

In a final reaction volume of 25 μL, CHK1 (h) (5-10 mU) is incubated with 8 mM MOPS pH 7.0, 0.2 mM EDTA, 200 μM KKKVSRSGLYRSPSMPENLNRPR [SEQ ID NO: 53], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(8) CK1δ (h)

In a final reaction volume of 25 μL, CK1δ (h) (5-10 mU) is incubated with 8 mM MOPS pH 7.0, 0.2 mM EDTA, 200 μM KRRRALS(p)VASLPGL [SEQ ID NO: 54], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(9) CK2 (h)

In a final reaction volume of 25 μL, CK2 (h) (5-10 mU) is incubated with 20 mM HEPES pH 7.6, 0.15 M NaCl, 0.1 mM EDTA, 5 mM DTT, 0.1% Triton X-100, 165 μM RRRDDDS-DDD [SEQ ID NO: 55], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(10) c-Kit (h)

In a final reaction volume of 25 μL, c-Kit (h) (5-10 mU) is incubated with 8 mM MOPS pH 7.0, 0.2 mM EDTA, 10 mM MnCl$_2$, 0.1 mg/mL poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

(11) DYRK2 (h)

In a final reaction volume of 25 μL, DYRK2 (h) (5-10 mU) is incubated with 8 mM MOPS pH 7.0, 0.2 mM EDTA, 2 mg/mL casein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL, of a 3% phosphoric acid solution. 10 μL of the reaction is then spotted onto a P30 filtermat and washed three times for 5 minutes in 75 mM phosphoric acid and once in methanol prior to drying and scintillation counting.

(12) EGFR (h)

In a final reaction volume of 25 μL, EGFR (h) (5-10 mU) is incubated with 8 mM MOPS pH 7.0, 0.2 mM EDTA, 10 mM MnCl$_2$, 0.1 mg/mL poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

(13) EphA2 (h)

In a final reaction volume of 25 μL, EphA2 (h) (5-10 mU) is incubated with 8 mM MOPS pH 7.0, 0.2 mM EDTA, 0.1 mg/mL poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

(14) FGFR1 (h)

In a final reaction volume of 25 μL, FGFR1 (h) (5-10 mU) is incubated with 8 mM MOPS pH 7.0, 0.2 mM EDTA, 250 μM KKKSPGEYVNIEFG [SEQ ID NO: 56], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL, of a 3% phosphoric acid solution. 10 μL, of the reaction is then spotted onto a P30 filtermat and washed three times for 5 minutes in 75 mM phosphoric acid and once in methanol prior to drying and scintillation counting.

(15) Flt3 (h)

In a final reaction volume of 25 μL, Flt3 (h) (5-10 mU) is incubated with 8 mM MOPS pH 7.0, 0.2 mM EDTA, 50 μM EAIYAAPFAKKK [SEQ ID NO: 48], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(16) GSK3β (h)

In a final reaction volume of 25 μL, GSK3.beta. (h) (5-10 mU) is incubated with 8 mM MOPS pH 7.0, 0.2 mM EDTA, 20 μM YRRAAVPPSPSLSRHSSPHQS(p)EDEEE [SEQ ID NO: 57] (phospho GS2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 50 mM phosphoric acid and once in methanol prior to drying and scintillation counting.

(17) IGF-1R (h)

In a final reaction volume of 25 μL, IGF-1 R (h) (5-10 mU) is incubated with 50 mM Tris pH 7.5, 0.1 mM EGTA, 0.1 mM Na$_3$VO$_4$, 0.1% .beta.-mercaptoethanol, 250 μM KKKSPGEYVNIEFG [SEQ ID NO: 56], 10 mM MnCl$_2$, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(18) IRAK4 (h)

In a final reaction volume of 25 μL, IRAK4 (h) (5-10 mU) is incubated with 8 mM MOPS pH 7.0, 0.2 mM EDTA, 0.33 mg/mL myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 µl of the reaction is then spotted onto a P30 filtermat and washed three times for 5 minutes in 75 mM phosphoric acid and once in methanol prior to drying and scintillation counting.

(19) JAK3 (h)

In a final reaction volume of 25 µL, JAK3 (h) (5-10 mU) is incubated with 8 mM MOPS pH 7.0, 0.2 mM EDTA, 500 µM GGEEEEYFELVKKKK [SEQ ID NO: 58], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(20) KDR (h)

In a final reaction volume of 25 µL, KDR (h) (5-10 mU) is incubated with 8 mM MOPS pH 7.0, 0.2 mM EDTA, 0.33 mg/mL myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(21) Lck (h)

In a final reaction volume of 25 µL, Lck (h) (5-10 mU) is incubated with 50 mM Tris pH 7.5, 0.1 mM EGTA, 0.1 mM Na$_3$VO$_4$, 250 µM KVEKIGEGTYGVVYK [SEQ ID NO: 51] (Cdc2 peptide), 10 mM MgAcetate and [γ-$^{33}$ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(22) LIMK1 (h)

In a final reaction volume of 25 µL, LIMK1 (h) (5-10 mU) is incubated with 8 mM MOPS pH 7.0, 0.2 mM EDTA, 0.6 mg/mL cofilin, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(23) MAPK1 (h)

In a final reaction volume of 25 µL, MAPK1 (h) (5-10 mU) is incubated with 25 mM Tris pH 7.5, 0.02 mM EGTA, 250 µM peptide, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(24) MEK1 (h)

In a final reaction volume of 25 µL, MEK1 (h) (1-5 mU) is incubated with 50 mM Tris pH 7.5, 0.2 mM EGTA, 0.1% β-mercaptoethanol, 0.01% Brij-35, 1 µM inactive MAPK2 (m), 10 mM MgAcetate and cold ATP (concentration as required). The reaction is initiated by the addition of the MgATP. After incubation for 40 minutes at room temperature, 5 µL of this incubation mix is used to initiate a MAPK2 (m) assay.

(25) Met (h)

In a final reaction volume of 25 µL, Met (h) (5-10 mU) is incubated with 8 mM MOPS pH 7.0, 0.2 mM EDTA, 250 µM KKKSPGEYVNIEFG [SEQ ID NO: 56], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(26) MLCK (h)

In a final reaction volume of 25 µL, MLCK (h) (5-10 mU) is incubated with 8 mM MOPS pH 7.0, 0.2 mM EDTA, 0.5 mM CaCl$_2$, 16 µg/mL calmodulin, 250 µM KKLNRTLSFAEPG [SEQ ID NO: 52], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(27) PDGFRβ (h)

In a final reaction volume of 25 µL, PDGFRβ (h) (5-10 mU) is incubated with 8 mM MOPS pH 7.0, 0.2 mM EDTA, 0.1 mg/mL poly(Glu, Tyr) 4:1, 10 mM MnCl$_2$, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a Filtermat A and washed three times for 5 minutes in 75 mM phosphoric acid and once in methanol prior to drying and scintillation counting.

(28) PhKγ2 (h)

In a final reaction volume of 25 µL, PhK.gamma.2 (h) (5-10 mU) is incubated with 8 mM MOPS pH 7.0, 0.2 mM EDTA, 250 µM KKLNRTLSFAEPG [SEQ ID NO: 52], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(29) Pim-1 (h)

In a final reaction volume of 25 µL, Pim-1 (h) (5-10 mU) is incubated with 8 mM MOPS pH 7.0, 0.2 mM EDTA, 100 µM KKRNRTLTV [SEQ ID NO: 59], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

(30) PKA (h)

In a final reaction volume of 25 μL, PKA (h) (5-10 mU) is incubated with 8 mM MOPS pH 7.0, 0.2 mM EDTA, 30 μM LRRASLG [SEQ ID NO: 50] (Kemptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution, 10 μL of the reaction is then spotted onto a P30 filtermat and washed three times for 5 minutes in 50 mM phosphoric acid and once in methanol prior to drying and scintillation counting.

(31) PKBβ (h)

In a final reaction volume of 25 μL, PKA.beta. (h) (5-10 mU) is incubated with 8 mM MOPS pH 7.0, 0.2 mM EDTA, 30 μM GRPRTSSFAEGKK [SEQ ID NO: 60], 10 mM MgAcetate and ['y-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL it of a 3% phosphoric acid solution. 10 μL of the reaction is then spotted onto a P30 filtermat and washed three times for 5 minutes in 75 mM phosphoric acid and once in methanol prior to drying and scintillation counting.

(32) PKCβI (h)

In a final reaction volume of 25 μL, PKCβI (h) (5-10 mU) is incubated with 20 mM HEPES pH 7.4, 0.03% Triton X-100, 0.1 mM CaCl$_2$, 0.1 mg/mL phosphatidylserine, 10 μg/mL diacylglycerol, 0.1 mg/mL histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(33) PKCδ (h)

In a final reaction volume of 25 μL, PKC.delta. (h) (5-10 mU) is incubated with 20 mM HEPES pH 7.4, 0.03% Triton X-100, 0.1 mg/mL phosphatidylserine, 10 μg/mL diacylglycerol, 50 μM ERMRPRKRQGSVRRRV [SEQ ID NO: 61], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(34) PKG1α (h)

In a final reaction volume of 25 μL, PKG1.alpha. (h) (5-10 mU) is incubated with 8 mM MOPS pH 7.0, 0.2 mM EDTA, 10 μM cGMP, 200 μM RRRLSFAEPG [SEQ ID NO: 62], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(35) PKG1β (h)

In a final reaction volume of 25 μL, PKG1.beta. (h) (5-10 mU) is incubated with 8 mM MOPS pH 7.0, 0.2 mM EDTA, 10 μM cGMP, 200 μM RRRLSFAEPG [SEQ ID NO: 62], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(36) Ret (h)

In a final reaction volume of 25 μL, Ret (h) (5-10 mU) is incubated with 8 mM MOPS pH 7.0, 0.2 mM EDTA, 250 μM KKKSPGEYVNIEFG [SEQ ID NO: 56], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl, of a 3% phosphoric acid solution. 10 μL of the reaction is then spotted onto a P30 filtermat and washed three times for 5 minutes in 75 mM phosphoric acid and once in methanol prior to drying and scintillation counting.

(37) ROCK-I (h)

In a final reaction volume of 25 μL, ROCK-I (b) (5-10 mU) is incubated with 8 mM MOPS pH 7.0, 0.2 mM EDTA, 30 μM KEAKEKRQEQIAKRRRLSSLRASTSKSGGSQK [SEQ ID NO: 63], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(38) Rsk2 (h)

In a final reaction volume of 25 μL, Rsk2 (h) (5-10 mU) is incubated with 8 mM MOPS pH 7.0, 0.2 mM EDTA, 30 μM KKKNRTLSVA [SEQ ID NO: 64], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL it of a 3% phosphoric acid solution. 10 μL, of the reaction is then spotted onto a P30 filtermat and washed three times for 5 minutes in 75 mM phosphoric acid and once in methanol prior to drying and scintillation counting.

(39) SAPK2a (h)

In a final reaction volume of 25 μL, SAPK2a (h) (5-10 mU) is incubated with 25 mM Tris pH 7.5, 0.02 mM EGTA, 0.33 mg/mL myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(40) SRC (1-530) (h)

In a final reaction volume of 25 μL, SRC (1-530) (h) (5-10 mU) is incubated with 8 mM MOPS pH 7.0, 0.2 mM EDTA, 500 mM GGEEEEYFELVKKKK [SEQ ID NO: 58], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(41) Syk (h)

In a final reaction volume of 25 μL, Syk (h) (5-10 mU) is incubated with 50 mM Tris pH 7.5, 0.1 mM EGTA, 0.1 mM Na$_3$VO$_4$, 0.1% β-mercaptoethanol, 0.1 mg/mL poly(Glu, Tyr) 4:1, 10 mM MgAcetate and [γ-$^{33}$PATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

(42) Tie2 (h)

In a final reaction volume of 25 μL, Tie2 (h) (5-10 mU) is incubated with 8 mM MOPS pH 7.0, 0.2 mM EDTA, 0.5 mM MnCl$_2$, 0.1 mg/mL poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

(43) TrkA (h)

In a final reaction volume of 25 μL, TrkA (h) (5-10 mU) is incubated with 8 mM MOPS pH 7.0, 0.2 mM EDTA, 250 μM KKKSPGEYVNIEFG [SEQ ID NO: 56], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

(44) PRAK (h)

In a final reaction volume of 25 μL, PRAK (h) (5-10 mU) is incubated with 50 mM Na.beta.-glycerophosphate pH 7.5, 0.1 mM EGTA, 30 μM KKLRRTLSVA [SEQ ID NO: 65], 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 50 mM phosphoric acid and once in methanol prior to drying and scintillation counting.

IC$_{50}$ values for inhibitor peptides were determined using Millipore's IC$_{50}$Profiler Express service. The IC$_{50}$ value was estimated from a 10-point curve of one-half log dilutions. Forpeptides tested for specificity, the concentration of the peptides that inhibited approximately 95% of MK2 activity was chosen to profile against a battery of kinases related to MK2, cell viability, or human disease from MilliporeKinaseProfiler service. In both assays, compounds were supplied in dimethylsulfoxide (DMSO). Every kinase activity measurement was conducted in duplicate.

FIG. 1 shows IC$_{50}$ curves and values for therapeutic inhibitor peptide variants with the same PTD (YARAAARGQARA) [SEQ ID NO: 37] compared to the independent PTD peptide YARAAARGQARA [SEQ ID NO: 37] and the independent therapeutic domain peptide KKKALNRQLGVAA [SEQ ID NO: 30]. All of the therapeutic inhibitor peptide variants demonstrated IC$_{50}$ values lower than the therapeutic domain peptide KKKALNRQLGVAA [SEQ ID NO: 30]. The substitution of Asn to Ala and/or substitution of Gly to Ala produced minor changes in the IC$_{50}$ values for the therapeutic inhibitor peptide. Removal of the terminal Ala provided a minor increase in the IC$_{50}$ value.

Example 4

PTDs Affect Potency of Therapeutic Inhibitor Peptides

Figure 2:
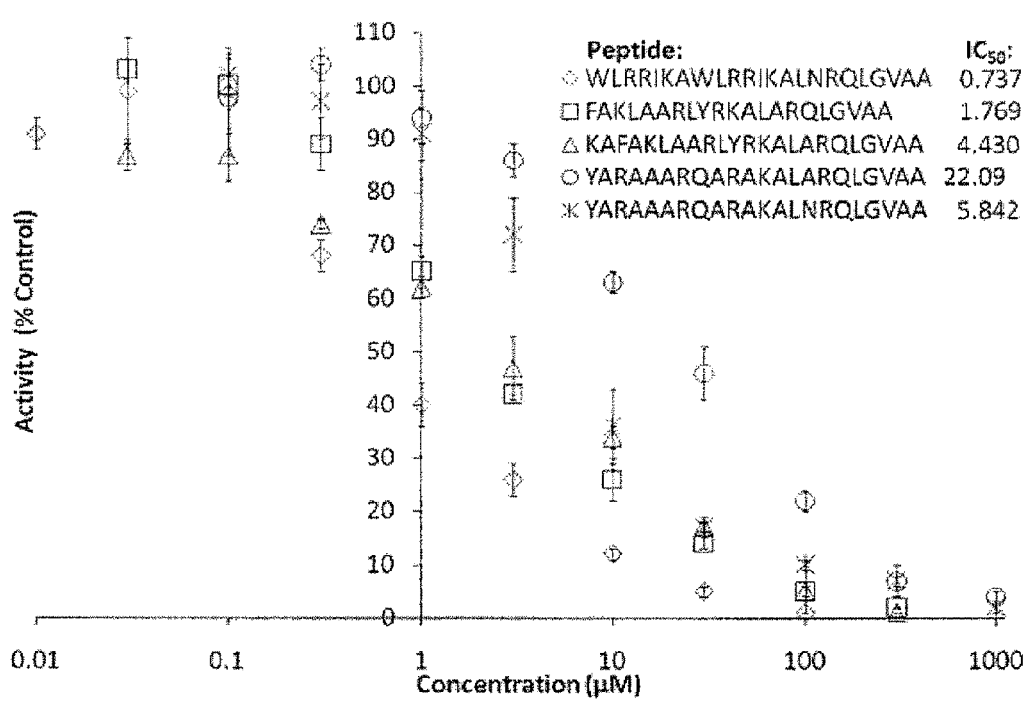
FIG. 2 shows a plot of activity (% relative to the control) versus inhibitor peptide concentration (μM).

PTDs demonstrated different affects on the potency of the therapeutic inhibitor peptides. Each of the PTDs, when combined with their respective therapeutic domain, provided different levels of synergism with the inhibitory effect of the therapeutic inhibitor peptides. FIG. 2 shows IC$_{50}$ curves and values for therapeutic inhibitor peptide variants with the same therapeutic domain (KALNRQLGVAA) [SEQ ID NO: 13] but with different PTDs. The therapeutic inhibitor peptide incorporating the PTD peptide WLRRRIKAWLRRI [SEQ ID NO: 38] had a lower IC$_{50}$ value (greater than 30-fold lower) than the therapeutic inhibitor peptide incorporating the PTD peptide YARAAARQARA [SEQ ID NO: 5].

Example 5

PTD and Amino Acid Substitutions Affect Specificity of the Therapeutic Inhibitor Peptides Therapeutic inhibitor peptides were assayed for activity against human kinases related to MK2, cell viability, or human disease. The assays were performed using concentrations of therapeutic inhibitor peptides that yielded 2% to 8% of normal MK2 activity. Error is reported as the standard deviation between 2 samples, and "c" is rat AMPK whereas all other kinases used are human kinases.

Table 3 and Table 4 show that the therapeutic inhibitor peptides with PTD peptides FAKLAARLYR [SEQ ID NO: 35] and KAFAKLAARLYR [SEQ ID NO: 36] had higher specificity for certain kinases than the therapeutic inhibitor peptide with the PTD peptide WLRRIKAWLRRI [SEQ ID NO: 34].

TABLE 3

Effect of CPP on Inhibitor Peptide Specificity for MK2

| Peptide | Concentration Tested [μM] | Percentage of the 43 kinases Tested with less than 20% Activity | SEQ ID NO: |
|---|---|---|---|
| WLRRIKAWLRRIKALNRQLGVAA | 30 | 47 | 14 |
| FAKLAARLYRKALARQLGVAA | 100 | 37 | 12 |
| KAFAKLAARLYRKALARQLGVAA | 100 | 28 | 15 |

TABLE 4

Effect Of Cell-Permeant Peptides on 43 Different Kinases.

| | Peptide Sequence | | |
|---|---|---|---|
| | [SEQ ID NO: 30] WLRRIKAWLRRI- | WLRRIKAWLRRI- | [SEQ ID NO: 66] KAFAKLAARL |
| | Concentration: | | |
| | 30 | 100 | 100 |
| Kinase | Kinase Activity (%) (+SD %) | | |
| AbI | 24 (5) | 41 (2) | 55 (0) |
| AMPKc | 36 (4) | 101 (6) | 118 (7) |
| Aurora-A | 46 (1) | 65 (5) | 60 (1) |
| BTK | 5 (0) | 19 (1) | 16 (3) |
| CaMK1 | 9 (1) | 0 (2) | 0 (2) |
| CDKI/cyclin B | 17 (0) | 36 (2) | 55 (3) |
| CHK 1 | 31 (5) | 54 (6) | 68 (0) |
| CKIδ | 52 (1) | 99 (3) | 97 (2) |
| CK2 | 114 (4) | 80 (14) | 79 (12) |
| cKit | 23 (2) | 42 (3) | 31 (6) |
| DYRK2 | 93 (8) | −11 (1) | −10 (0) |
| EGFR | 10 (4) | 18 (2) | 16 (1) |
| EphA2 | 38 (4) | 32 (2) | 22 (7) |
| FGFRI | 27 (1) | 22 (1) | 35 (1) |
| Flt3 | 38 (1) | 14 (0) | 20 (3) |
| GSK3β | 129 (2) | 188 (4) | 184 (1) |
| IGF-1R | 227 (12) | 69 (4) | 76 (12) |
| IRAK4 | 12 (1) | 13 (4) | 16 (2) |
| JAK3 | 85 (5) | 102 (2) | 91 (8) |
| KDR | 27 (0) | 78 (6) | 56 (4) |
| Lck | 130 (1) | 493 (7) | 847 (29) |
| LIMK1 | 89 (3) | 92 (2) | 93 (3) |
| MAPK1 | 121 (5) | 104 (3) | 108 (1) |
| MEK1 | 14 (2) | 68 (2) | 66 (0) |
| Met | 30 (1) | 17 (3) | 22 (3) |
| MLCK | 4 (1) | 1 (1) | 2 (0) |
| PDGFRβ | 42 (4) | 92 (4) | 66 (8) |
| PhKγ2 | 15 (0) | 20 (0) | 27 (3) |
| Pim-1 | 5 (1) | 1 (0) | 1 (2) |
| PKA | 80 (1) | 76 (8) | 103 (1) |
| PKBβ | 18 (2) | 16 (5) | 28 (4) |
| PKCβ1 | 8 (4) | 73 (0) | 23 (3) |
| PKCδ | 11 (0) | 40 (2) | 24 (3) |
| PKG1α | 1691) | 12 (2) | 25 (2) |
| PKG1β | 15 (4) | 15 (1) | 24 (5) |
| Ret | 11792) | 89 (0) | 107 (9) |
| ROCK-1 | 0 (1) | 25 (2) | 29 (0) |
| Rsk2 | 14 (5) | −1 (1) | 6 (1) |
| SAPK2a | 61 (7) | 30 (6) | 59 (8) |
| Src (residues 1-530) | 6 (1) | 5 (1) | 3 (0) |
| Syk | 19 (3) | 38 (9) | 4 (4) |
| Tie2 | 17 (1) | 0 (0) | 8 (4( |
| TrkA | 6 (1) | 17 (2) | 16 (2) |

Additional therapeutic inhibitor peptide variants were assayed for activity against several human kinases representative of several families of kinases. These kinases included: MK2; MK3; CaMKI (calcium/calmodulin-dependent protein kinase); PRAK (p38 regulated/activated protein kinase, also known as mitogen-activated protein kinase activated protein kinase 5 (MAPKAPK5)); SAPK2a (p38α); IRAK4 (IL-1 receptor (IL-1R)-associated kinase); MLCK (myosin light chain kinase); PKBβ (protein kinase B); PCKδ (protein kinase C); and ROCK-I (Rho-associated serine/threonine kinase). The concentration selected yielded between 0-10% MK2 activity based on $IC_{50}$ data; YARAAARQAR-AKALARQLGVAA [SEQ ID NO: 11] may be at a slightly higher concentration, and all kinase inhibition may be greater than expected for the concentration listed; error is reported as the standard deviation between 2 samples.

Table 5 shows differences in specificity among therapeutic inhibitor peptides. All of the therapeutic inhibitor peptides inhibited both MK2, MK3 and CaMKI. Therapeutic inhibitor peptide variants with Ala substituted for Asn demonstrated greater inhibition of CaMKI than MK2. The therapeutic inhibitor peptides demonstrated minimal affect on PRAK activity. Peptide FAKLAARLYRKALARQLGVAA [SEQ ID NO: 12] inhibited activity of SAPK2a. The therapeutic inhibitor peptide WLRRIKAWLRRIKALNRQLGVAA [SEQ ID NO: 14] demonstrated the least specificity.

TABLE 5

Effect of 5 Complete Inhibitor Peptide Variants on 10 Human Kinases.

| | Peptide sequence | | | | |
|---|---|---|---|---|---|
| | WLRRIKA WLRRIKAL NRQLGVAA | FAKLAARLY RLARQLGVAA | KAFAKLAA RLYRLARQ LGVAA | YARAAARQ ARALARQL GVAA | YARAAAR QARALNR QLGVAA |
| | SEQ ID NO: | | | | |
| | 14 | 39 | 40 | 41 | 42 |
| | Concentration of peptide inhibitor (µM) | | | | |
| | 30 | 100 | 100 | 300 | 300 |
| Human kinase | Kinase Activity | | | | |
| MK2 | 2(1) | 5(2) | 8(1) | −7(0) | 10(3) |
| MK3 | 16(2) | 10(1) | 17(1) | 5(1) | 19(3) |
| CaMK1 | 9(1) | 0(2) | 0(2) | 2(0) | 8(1) |
| PRAK | 67(9) | 131(4) | 148(4) | 86(2) | 81(3) |
| SAPK2a (p38α) | 61(7) | 30(6) | 59(8) | 66(3) | 100(6) |
| IRAK4 | 12(1) | 13(4) | 16(2) | 2392) | 68(3) |
| MLCK | 4(1) | 1(1) | 2(0) | 9(0) | 66(9) |
| PKBβ | 18(2) | 16(5) | 28(4) | 17(2) | 96(1) |
| PKCδ | 11(0) | 40(2) | 24(3) | 101(3) | 105(2) |
| ROCK-1 | 0(1) | 25(2) | 29(0) | 27(4) | 95(7) |

Therapeutic inhibitor peptide variants incorporating the PTD peptide YARAAARQARA [SEQ ID NO: 5], but differing in having Ala substituted for Asn in the therapeutic domain, provided greater inhibition of the kinases IRAK4, PKBβ, MLCK, ROCK-I and p38α than the variant with the Asn substitution.

Example 6

Therapeutic Inhibitor Peptide Activity Against Interleukin-6 and Tumor Necrosis Factor-α

The inhibition activity of therapeutic inhibitor peptides against the cytokines Interleukin-6 (IL-6) and tumor necrosis factor-α (TNF-α) was determined.

6.1. Peptide Synthesis

Peptides were synthesized on Rink-amide or Knorr-amide resin (Synbiosci Corp., Livermore, Calif.) using standard FMOC chemistry on a Symphony® Peptide Synthesizer (Protein Technologies, Inc., Tucson, Ariz.). The coupling reagent for the amino acids (Synbiosci Corp.) was HBTU/NMM (Anaspec, Freemont, Calif./Sigma, St. Louis, Mo.). Following synthesis, the peptide was cleaved from the resin with a trifluoroacetic acid-based cocktail (95% trifluoroacetic acid, 2.5% water, 1.25% triisopropylsilane, and 1.25% ethanediol), precipitated in ether, and recovered by centrifugation. The recovered peptide was dried in vacuo, resuspended in MilliQ purified water, and purified using an FPLC (ÄKTA Explorer, GE Healthcare, Piscataway, N.J.) equipped with a 22/250 C18 prep-scale column (Grace Davidson, Columbia, Md.). An acetic acid was used to achieve purification. Desired molecular weight was confirmed by time-of-flight MALDI mass spectrometry using a 4800 Plus MALDI TOF/TOF™ Analyzer (Applied Biosystems, Foster City, Calif.).

6.2. Mesothelial Cell Culture and Treatment

A cell line of pleural mesothelial cells (CRL-9444) was purchased from American Type Culture Collection. Cells were maintained and seeded in Medium 199 with Earle's BSS and 0.75 mM L-glutamine (Mediatech, Inc., Manassas, Va.), 1.25 g/L sodium bicarbonate (Sigma, St. Louis, Mo.), 3.3 nM epidermal growth factor (MBL International, Woburn, Mass.), 40 nM hydrocortisone (Sigma), 870 nM insulin (MBL International), 20 mM HEPES (Sigma), trace elements mixture B (Mediatech, Inc.), 10% fetal bovine serum (FBS) (Hyclone, Waltham, Mass.) and 1% penicillin/streptomycin (Mediatech, Inc.). Prior to treating cells with therapeutic inhibitor peptides, cells were allowed to acclimate in serum-free media consisting of only Medium 199 with Earle's BSS. L-glutamine, sodium bicarbonate, HEPES, trace elements mixture B, and penicillin/streptomycin (concentrations and suppliers as above) for 24 hours prior to treatment with cytokines and/or inhibitor peptides. Cytokines with or without inhibitor peptide or the commercially available protein kinase inhibitor Rotterlin (IC$_{50}$=5 µM) (Tocris Bioscience, Ellisville, Mo.)) also always were added simultaneously in this media formulation. For all cell culture experiments, the cell-penetrating MK2 inhibitor peptide sequence YARAAAR-QARAKALARQLGVAA [SEQ ID NO: 11] was used.

6.3. Interleukin-6 Analysis

It generally is believed that proinflammatory cytokines such as interleukin (IL)-1, IL-6 and tumor necrosis factor-α (TNF-α) are released into the abdominal cavity after abdominal surgery. These cytokines may play a role in adhesion formation/reformation. Studies have reported that IL-1 and TNF-α are both pro-inflammatory cytokines important in the early phase of wound healing and are produced by activated macrophages in the peritoneal fluid, while IL-6 is expressed by activated macrophages and its production is up-regulated by IL-1 during the inflammatory process. Furthermore, studies have reported that both IL-1 and TNF-α are potent inducers of IL-6. These cytokines are thought to be important as they interact extensively with the fibrinolytic pathway and may contribute directly or indirectly to the remodeling of the extracellular matrix. Studies have reported that both IL-1β and TNF-α upregulate the level of expression of IL-6 and IL-8 within mesothelial cells. Additionally, IL-1β has been shown to upregulate the level of expression of TNF-α, IL-6 and IL-8 within macrophages. Accordingly, the quantification of the level of expression of IL-6 induced by IL-1β or TNF-α in mesothelial cells or macrophages is used as a model assay system for determining the activity of therapeutic inhibitor peptides.

IL-6 analysis was performed with a IL-6 ELISA kit (PeproTech, Inc., Rocky Hill, N.J.). Briefly, the plate was prepared as follows. The capture antibody (antigen-affinity purified goat anti-hIL-6+2.5 mg D-mannitol) was diluted with phosphate buffered saline (PBS) to a concentration of 1 µg/ml and added to the each well of the plate. The plate was sealed and incubated at room temperature overnight. The wells then were aspirated to remove liquid, and washed 4 times using wash buffer (300 µl per well of 0.05% Tween-20 in PBS). After the last wash, the plate was inverted to remove residual buffer, and blotted on a paper towel. Block buffer (300 µl per well of 1% BSA in PBS) was added, the plate incubated for at least 1 hour at room temperature, aspirated and washed 4 times.

Standards (from 2 ng/ml to zero) and samples were prepared in diluent, immediately added to each well in triplicate, and incubated at room temperature for at least 2 hours on a plate shaker adjusted to 300 rpm. The wells then were aspirated, washed 4 times, detection antibody (biotinylated antigen-affinity purified goat anti-hIL-6+2.5 mg D-mannitol; 0.25 µg/ml) added (100 µl) to each well, and the plate incubated at room temperature for 2 hours on a plate shaker adjusted to 300 rpm. Following the incubation, the plate was aspirated, washed 4 times, avidin-horse radish peroxidase (HRP) conjugate added ((5.5 µl:10994.5 µl diluent) (100 µl) to each well, incubated for 30 minutes at room temperature on a plate shaker adjusted to 300 rpm, aspirated, and washed 4 times. To each well then was added ABTS Liquid Substrate Solution (Sigma) (100 µl). The plate was incubated at room temperature for color development on a plate shaker adjusted to 300 rpm. Absorbance was measured at 405 nm and 650 nm (650 nm was the wavelength correction subtracted from each 405 nm measurement) using a Spectramax M5 Microplate Reader (Molecular Devices) every 5 minutes for 50 minutes. Hoeschst 33342 nuclear stain (Invitrogen) was used to quantify cell number on the basis of DNA quantity. All results were run in triplicate and normalized to cell number.

Results are presented as means±standard deviation. One-way ANOVA analyses were used to determine statistically significant increases or decreases in parameters of interest. Significant differences were analyzed with Tukey HSD post hoc comparisons. A significance level of α=0.05 was used in cytokine analyses.

6.4. Regulation of IL-6 Expression with Induction by IL-1β

Mesothelial cells were incubated with IL-1β (1 ng/ml) (to induce IL-6 expression) and/or different concentrations of therapeutic inhibitor peptide. The commercially available protein kinase inhibitor Rottlerin was introduced as an inhibitor of both MK2 and PRAK.

Figure 7:
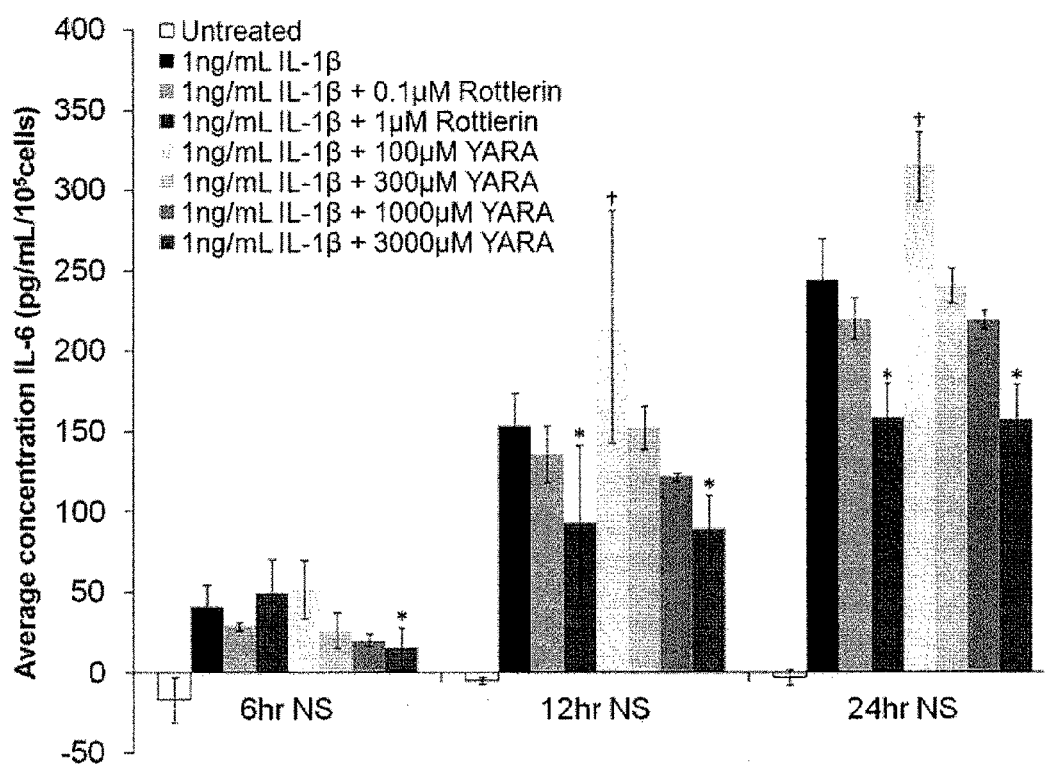
FIG. 7 shows a plot of the average concentration of IL-6 (pg/ml/$10^5$ cells) against time. YARA=YARAAARQARAKALARQLGVAA [SEQ ID NO: 11]. †=significantly higher than 1 ng/mL IL-1β treated samples. *=significantly lower than 1 ng/mL IL-1β treated samples. Error bars represent standard deviation between three samples.

FIG. 7 shows a plot of the average concentration of IL-6 (pg/ml/$10^5$ cells) against time. These results show that therapeutic inhibitor peptide YARAAARQARAKALARQLGVAA [SEQ ID NO: 11] inhibited IL-1β induced IL-6 expression in mesothelial cells. These results further show that the highest concentration of the therapeutic inhibitor peptide YARAAARQARAKALARQLGVAA [SEQ ID NO: 11] (3 mM) and Rottlerin (1 µM) significantly reduced IL-1β induced IL-6 expression. The results also show that a significant reduction of IL-1β induced IL-6 expression by the therapeutic inhibitor peptide YARAAARQARAKALARQLGVAA [SEQ ID NO: 11] (3 mM) occurs earlier (at 6 hours) than that elicited by Rottlerin (12 hours).

6.5. Regulation of IL-6 Expression with Induction by TNF-α

Mesothelial cells were incubated with TNF-α (to induce IL-6 expression) and/or different concentrations of a therapeutic inhibitor peptide (YARAAARQARAKALARQLGVAA [SEQ ID NO: 11] or FAKLAARLYRKALARQLGVAA [SEQ ID NO: 12]). The commercially available protein kinase inhibitor Rottlerin was used as an inhibitor of MK2.

Figure 8:
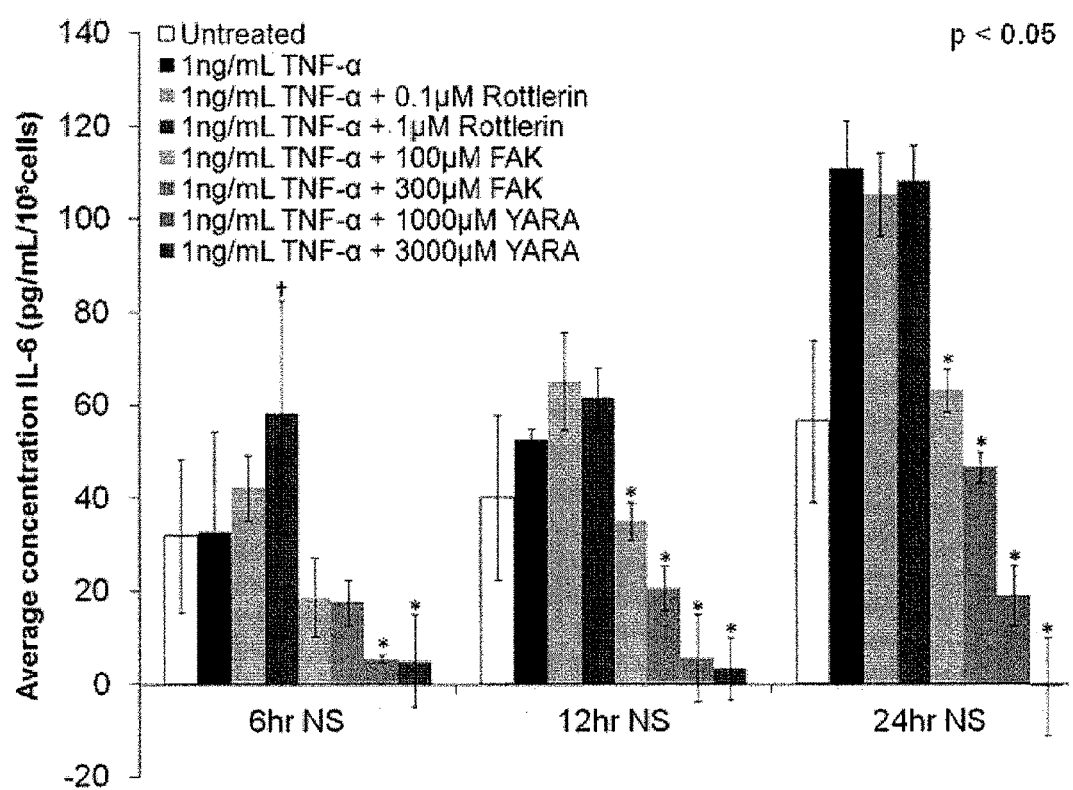
FIG. 8 shows a plot of the average concentration of IL-6 (pg/ml/$10^5$ cells) against time. YARA=YARAAARQARAKALARQLGVAA [SEQ ID NO: 11]; FAK=FAKLAARLYRKALARQLGVAA [SEQ ID NO: 12]. *=significantly lower than 1 ng/mL TNF-α treated samples. Error bars represent standard deviation between three samples.

FIG. 8 shows a plot of the average concentration of IL-6 (pg/ml/$10^5$ cells) against time. These results show that both of the therapeutic inhibitor peptides reduced the level of expression of IL-6 induced by TNF-α (1 ng/ml) and further suggest the effect of the therapeutic inhibitor peptides may be dose dependent. The results also show that the protein kinase inhibitor Rottlerin was ineffective at reducing the level of expression of IL-6 induced by TNF-α (1 ng/ml).

Figure 9:
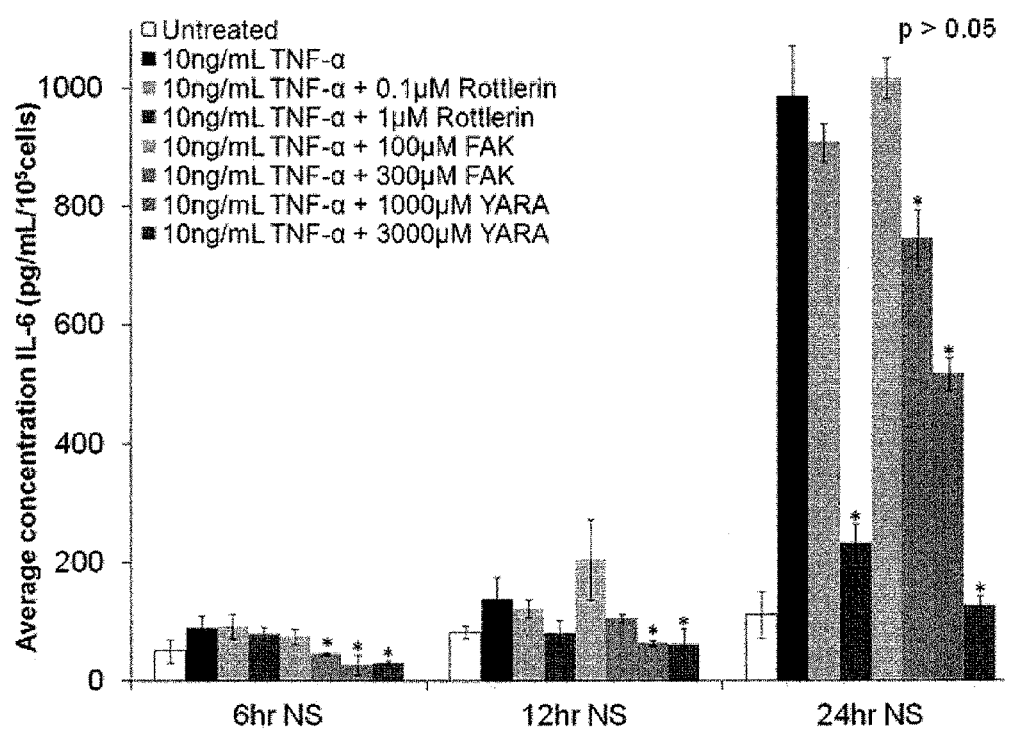
FIG. 9 shows a plot of the average concentration of IL-6 (pg/ml/$10^5$ cells) against time. YARA=YARAAARQARAKALARQLGVAA [SEQ ID NO: 11]; FAK=FAKLAARLYRKALARQLGVAA [SEQ ID NO: 12]. *=significantly lower than 10 ng/mL TNF-α treated samples. Error bars represent standard deviation between three samples.

FIG. 9 shows a plot of the average concentration of IL-6 (pg/ml/$10^5$ cells) against time. These results show that both of the therapeutic inhibitor peptides reduced the level of expression of IL-6 induced by TNF-α (10 ng/ml) and further suggest the effect of the therapeutic inhibitor peptides may be dose dependent. The results also show that the protein kinase inhibitor Rottlerin initially (from 6-12 hours) affected minimal reduction of the level of expression of IL-6 induced by TNF-α (10 ng/ml).

Example 7

Effect of MK2i on IL-1β Production

The inhibitory effect of therapeutic inhibitor protein having amino acid sequence YARAAARQARAKALARQLGVAA [SEQ ID NO: 11] on IL-1β production was studied in neural cells.

Primary cortical astrocyte cultures were established. Primary rat astrocytes were isolated from embryonic day 18 Sprague Dawley rat cortices. Cells were isolated by following the suggested Brain Bits protocol and grown to confluency on poly-lysine (PDL) 100 mm petri dishes. Briefly, the rat cortexes were triturated with a 1 ml pipet aid until most of the large cortex pieces were dispersed. After larger tissue fragments were allowed to settle, the supernatant was collected, in a 15 ml conical tube, and pelleted by centrifugation at 1100 rpm for 1 minute. The resulting supernatant was discarded and the pellet resuspended in neurobasal media (10% horse serum, 3 mM glutamine). The astrocytes then were seeded in the petri dishes and grown until they were confluent (80-95%) after which time they were passed. Astrocytes were passed 1:4, grown to 80-95% confluency, then rinsed twice with PBS. Different treatment types were applied to each corresponding petri dish for 18-22 hours. There was a total of 1 ml of media (neurobasal media with 10% horse serum, 3 mM glutamine) plus treatment in each petri dish. The positive control comprised treating the cells with TNF-α (either 5 ng/ml or 10 ng/ml); as a negative control, the cells were exposed to cell media without any treatment. The treatment groups consisted of (i) 1 mM MK2i (therapeutic inhibitor peptide YARAAARQARAKALARQLGVAA [SEQ ID NO: 11]) with TNF-α (5 ng/ml); (ii) 3 mM MK2i with TNF-α (5 ng/ml); (iii) 1 mM MK2i with TNF-α (10 ng/ml TNF-α); and (iv) 3 mM MK2i with TNF-α (10 ng/ml). Cytokines with or without therapeutic inhibitor peptide were always added simultaneously in this media formulation.

After 18-22 hours, the cells were rinsed with PBS, scraped into a small centrifuge tube using a lysis buffer (8 M urea, 4% CHAPS, 10 mM DTT), and disrupted by using a Disruptor Genie™ (Scientific Industries, Bohemia, N.Y.) for 2 hours.

The cells were pelleted by centrifugation at 17 krpm for 15 minutes, the supernatant (cell lysate) collected and the total protein concentration quantified (Pierce BCA Protein Assay kit, Thermo Fisher Scientific, Rockford, Ill.).

Figure 10:
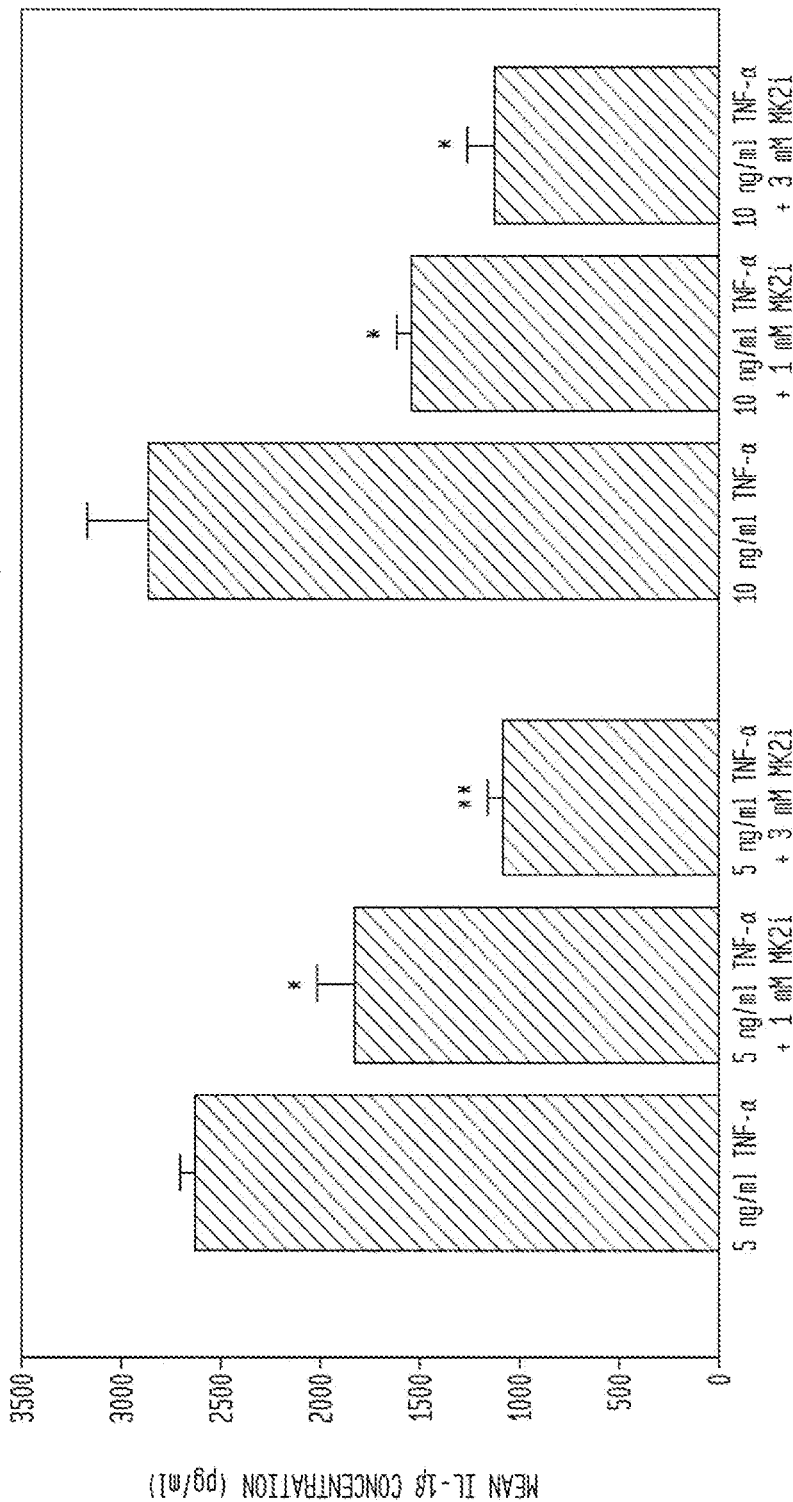
FIG. 10 shows a graph of the mean IL-1β concentration (pg/ml) from each treatment group (i) 1 mM MK2i (therapeutic inhibitor peptide YARAAARQARAKALARQLGVAA [SEQ ID NO: 11]) with TNF-α (5 ng/ml); (ii) 3 mM MK2i with TNF-α (5 ng/ml); (iii) 1 mM MK2i with TNF-α, (10 ng/ml); and (iv) 3 mM MK2i with TNF-α (10 ng/ml).

FIG. 10 shows a graph of the mean IL-1β concentration (pg/ml) from each treatment group (i) 1 mM MK2i (therapeutic inhibitor peptide YARAAARQARAKALARQLGVAA [SEQ ID NO: 11]) with TNF-α (5 ng/ml); (ii) 3 mM MK2i with TNF-α (5 ng/ml); (iii) 1 mM MK2i with TNF-α (10 ng/ml); and (iv) 3 mM MK2i with TNF-α (10 ng/ml). These results show that TNF-α increased the IL-1β concentration, as expected, and the therapeutic inhibitor peptide was able to inhibit the level of expression of IL-1β in rat primary cortical astrocyte cultures in a dose-dependent manner. The results suggest that the therapeutic inhibitor peptide will actively limit glial scarring that is due to induced inflammatory cytokine expression.

Example 8

Effect of MAPKAP Kinase 2 Inhibition (MK2i) on IL-6 Production

The inhibitory effect of therapeutic inhibitor protein having amino acid sequence YARAAARQARAKALARQLGVAA [SEQ ID NO: 11] on IL-6 production was studied in a triple culture consisting of neurons, astrocytes and microglia. Cell media was prepared as follows. Briefly, Dulbecco's Modified Eagle Medium (DMEM) (6.68 g) and sodium bicarbonate (1.85 g) were added to distilled de-ionized (DDi) water (500 ml); the suspension was filter sterilized and, then supplemented with penicillin/streptomycin (500 µl), fetal bovine serum (FBS) (50 ml), and human serum (HS) (50 ml). The prepared media was added (1 ml) to the tissue, and the tissue triturated 10 times over 30 seconds through a sterile pipet tip. The cell suspension was filtered through a nylon filter and collected. The filtered suspension was centrifuged at 1100 rpm for 1 minute and the pellet resuspended. The E18 cells were plated (1×10⁶ cells/ml) to support differentiation into neurons, astrocytes and microglia. After one week in culture, some cells were fixed and probed for β-3 tubulin (a biomarker for neurons), glial fibrillary acidic protein (GFAP, a biomarker for astrocytes) and ionized calcium binding adaptor molecule 1 (Iba1, a biomarker for microglia) to validate the presence of all three cell types. The primary antibodies used included rabbit anti-Iba1 (1:200; Wako Chemicals USA, Inc., Richmond, Va.), chicken anti-GFAP (1:200; Millipore Corp., Billerica, Mass.), and mouse anti-β-3-tubulin conjugated to Alexa Fluor 488 (1:200; Millipore Corp., Billerica, Mass.). The secondary antibodies included Alexa Fluor 633 goat anti-rabbit (1:200; Invitrogen, Carlsbad, Calif.), and Alexa Fluor 555 goat anti-chicken (1:200; Invitrogen, Carlsbad, Calif.). The nuclei were labeled with Hoescht 33342 (Invitrogen, Carlsbad, Calif.). The positive control comprised treating the cells with TNF-α (either 5 ng/ml or 10 ng/ml); as a negative control, the cells were exposed to cell media without any treatment. The treatment groups consisted of (i) 1 mM MK2i (therapeutic inhibitor peptide YARAAARQARAKALARQLGVAA [SEQ ID NO: 11]) with TNF-α (5 ng/ml); (ii) 3 mM MK2i with TNF-α (5 ng/ml); (iii) 1 mM MK2i with TNF-α (10 ng/ml TNF-α); and (iv) 3 mM MK2i with TNF-α (10 ng/ml). Cytokines with or without therapeutic inhibitor peptide were always added simultaneously in this media formulation.

Figure 11:
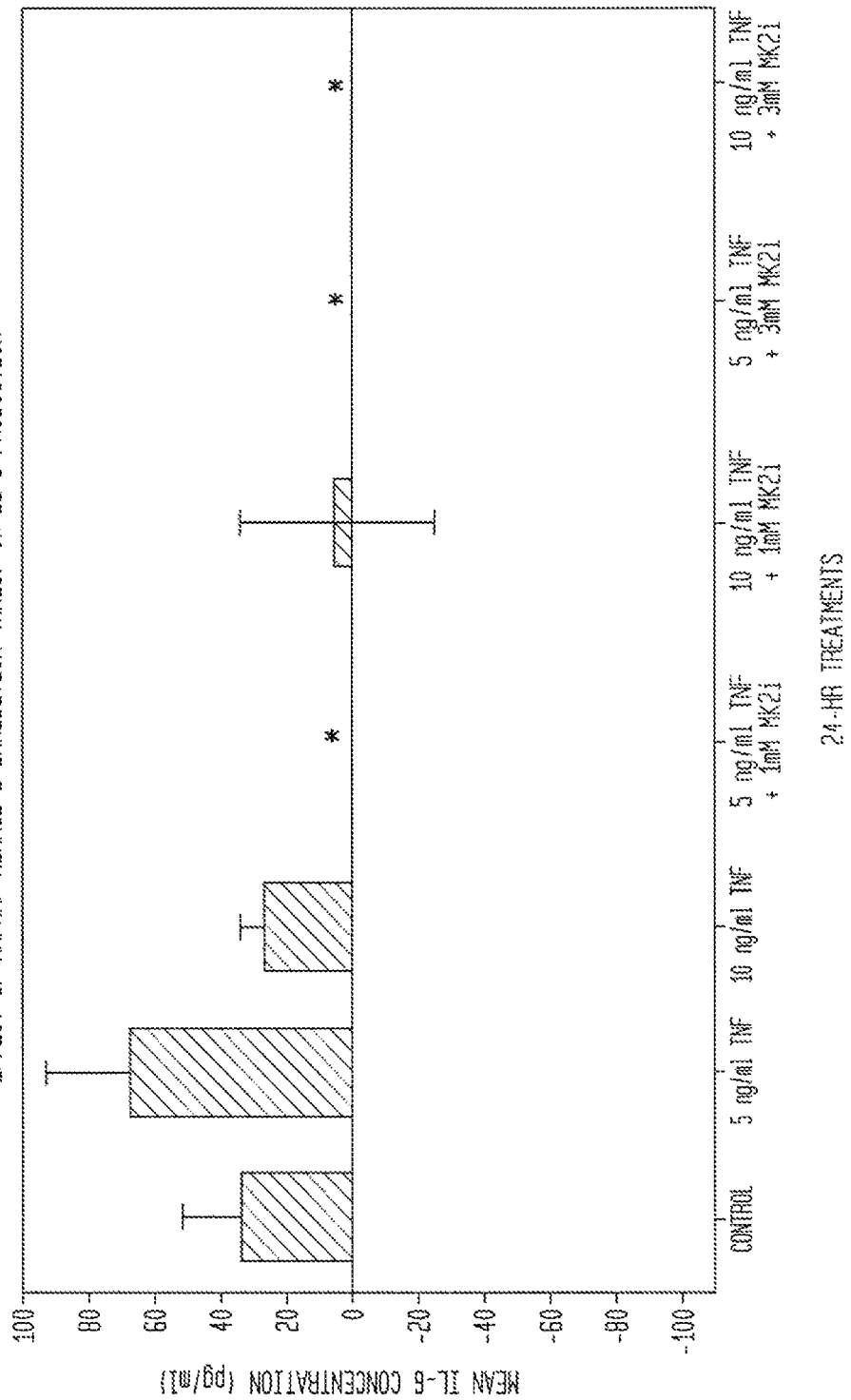
FIG. 11 shows a graph of the mean IL-6 concentration (pg/ml) from each treatment group (i) negative control (media only); (ii) TNF-α (5 ng/ml); (iii) TNF-α (10 ng/ml); (iv) TNF-α (5 ng/l) and MK2i (1 mM therapeutic inhibitor peptide YARAAARQARAKALARQLGVAA [SEQ ID NO: 11]); (v) TNF-α (10 ng/ml) and MK2i (1 mM); (vi) TNF-α (5 ng/ml) and MK2i (3 mM); and (vii) TNF-α (10 ng/ml) and MK2i (3 mM).

FIG. 11 shows a graph of the mean IL-6 concentration (pg/ml) from each treatment group (i) negative control (media only); (ii) TNF-α (5 ng/ml); (iii) TNF-α (10 ng/ml); (iv) TNF-α (5 ng/l) and MK2i (1 mM therapeutic inhibitor peptide YARAAARQARAKALARQLGVAA [SEQ ID NO: 11]); (v) TNF-α (10 ng/ml) and MK2i (1 mM); (vi) TNF-α (5 ng/ml) and MK2i (3 mM); and (vii) TNF-α (10 ng/ml) and MK2i (3 mM). These results show that TNF-α (5 ng/ml) increased the level of expression of IL-6 in the cell cultures and that all of the cell cultures treated with the therapeutic inhibitor peptide had reduced levels of expression of IL-6.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating an inflammatory disorder characterized by IL-6 expression induced by IL-1β, TNF-α, or a combination thereof, the method comprising the step of:
administering a kinase inhibiting composition to a subject in need thereof, wherein the kinase inhibiting composition comprises
(a) a therapeutic amount of a therapeutic MK2 kinase inhibitor peptide comprising a protein transduction domain and a therapeutic domain, wherein the therapeutic domain has amino acid sequence KALARQLGVAA [SEQ ID NO: 23]; and
(b) a pharmaceutically acceptable carrier,
wherein the therapeutic amount of the composition is effective
(a) to inhibit an MK2 kinase; and
(b) to reduce expression of IL-6 induced by IL-1β, TNF-α, or a combination thereof, and thereby treat the inflammatory disorder.

2. The method according to claim 1, wherein the therapeutic inhibitor peptide has the amino acid sequence YARAAARQARAKALARQLGVAA [SEQ ID NO: 11].

3. The method according to claim 1, wherein the protein transduction domain of the therapeutic inhibitor peptide has substantial identity to the amino acid sequence WLRRIKAWLRRIKA [SEQ ID NO: 31].

4. The method according to claim 1, wherein the protein transduction domain of the therapeutic inhibitor peptide has the amino acid sequence YARAAARQARA [SEQ ID NO: 5].

5. The method according to claim 1, wherein the protein transduction domain of the therapeutic inhibitor peptide has substantial identity to the amino acid sequence FAKLAARLYR [SEQ ID NO: 35].

6. The method according to claim 1, wherein the therapeutic inhibitor peptide has substantial identity to the amino acid sequence FAKLAARLYRKALARQLGVAA [SEQ ID NO: 12].

7. (Withdrawn-previously presented) The method according to claim 1, wherein the protein transduction domain of the therapeutic inhibitor peptide has substantial identity to the amino acid sequence KAFAKLAARLYR [SEQ ID NO: 36].

8. The method according to claim 1, wherein the therapeutic inhibitor peptide has substantial identity to the amino acid sequence KAFAKLAARLYRKALARQLGVAA [SEQ ID NO: 15].

9. The method according to claim 1, wherein the polypeptide comprises at least one variant that consists of one of SEQ ID NO: 11, SEQ ID NO: 12, and SEQ ID NO: 15 and wherein the peptide inhibits TNF-α expression.

10. The method according to claim 1, wherein the polypeptide comprises at least one variant that consists of one of SEQ ID NO: 11, SEQ ID NO: 12, and SEQ ID NO: 15 and wherein the peptide inhibits IL-1β expression.

11. The method according to claim 1, wherein the polypeptide comprises at least one variant that consists one of SEQ ID NO: 11, SEQ ID NO: 12, and SEQ ID NO: 15 and wherein the peptide inhibits IL-6 expression.

12. The method according to claim 1, wherein the kinase enzyme is a mitogen-activated protein kinase-activated protein kinase.

13. The method according to 12, wherein the kinase enzyme is mitogen-activated protein kinase-activated protein kinase 2.

14. The method according to claim 12, wherein the kinase enzyme is mitogen-activated protein kinase-activated protein kinase 3.

15. The method according to claim 1, wherein the kinase enzyme is a $Ca^{2+}$/calmodulin-dependent protein kinase.

16. The method according to claim 1, wherein the administering step is by implanting a biomedical device, wherein the composition is disposed on or in the device.

17. The method according to claim 1, wherein the administering step is parenteral administration.

18. The method according to claim 1, wherein the polypeptide comprises a variant that consists of SEQ ID NO: 11 and wherein the peptide inhibits TNF-α expression.

19. The method according to claim 1, wherein the polypeptide comprises a variant that is at least 90% identical to SEQ ID NO: 12 and wherein the peptide inhibits TNF-α expression.

20. The method according to claim 1, wherein the polypeptide comprises a variant that is at least 90% identical to SEQ ID NO: 15 and wherein the peptide inhibits TNF-α expression.

21. The method according to claim 1, wherein the polypeptide comprises a variant that consists of SEQ ID NO: 11 and wherein the peptide inhibits IL-1β expression.

22. The method according to claim 1, wherein the polypeptide comprises a variant that is at least 90% identical to SEQ ID NO: 12 and wherein the peptide inhibits IL-1β expression.

23. The method according to claim 1, wherein the polypeptide comprises a variant that is at least 90% identical to SEQ ID NO: 15 and wherein the peptide inhibits IL-1β expression.

24. The method according to claim 1, wherein the polypeptide comprises a variant that consists of SEQ ID NO: 11 and wherein the peptide inhibits IL-6expression.

25. The method according to claim 1, wherein the polypeptide comprises a variant that is at least 90% identical to SEQ ID NO: 12 and wherein the peptide inhibits IL-6 expression.

26. The method according to claim 1, wherein the polypeptide comprises a variant that is at least 90% identical to SEQ ID NO: 15 and wherein the peptide inhibits IL-6 expression.

27. The method according to claim 1, wherein the therapeutic inhibitor peptide is synthetic.

28. The method according to claim 1, wherein the therapeutic inhibitor peptide comprises D-amino acids, L-amino acids, or a combination thereof.

29. The method according to claim 1, wherein the pharmaceutically acceptable carrier comprises a sterile aqueous solution.

30. The method according to claim 1, wherein the therapeutic inhibitor peptide is an isolated peptide.

31. The method according to claim 1, wherein the kinase inhibiting composition further comprises a preservative.

32. The method according to claim 1, wherein the composition further comprises a unit-dosage or multi-dosage container for the composition.

33. The method according to claim 32, wherein the container is a sterile vial or an ampule.

34. The method according to claim 1, wherein the therapeutic domain of the therapeutic inhibitor peptide has substantial identity to the amino acid sequence KALNRQLGVA [SEQ ID NO: 29].

35. The method according to claim 1, wherein the therapeutic domain of the therapeutic inhibitor peptide has substantial identity to the amino acid sequence KALNRQLAVAA [SEQ ID NO: 27].

36. The method according to claim 1, wherein the therapeutic inhibitor peptide has substantial identity to the amino acid sequence YARAAARQARAKALNRQLGVA wherein the protein transduction domain of the therapeutic inhibitor peptide has the amino acid sequence YARAAARQARA (SEQ ID NO: 5), and wherein the therapeutic domain of the therapeutic inhibitor peptide has substantial identity to the amino acid sequence KALNRQLGVA (SEQ ID NO: 29).

37. The method according to claim 1, wherein the therapeutic inhibitor peptide has substantial identity to the amino acid sequence YARAAARQARAKALNRQLAVAA wherein the protein transduction domain of the therapeutic inhibitor peptide has the amino acid sequence YARAAARQARA (SEQ ID NO: 5), and wherein the therapeutic domain of the therapeutic inhibitor peptide has substantial identity to the amino acid sequence KALNRQLGVAA (SEQ ID NO: 27).

* * * * *

SEQUENCE LISTING

```
<160> NUMBER OF SEQ ID NOS: 71

<210> SEQ ID NO 1
<211> LENGTH: 13
<212> TYPE: PRT
<213> ORGANISM: Unknown
<220> FEATURE:
<223> OTHER INFORMATION: Description of Unknown: Mammalian
      peptide

<400> SEQUENCE: 1

Gly Met Pro Lys Lys Pro Thr Pro Ile Gln Leu Asn
1               5                   10

<210> SEQ ID NO 2
<211> LENGTH: 17
<212> TYPE: PRT
<213> ORGANISM: Unknown
<220> FEATURE:
<223> OTHER INFORMATION: Description of Unknown: Mammalian
      peptide
```

-continued

<400> SEQUENCE: 2

Asp Arg Gln Ile Lys Ile Trp Phe Gln Asn Arg Met Lys Trp Lys
1               5                   10                  15

Lys

<210> SEQ ID NO 3
<211> LENGTH: 13
<212> TYPE: PRT
<213> ORGANISM: Unknown
<220> FEATURE:
<223> OTHER INFORMATION: Description of Unknown: Mammalian
      peptide

<400> SEQUENCE: 3

Lys Lys Ala Leu Arg Arg Gln Glu Ala Val Asp Ala Leu
1               5                   10

<210> SEQ ID NO 4
<211> LENGTH: 9
<212> TYPE: PRT
<213> ORGANISM: Human immunodeficiency virus

<400> SEQUENCE: 4

Arg Lys Lys Arg Arg Gln Arg Arg Arg
1               5

<210> SEQ ID NO 5
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 5

Tyr Ala Arg Ala Ala Ala Arg Gln Ala Arg Ala
1               5                   10

<210> SEQ ID NO 6
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 6

Arg Arg Gln Arg Arg Thr Ser Lys Leu Met Lys Arg
1               5                   10

<210> SEQ ID NO 7
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 7

Ala Ala Val Leu Leu Pro Val Leu Leu Ala Ala Arg
1               5                   10

<210> SEQ ID NO 8
<211> LENGTH: 9
<212> TYPE: PRT

```
<213> ORGANISM: Unknown
<220> FEATURE:
<223> OTHER INFORMATION: Description of Unknown: Mammalian
      peptide

<400> SEQUENCE: 8

Arg Arg Arg Arg Arg Arg Arg Arg
1               5

<210> SEQ ID NO 9
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 9

Ser Gly Trp Phe Arg Arg Trp Lys Lys
1               5

<210> SEQ ID NO 10
<211> LENGTH: 16
<212> TYPE: PRT
<213> ORGANISM: Unknown
<220> FEATURE:
<223> OTHER INFORMATION: Description of Unknown: Mammalian
      peptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 22
<212> TYPE: PRT
<213> ORGANISM: Unknown
<220> FEATURE:
<223> OTHER INFORMATION: Description of Unknown: Mammalian
      peptide

<400> SEQUENCE: 11

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 12
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 12

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 13
<211> LENGTH: 11
<212> TYPE: PRT
<213> ORGANISM: Unknown
<220> FEATURE:
<223> OTHER INFORMATION: Description of Unknown: Mammalian
``` peptide

<400> SEQUENCE: 13

Lys Ala Leu Asn Arg Gln Leu Gly Val Ala Ala
1               5                   10

<210> SEQ ID NO 14
<211> LENGTH: 23
<212> TYPE: PRT
<213> ORGANISM: Unknown
<220> FEATURE:
<223> OTHER INFORMATION: Description of Unknown: Mammalian
      peptide

<400> SEQUENCE: 14

Trp Leu Arg Arg Ile Lys Ala Trp Leu Arg Arg Ile Lys Ala Leu Asn
1               5                   10                  15

Arg Gln Leu Gly Val Ala Ala
            20

<210> SEQ ID NO 15
<211> LENGTH: 23
<212> TYPE: PRT
<213> ORGANISM: Unknown
<220> FEATURE:
<223> OTHER INFORMATION: Description of Unknown: Mammalian
      peptide

<400> SEQUENCE: 15

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 16
<211> LENGTH: 22
<212> TYPE: PRT
<213> ORGANISM: Unknown
<220> FEATURE:
<223> OTHER INFORMATION: Description of Unknown: Mammalian
      peptide

<400> SEQUENCE: 16

Tyr Ala Arg Ala Ala Ala Arg Gln Ala Arg Ala Lys Ala Leu Asn Arg
1               5                   10                  15

Gln Leu Gly Val Ala Ala
            20

<210> SEQ ID NO 17
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 17

Tyr Ala Arg Ala Ala Ala Arg Gly Gln Arg Ala Lys Ala Leu Ala Arg
1               5                   10                  15

Gln Leu Ala Val Ala
            20

<210> SEQ ID NO 18
<211> LENGTH: 21
<212> TYPE: PRT

```
<213> ORGANISM: Unknown
<220> FEATURE:
<223> OTHER INFORMATION: Description of Unknown: Mammalian
      peptide

<400> SEQUENCE: 18

Tyr Ala Arg Ala Ala Ala Arg Gly Gln Arg Ala Lys Ala Leu Ala Arg
1               5                   10                  15

Gln Leu Gly Val Ala
            20

<210> SEQ ID NO 19
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 19

Tyr Ala Arg Ala Ala Ala Arg Gly Gln Arg Ala Lys Ala Leu Asn Arg
1               5                   10                  15

Gln Leu Ala Val Ala
            20

<210> SEQ ID NO 20
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 20

Tyr Ala Arg Ala Ala Ala Arg Gly Gln Arg Ala Lys Ala Leu Asn Arg
1               5                   10                  15

Gln Leu Gly Val Ala
            20

<210> SEQ ID NO 21
<211> LENGTH: 22
<212> TYPE: PRT
<213> ORGANISM: Unknown
<220> FEATURE:
<223> OTHER INFORMATION: Description of Unknown: Mammalian
      peptide

<400> SEQUENCE: 21

Tyr Ala Arg Ala Ala Ala Arg Gly Gln Arg Ala Lys Ala Leu Asn Arg
1               5                   10                  15

Gln Leu Gly Val Ala Ala
            20

<210> SEQ ID NO 22
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 22

Lys Ala Ala Asn Arg Gln Leu Gly Val Ala Ala
1               5                   10
```

```
<210> SEQ ID NO 23
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 23

Lys Ala Leu Ala Arg Gln Leu Gly Val Ala Ala
1               5                   10

<210> SEQ ID NO 24
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 24

Lys Ala Leu Asn Ala Gln Leu Gly Val Ala Ala
1               5                   10

<210> SEQ ID NO 25
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 25

Lys Ala Leu Asn Arg Ala Leu Gly Val Ala Ala
1               5                   10

<210> SEQ ID NO 26
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 26

Lys Ala Leu Asn Arg Gln Ala Gly Val Ala Ala
1               5                   10

<210> SEQ ID NO 27
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 27

Lys Ala Leu Asn Arg Gln Leu Ala Val Ala Ala
1               5                   10

<210> SEQ ID NO 28
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 28
```

```
Lys Ala Leu Asn Arg Gln Leu Gly Ala Ala Ala
1               5                   10

<210> SEQ ID NO 29
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 29

Lys Ala Leu Asn Arg Gln Leu Gly Val Ala
1               5                   10

<210> SEQ ID NO 30
<211> LENGTH: 13
<212> TYPE: PRT
<213> ORGANISM: Unknown
<220> FEATURE:
<223> OTHER INFORMATION: Description of Unknown: Mammalian
      peptide

<400> SEQUENCE: 30

Lys Lys Lys Ala Leu Asn Arg Gln Leu Gly Val Ala Ala
1               5                   10

<210> SEQ ID NO 31
<211> LENGTH: 14
<212> TYPE: PRT
<213> ORGANISM: Unknown
<220> FEATURE:
<223> OTHER INFORMATION: Description of Unknown: Mammalian
      peptide

<400> SEQUENCE: 31

Trp Leu Arg Arg Ile Lys Ala Trp Leu Arg Arg Ile Lys Ala
1               5                   10

<210> SEQ ID NO 32
<211> LENGTH: 7
<212> TYPE: PRT
<213> ORGANISM: Unknown
<220> FEATURE:
<223> OTHER INFORMATION: Description of Unknown: Mammalian
      peptide

<400> SEQUENCE: 32

Trp Leu Arg Arg Ile Lys Ala
1               5

<210> SEQ ID NO 33
<211> LENGTH: 11
<212> TYPE: PRT
<213> ORGANISM: Unknown
<220> FEATURE:
<223> OTHER INFORMATION: Description of Unknown: Mammalian
      peptide

<400> SEQUENCE: 33

Tyr Gly Arg Lys Lys Arg Arg Gln Arg Arg
1               5                   10

<210> SEQ ID NO 34
<211> LENGTH: 12
<212> TYPE: PRT
<213> ORGANISM: Unknown
```

```
<220> FEATURE:
<223> OTHER INFORMATION: Description of Unknown: Mammalian
      peptide

<400> SEQUENCE: 34

Trp Leu Arg Arg Ile Lys Ala Trp Leu Arg Ile
1               5                   10

<210> SEQ ID NO 35
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 35

Phe Ala Lys Leu Ala Ala Arg Leu Tyr Arg
1               5                   10

<210> SEQ ID NO 36
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 36

Lys Ala Phe Ala Lys Leu Ala Ala Arg Leu Tyr Arg
1               5                   10

<210> SEQ ID NO 37
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 37

Tyr Ala Arg Ala Ala Ala Arg Gly Gln Ala Arg Ala
1               5                   10

<210> SEQ ID NO 38
<211> LENGTH: 13
<212> TYPE: PRT
<213> ORGANISM: Unknown
<220> FEATURE:
<223> OTHER INFORMATION: Description of Unknown: Mammalian
      peptide

<400> SEQUENCE: 38

Trp Leu Arg Arg Arg Ile Lys Ala Trp Leu Arg Arg Ile
1               5                   10

<210> SEQ ID NO 39
<211> LENGTH: 19
<212> TYPE: PRT
<213> ORGANISM: Unknown
<220> FEATURE:
<223> OTHER INFORMATION: Description of Unknown: Mammalian
      peptide

<400> SEQUENCE: 39

Phe Ala Lys Leu Ala Ala Arg Leu Tyr Arg Leu Ala Arg Gln Leu Gly
1               5                   10                  15
```

Val Ala Ala

<210> SEQ ID NO 40
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 40

Lys Ala Phe Ala Lys Leu Ala Ala Arg Leu Tyr Arg Leu Ala Arg Gln
1               5                   10                  15

Leu Gly Val Ala Ala
            20

<210> SEQ ID NO 41
<211> LENGTH: 20
<212> TYPE: PRT
<213> ORGANISM: Unknown
<220> FEATURE:
<223> OTHER INFORMATION: Description of Unknown: Mammalian
      peptide

<400> SEQUENCE: 41

Tyr Ala Arg Ala Ala Ala Arg Gln Ala Arg Ala Leu Ala Arg Gln Leu
1               5                   10                  15

Gly Val Ala Ala
            20

<210> SEQ ID NO 42
<211> LENGTH: 20
<212> TYPE: PRT
<213> ORGANISM: Unknown
<220> FEATURE:
<223> OTHER INFORMATION: Description of Unknown: Mammalian
      peptide

<400> SEQUENCE: 42

Tyr Ala Arg Ala Ala Ala Arg Gln Ala Arg Ala Leu Asn Arg Gln Leu
1               5                   10                  15

Gly Val Ala Ala
            20

<210> SEQ ID NO 43
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 43

Phe Ala Lys Leu Ala Ala Arg Leu Tyr Arg Lys Ala
1               5                   10

<210> SEQ ID NO 44
<211> LENGTH: 14
<212> TYPE: PRT
<213> ORGANISM: Unknown
<220> FEATURE:
<223> OTHER INFORMATION: Description of Unknown: Mammalian
      peptide

<400> SEQUENCE: 44

Lys Ala Phe Ala Lys Leu Ala Ala Arg Leu Tyr Arg Lys Ala

```
<210> SEQ ID NO 45
<211> LENGTH: 8
<212> TYPE: PRT
<213> ORGANISM: Unknown
<220> FEATURE:
<223> OTHER INFORMATION: Description of Unknown: Mammalian
      peptide
<220> FEATURE:
<221> NAME/KEY: MOD_RES
<222> LOCATION: (3)..(3)
<223> OTHER INFORMATION: Any amino acid

<400> SEQUENCE: 45

Lys Lys Xaa Lys Arg Arg Lys Lys
1               5

<210> SEQ ID NO 46
<211> LENGTH: 7
<212> TYPE: PRT
<213> ORGANISM: Unknown
<220> FEATURE:
<223> OTHER INFORMATION: Description of Unknown: Mammalian
      peptide

<400> SEQUENCE: 46

Leu Leu Lys Arg Arg Lys Lys
1               5

<210> SEQ ID NO 47
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 47

Trp Leu Arg Arg Ile Lys Ala Trp Leu Arg Arg Ile Lys Ala Leu Asn
1               5                   10                  15

Arg Gln Leu Gly Val
            20

<210> SEQ ID NO 48
<211> LENGTH: 12
<212> TYPE: PRT
<213> ORGANISM: Unknown
<220> FEATURE:
<223> OTHER INFORMATION: Description of Unknown: Mammalian
      peptide

<400> SEQUENCE: 48

Glu Ala Ile Tyr Ala Ala Pro Phe Ala Lys Lys Lys
1               5                   10

<210> SEQ ID NO 49
<211> LENGTH: 15
<212> TYPE: PRT
<213> ORGANISM: Unknown
<220> FEATURE:
<223> OTHER INFORMATION: Description of Unknown: Mammalian
      peptide

<400> SEQUENCE: 49

Ala Met Ala Arg Ala Ala Ser Ala Ala Leu Ala Arg Arg Arg
1               5                   10                  15
```

```
<210> SEQ ID NO 50
<211> LENGTH: 7
<212> TYPE: PRT
<213> ORGANISM: Unknown
<220> FEATURE:
<223> OTHER INFORMATION: Description of Unknown: Mammalian
      peptide

<400> SEQUENCE: 50

Leu Arg Arg Ala Ser Leu Gly
1               5

<210> SEQ ID NO 51
<211> LENGTH: 15
<212> TYPE: PRT
<213> ORGANISM: Unknown
<220> FEATURE:
<223> OTHER INFORMATION: Description of Unknown: Mammalian
      peptide

<400> SEQUENCE: 51

Lys Val Glu Lys Ile Gly Glu Gly Thr Tyr Gly Val Val Tyr Lys
1               5                   10                  15

<210> SEQ ID NO 52
<211> LENGTH: 13
<212> TYPE: PRT
<213> ORGANISM: Unknown
<220> FEATURE:
<223> OTHER INFORMATION: Description of Unknown: Mammalian
      peptide

<400> SEQUENCE: 52

Lys Lys Leu Asn Arg Thr Leu Ser Phe Ala Glu Pro Gly
1               5                   10

<210> SEQ ID NO 53
<211> LENGTH: 23
<212> TYPE: PRT
<213> ORGANISM: Unknown
<220> FEATURE:
<223> OTHER INFORMATION: Description of Unknown: Mammalian
      peptide

<400> SEQUENCE: 53

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 54
<211> LENGTH: 14
<212> TYPE: PRT
<213> ORGANISM: Unknown
<220> FEATURE:
<223> OTHER INFORMATION: Description of Unknown: Mammalian
      peptide
<220> FEATURE:
<221> NAME/KEY: MOD_RES
<222> LOCATION: (7)..(7)
<223> OTHER INFORMATION: (p)Ser

<400> SEQUENCE: 54

Lys Arg Arg Arg Ala Leu Ser Val Ala Ser Leu Pro Gly Leu
1               5                   10

<210> SEQ ID NO 55
```

```
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 55

Arg Arg Arg Asp Asp Asp Ser Asp Asp Asp
1               5                   10

<210> SEQ ID NO 56
<211> LENGTH: 14
<212> TYPE: PRT
<213> ORGANISM: Unknown
<220> FEATURE:
<223> OTHER INFORMATION: Description of Unknown: Mammalian
      peptide

<400> SEQUENCE: 56

Lys Lys Lys Ser Pro Gly Glu Tyr Val Asn Ile Glu Phe Gly
1               5                   10

<210> SEQ ID NO 57
<211> LENGTH: 26
<212> TYPE: PRT
<213> ORGANISM: Unknown
<220> FEATURE:
<223> OTHER INFORMATION: Description of Unknown: Mammalian
      peptide
<220> FEATURE:
<221> NAME/KEY: MOD_RES
<222> LOCATION: (21)..(21)
<223> OTHER INFORMATION: (p)Ser

<400> SEQUENCE: 57

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 58
<211> LENGTH: 15
<212> TYPE: PRT
<213> ORGANISM: Unknown
<220> FEATURE:
<223> OTHER INFORMATION: Description of Unknown: Mammalian
      peptide

<400> SEQUENCE: 58

Gly Gly Glu Glu Glu Glu Tyr Phe Glu Leu Val Lys Lys Lys Lys
1               5                   10                  15

<210> SEQ ID NO 59
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 59

Lys Lys Arg Asn Arg Thr Leu Thr Val
1               5

<210> SEQ ID NO 60
<211> LENGTH: 13
<212> TYPE: PRT
```

```
<213> ORGANISM: Unknown
<220> FEATURE:
<223> OTHER INFORMATION: Description of Unknown: Mammalian
      peptide

<400> SEQUENCE: 60

Gly Arg Pro Arg Thr Ser Ser Phe Ala Glu Gly Lys Lys
1               5                   10

<210> SEQ ID NO 61
<211> LENGTH: 16
<212> TYPE: PRT
<213> ORGANISM: Unknown
<220> FEATURE:
<223> OTHER INFORMATION: Description of Unknown: Mammalian
      peptide

<400> SEQUENCE: 61

Glu Arg Met Arg Pro Arg Lys Arg Gln Gly Ser Val Arg Arg Arg Val
1               5                   10                  15

<210> SEQ ID NO 62
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 62

Arg Arg Arg Leu Ser Phe Ala Glu Pro Gly
1               5                   10

<210> SEQ ID NO 63
<211> LENGTH: 32
<212> TYPE: PRT
<213> ORGANISM: Unknown
<220> FEATURE:
<223> OTHER INFORMATION: Description of Unknown: Mammalian
      peptide

<400> SEQUENCE: 63

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
                20                  25                  30

<210> SEQ ID NO 64
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 64

Lys Lys Lys Asn Arg Thr Leu Ser Val Ala
1               5                   10

<210> SEQ ID NO 65
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 65
```

Lys Lys Leu Arg Arg Thr Leu Ser Val Ala
1               5                   10

<210> SEQ ID NO 66
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 66

Lys Ala Phe Ala Lys Leu Ala Ala Arg Leu
1               5                   10

<210> SEQ ID NO 67
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 67

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 68
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 68

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 69
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 69

Tyr Ala Arg Ala Ala Ala Arg Gln Ala Arg Ala Lys Ala Leu Asn Arg
1               5                   10                  15

Gln Leu Ala Val Ala
            20

<210> SEQ ID NO 70
<211> LENGTH: 21
<212> TYPE: PRT
<213> ORGANISM: Unknown
<220> FEATURE:
<223> OTHER INFORMATION: Description of Unknown: Mammalian
      peptide

<400> SEQUENCE: 70

-continued

```
Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 71
<211> LENGTH: 23
<212> TYPE: PRT
<213> ORGANISM: Unknown
<220> FEATURE:
<223> OTHER INFORMATION: Description of Unknown: Mammalian
      peptide

<400> SEQUENCE: 71

Tyr Ala Arg Arg Ala Ala Ala Arg Gln Ala Arg Ala Lys Ala Leu Ala
1               5                   10                  15

Arg Gln Leu Gly Val Ala Ala
            20
```